United States Patent
Jaquith et al.

(10) Patent No.: US 7,230,019 B2
(45) Date of Patent: Jun. 12, 2007

(54) IMIDAZO [2,1-B]-1,3,4-THIADIAZOLE SULFONAMIDES

(75) Inventors: James B. Jaquith, Pincourt (CA);
Gerald Villeneuve, Stoke (CA); Alain Boudreault, Montreal (CA); Stephen Morris, Beaconsfield (CA); Jon Durkin, Ottawa (CA); John W. Gillard, Baie D'Urfe (CA); Kimberly Hewitt, Ottawa (CA); H. Nicholas Marsh, Montreal (CA)

(73) Assignee: Aegera Therapeutics, Inc., Verdun (CA)

( * ) Notice: Subject to any disclaimer, the term of this patent is extended or adjusted under 35 U.S.C. 154(b) by 119 days.

(21) Appl. No.: 10/498,548

(22) PCT Filed: Dec. 16, 2002

(86) PCT No.: PCT/CA02/01942

§ 371 (c)(1),
(2), (4) Date: Jun. 14, 2004

(87) PCT Pub. No.: WO03/051890

PCT Pub. Date: Jun. 26, 2003

(65) Prior Publication Data

US 2005/0069492 A1    Mar. 31, 2005

(30) Foreign Application Priority Data

Dec. 14, 2001    (CA)    .................... 2364985

(51) Int. Cl.
*A01N 43/78*    (2006.01)
*A01N 43/82*    (2006.01)
*A61K 9/20*    (2006.01)
*A61K 9/48*    (2006.01)

(52) U.S. Cl. .................. 514/366; 514/362; 424/451; 424/464

(58) Field of Classification Search .................. 514/12
See application file for complete search history.

(56) References Cited

U.S. PATENT DOCUMENTS 5,604,202 A * 2/1997 Kessler et al. ................ 514/12

FOREIGN PATENT DOCUMENTS

GB    1 464 259    *    2/1977

OTHER PUBLICATIONS

Scozzafava, A. and Supuran, C.T., "Complexes with Biologically Active Ligands. Part 10[1] Inhibition of Carbonic Anhydrase Isozymes I and II with Metal Complexes of Imidazo[2,1-b]-1,3,4-Thiadiazole-2-Sulfonamide," XP-002232873, vol. 4(1): 19-26 (1997).
Barnish, Ian T., et al., "Cerebrovasodilatation Through Selective Inhibition of the Enzyme Carbonic Anhydrase. 2. Imidazo[2,1-b]thiadiazole and Imidazo[2,1-b]thiazolesulfonamides," *J. Med. Chem.*, 23: 117-121 (1980).
Khazi, Imtiyaz A.M., et al., "Synthesis, Anticonvulsant and Analgesic Activities of Some 6-Substituted Imidazo(2,1-b)-1,3,4-thiadiazole-2-sulfonamides and Their 5-Bromo Derivatives," *ArzneimForsch Drug Res.* (XP-002232875), 46:949-952 (1996).
Conroy, Curtis W., et al., "The Nonenzymatic Displacement of the Sulfamoyl Group From Different Classes of Aromatic Compounds by Glutathione and Cysteine," *Drug Metabolism and Disposition* (XP009006657), 12(5): 614-618 (1984).
Gadad, Andanappa K., et al., "Synthesis and Antibacterial Activity of Some 5-Guanylhydrazone/thiocyanato-6-arylimidazo[2,1-b]-1,3,4-thiadiazole-2-sulfonamide Derivatives," *Eur. J. Med. Chem.*, 35: 853-857 (2000).
Gadad, Andanappa K., et al., "Synthesis and Biological Evaluation of 5-Formyl-6-arylimidazo(2,1-b)-1,3,4-thiadiazole-2-N-(dimethylaminomethino)sulfonamides as Antitumor Agents," *Arzneim.-Forsch./Drug Res.*, 49(II), Nr. 10: 858-863 (1999).
Supuran, C.T., "Metal Complexes of 1,3,4-Thiadiazole-2,5-Disulfonamide Are Strong Dual Carbonic Anhydrase Inhibitors, Although the Ligand Possesses Very Weak Such Properties," XP-1002232877, vol. 2(6): 331-336 (1995).

* cited by examiner

*Primary Examiner*—Susan Tran
(74) *Attorney, Agent, or Firm*—Elmore Patent Law Group, P.C.; Darlene A. Vanstone; Carolyn S. Elmore

(57) ABSTRACT

This invention relates to compounds of Formula (I) and the use of compounds of Formula (I) as neuroprotective agents in the treatment of neuronal disorders of the central and peripheral nervous systems.

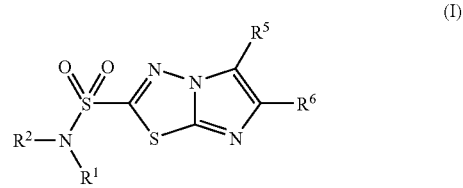

(I)

5 Claims, 9 Drawing Sheets a)

b)

c)

a)

b)

c)

IMIDAZO [2,1-B]-1,3,4-THIADIAZOLE SULFONAMIDES

FIELD OF THE INVENTION

This invention relates to sulfonamide compounds useful in the prevention of neuronal cell loss or in the treatment of nerve cell or axonal degradation.

BACKGROUND OF THE INVENTION

Various neurotrophins characterized by Neuronal Growth Factor (NGF), brain derived growth factor (BDNF), neurotrophin-3 (NT-3), and others (NT-4, CNTF, GDNF, IGF-1), have been identified as key survival factors for neurons. NGF plays a critical role in the development and maintenance of cholinergic forebrain neurons of the CNS and neurons of the peripheral nervous system (PNS); neurons of the PNS are characterized as small fiber sensory neurons associated with pain and temperature sensation, in addition to neurons of the sympathetic ganglia and dorsal root ganglia (SCGs and DRGs, respectively). BDNF plays a role in motor neuron survival. Both BDNF and NT-3 are expressed in the CNS and serve similar purposes in multiple subsets of cortical and hyppocampal neurons; neurons of the CNS are characterized by those found in the brain, spinal chord, and eye. The removal of these, and related trophic factors from in vitro cellular media results in the degradation of the axonal processes, leading to apoptosis of cultured neurons.

Localized tissue loss of NGF, or reduced axonal retrograde transport of NGF to the cell body, have been causally implicated in the development of peripheral neuropathies and neuropathic pain regularly observed in diabetes and HIV patients. Several double blind Phase II clinical trials have found that the systemic administration of recombinant human NGF (rhNGF) (U.S. Pat. No. 5,604,202) displayed beneficial effects on neuropathic pain, physiology, and cognition related to these diseases (Apfel, S. C. et. al. *JAMA*, 248(17), 2215–2221; Apfel, S. C. *Neurology* 51, 695–702, 1998; McAurthur, J. C. et al. *Neurology* 54, 1080–1088, 2000). Side effects related to rhNGF treatment included injection site pain, hyperalgesia, and other pain related symptoms. Despite these symptoms, a large number of patients continued rhNGF treatment after unblinding.

Various chemotherapeutic drugs such as Taxol™, cisplatin, vinblastine, and vincristine, cause dose dependent peripheral neuropathies, characterized by peripheral pain and loss of function. In many cases these neuropathies effectively limit the amount, and duration, of chemotherapy given to, patients. For example, upwards of 50% of patients receiving Taxol™ chemotherapy experience severe, and cumulative, peripheral neuropathies. The progression of the neuropathy necessitates the use of a dosing regime which is characterized by three cycles of fourteen days of Taxol™ treatment, followed by 14 days of recovery. Regression of the neuropathy is often observed between treatment cycles and following the final treatment. The degree and duration of recovery varies largely between patients. In addition to peripheral neuropathies, cisplatin treatment invariably results in some form of auditory loss, especially in children, due to neuronal damage in the inner ear, with minimal recovery of the neurons after completion of treatment.

SUMMARY OF THE INVENTION

The invention relates to imidazo[2,1-b] thiadiazole sulfonamides, which are useful in the treatment of neurodegenerative diseases of the CNS and/or PNS, for the inhibition of various serine-threonine protein kinases, phosphatases, CA, for inhibiting the degradation, dysfunction, or loss of neurons of the CNS and/or PNS, or enhancing the phenotype of neuronal cell types and preserving the axonal function of neuronal and synaptic processes of the CNS and/or of the PNS or altering signal transduction.

Also included are selected methods for the preparation of these compounds.

The imidazo[2,1-b]-1,3,4-thiadiazole sulfonamide derivatives and precursors of the present invention include compounds of the Formula I:

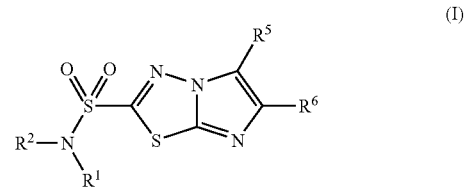

(I)

or pharmaceutically acceptable salts thereof wherein:

$R^1$ and $R^2$ are individually selected from the group consisting of H, lower alkyl, substituted lower alkyl, and fluoroalkyl;

$R^5$ is selected from the group consisting of H, halogen, cyano, azide, thiocyanate, formyl, lower alkyl, substituted lower alkyl, fluoroalkyl, aralkyl, substituted aralkyl, aryl, substituted aryl, heteroaryl, and substituted heteroaryl;

$R^6$ is selected from the group consisting of H, lower alkyl, substituted lower alkyl, fluoroalkyl, substituted fluoroalkyl, aryl, substituted aryl, heteroaryl, substituted heteroaryl, adamantly, coumarinyl, and substituted coumarinyl; or $R^6$ is represented by W:

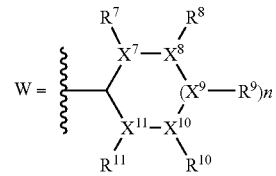

wherein:

n represents 0 or 1;

the ring system containing $X^7$–$X^{11}$ represents a 5 or 6 membered aromatic or heteroaromatic ring system, in which $X^7$–$X^{11}$ are independently selected from the group consisting of C, N, S, and O;

when any one of $X^7$–$X^{11}$ independently represents C, a respective $R^7$–$R^{11}$ is independently selected from the group consisting of:

a) H, halogen, nitro, cyano, lower alkyl, substituted lower alkyl, fluoroalkyl, aralkyl, substituted aralkyl, aryl, substituted aryl, heteroaryl, substituted heteroaryl, acyl, lower alkylcarbonyl, substituted lower alkylcarbonyl, arylcarbonyl, substituted arylcarbonyl, heteroarylcarbonyl, or substituted heteroarylcarbonyl;

b) $SO_2NR^{16}R^{17}$ wherein $R^{16}$ and $R^{17}$ are independently selected from the group consisting of lower alkyl, substituted lower alkyl, aralkyl, substituted aralkyl, heteroaralkyl, substituted heteroaralkyl aryl, substituted aryl, heteroaryl, and substituted heteroaryl, or wherein $R^{16}$ and $R^{17}$ are joined to form an alkyl, substituted alkyl, heteroalkyl, or substituted heteroalkyl ring system;

c) $SO_nR^{18}$ wherein n=0, 1 or 2, and wherein $R^{18}$ is selected from the group consisting of lower alkyl, substituted lower alkyl, aralkyl, substituted aralkyl, heteroaralkyl, substituted heteroaralkyl, aryl, substituted aryl, heteroaryl, and substituted heteroaryl;

d) $XR^{19}$ wherein X is defined as S or O, and $R^{19}$ is defined as alkyl, substituted alkyl, fluoroalkyl, aryl, substituted aryl, heteroaryl, substituted heteroaryl, acyl, lower alkylcarbonyl, substituted lower alkylcarbonyl, arylcarbonyl, substituted arylcarbonyl, heteroarylcarbonyl, substituted heteroarylcarbonyl, lower alkylaminocarbonyl, arylaminocarbonyl, or substituted arylaminocarbonyl;

e) $NR^{14}R^{15}$ wherein $R^{14}$ and $R^{15}$ are defined as lower alkyl joined to form an alkyl, substituted alkyl, heteroalkyl, or substituted heteroalkyl ring system; and f) $CO_2R^{20}$ wherein $R^{20}$ is defined as H, lower alkyl, substituted lower alkyl, aralkyl, substituted aralkyl, aryl, substituted aryl, heteroaryl, substituted heteroaryl, or $NR^{21}R^{22}$, wherein $R^{21}$ and $R^{22}$ are independently selected from the group consisting of lower alkyl, aralkyl, aryl;

wherein when any one of $X^7$–$X^{11}$ represents N, that nitrogen is attached to the adjacent atoms by either one single and one double bond (as in pyridinyl systems), or by two single bonds (as in indolyl or imidazolyl systems);

wherein when any one of $X^7$–$X^{11}$ represents N, and that nitrogen is attached to the adjacent atoms by one single and one double bond, the respective $R^7$–$R^{11}$ represents a lone pair;

when any one of $X^7$–$X^{11}$ represents N, and that nitrogen is attached to the adjacent atoms by two single bonds (as in indolyl or imidazolyl systems), the respective $R^7$–$R^{11}$ is selected from the group consisting of H, lower alkyl, substituted lower alkyl, aralkyl, substituted aralkyl, aryl, substituted aryl, heteroaryl, substituted heteroaryl, $SO_2R^{18}$, wherein $R^{18}$ is defined as in c), $COR^{18}$, wherein $R^{18}$ is defined as in c);

when n=0, $R^7$ and $R^8$, or $R^8$ and $R^9$ are combined to form a fused 5, 6, or 7 membered alkyl, substituted alkyl, heteroalky, substituted heteroalkyl, heteroaralkyl, substituted heteroaralkyl, aryl, substituted aryl, heteroaryl, or heteroaryl ring system;

when n=1 and $X^9$ represents C, $R^7$ and $R^8$, or $R^8$ and $R^{10}$ are combined to form a fused 5, 6, or 7 membered alkyl, substituted alkyl, heteroalky, substituted heteroalkyl, aryl, substituted aryl, or heteroaryl ring system; and any one of $R^7$–$R^{11}$ represents a lone pair when the respective $X^7$–$X^{11}$ represents S or O;

with the proviso that compounds 1, 4, 10, 14, 20, 60, 72, 105, 109, 111, 114, 124, 126, 127, 133, and 153 are excluded.

The invention relates to sulfonamide compounds of Formula I and the use of compounds of Formula I (including those noted within the proviso excluding the actual compounds themselves) for the prevention of neuronal cell loss or the treatment of nerve cell or axonal degradation, in either the central or peripheral nervous systems (CNS and PNS, respectively). The invention is useful in prevention or treatment of conditions leading to or resulting from such diseases as Alzheimer's, Huntington's, Parkinson's, muscular dystrophy, diabetes, HIV, from ischemic insults such as stroke in the brain (CNS), retinal ganglion loss following acute ocular stroke or hypertension as in glaucoma, and from infection by viruses such as Hepatitis C and Herpes Simplex. Further, the invention provides compounds for use in treatment of neuropathies resulting from chemotherapeutic agents used in the treatment of HIV and proliferative disease such as cancer, for the treatment of inflammatory diseases.

In order to identify compounds which mimic the positive effects of NGF on peripheral neurons, but which lack the inherent difficulties associated with the use of recombinant human proteins and the rhNGF related hyperalgesia, we have developed several in vitro screens using a variety of neurotoxic insults. PNS neurons such as the superior cervical ganglion (SCG) and dorsal root ganglion (DRG) undergo apoptosis when subjected to NGF withdrawal. Treatment with chemotherapeutic agents such as Taxol™, cisplatin, vinblastine, vincristine, and anti-viral agents such as D4T, also induce neuronal apoptosis. Similarly, neurons of the CNS, such as cortical neurons, are sensitive to various neurotoxic agents such as β-amyloid, NMDA, osmotic shock, Taxol™ and cisplatin. Additionally, retinal ganglion (RG) neurons subjected to hypoxia undergo apoptosis. Compounds which protect neurons from neurotoxic insults such as those mentioned above will be useful in the treatment of the peripheral neuropathies observed in diseases such as diabetes and HIV. Compounds which protect neurons from chemotherapeutic toxicity, if given prior to, concurrently with, or following, chemotherapeutic treatment will allow for the use of increasing concentrations of chemotherapeutics and/or extend the duration of chemotherapy treatments. Alternatively, enhanced recovery will be observed if such compounds are given during the recovery stages, and post treatment. These compounds will also be useful in the treatment of neurodegenerative diseases of the CNS, such as AD, PD, HD, stroke, MS, macular degeneration, glaucoma, optical stroke and retinal degeneration, and the like.

We have shown that compounds of Formula I protect SCG neurons from several neurotoxic insults, including NGF withdrawal and treatment with chemotherapeutics such as Taxol™, cisplatin, and vincristine. Compounds of Formula I also protect cortical motor neurons from malonate induced death.

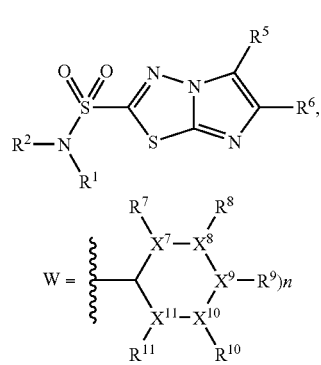

When such agents are administered to mice treated with Taxol™, either before, during or after a two week dosing period, marked improvements are observed in the animal's general health, weight gain, and gait, as compared to animals treated with Taxol™ alone. Additionally, compounds of Formula I aid in the regeneration of neurons damaged as a result of sciatic nerve crush.

Selected examples from Formula I have been previously described. Their uses include anti-bacterial agents (Gadad, A. K. *Eur J. Med. Chem.*, 35(9), 853–857, 2000), anti-proliferative agents (Gadad, A. K. *India. Arzneim.-Forsch.*, 49(10), 858–863, 1999), and as carbonic anhydrase (CA) inhibitors (Barnish, I. T., et. al. *J. Med. Chem.*, 23(2), 117–121, 1980; Barnish, I. T. et. al GB 1464259, abandoned; Supuran, C, T. *Met.-Based Drugs* 2(6), 331–336, 1995—Co (II), Cu (II), Zn(II) complexes of compound 1). Barnish et al. demonstrated that certain compounds reduced the number and intensity of electroshock induced seizures in rats. This anti-seizure activity was linked to increased cerebral blood flow, attributed to the ability of these compounds to inhibit CA. No direct evidence of neuronal protection as a result of these compounds has been previously demonstrated in vitro or in vivo (ie. histology, neuronal cell count, etc.).

We have found that various aryl sulfonamide CA inhibitors do not protect SCG neurons from apoptosis. These finding indicate that the neuroprotection mediated by compounds represented by Formula I is independent of their CA activity. Additionally, we have prepared several synthetic derivatives of represented by Formula I which display reduced CA inhibition inhibit CA, while retaining their neuroprotective capabilities.

The invention relates to synthetic routes for preparation of compounds represented by Formula I, and methods for the functionalization of compounds represented by Formula I.

DETAILED DESCRIPTION

Figure 1:
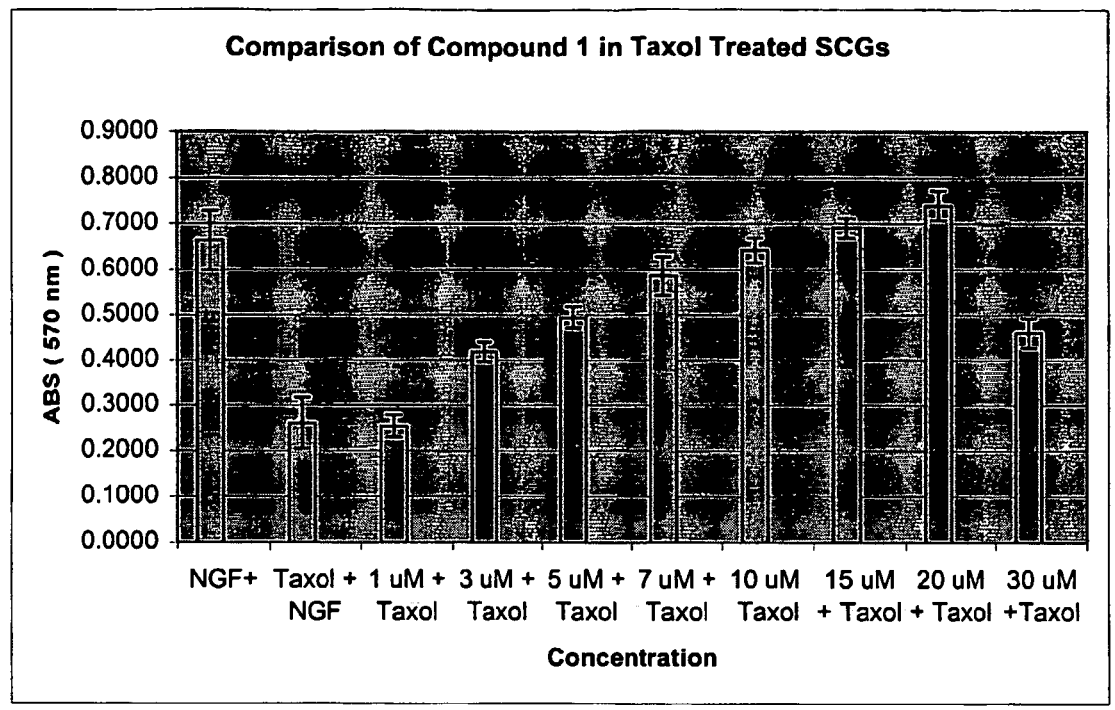
FIG. 1 illustrates the protection of SCG neurons from Taxol™ induced killing provided by Compound 1 (AEG 3482).

The compounds represented by Formula (I) may be referred to herein interchangeably as as Compound (I). Compounds referred to herein by number (such as compound 1 or compound 76) refer to the compounds outlined as Examples 1 to 153.

In the definitions of the groups of Formula I, lower alkyl means a straight-chain or branched alkyl group having 1 to 8 carbon atoms, such as methyl, ethyl, propyl, iso-propyl, n-butyl, iso-butyl, sec-butyl, tert-butyl, pentyl, iso-amyl, neopentyl, 1-ethylpropyl, hexyl, and octyl. The lower alkyl moiety of lower alkoxy, lower alkylsulfonyl, lower alkoxylcarbonyl, lower alkylaminocarbonyl has the same meaning as lower alkyl defined above. The acyl moiety of the acyl and the acyloxy group means a straight-chain or branched alkanoyl group having 1 to 6 carbon atoms, such as formyl, acetyl, propanoyl, butyryl, valeryl, pivaloyl and hexanoyl, and arylcarbonyl group described below, or a heteroarylcarbonyl group described below. The aryl moiety of the aryl, the arylcarbonyl and arylaminocarbonyl groups means a group having 6 to 16 carbon atoms such as phenyl, biphenyl, naphthyl, or pyrenyl. The heteroaryl moiety of the heteroaryl and the heteroarylcarbonyl groups contain at least one hetero atom from O, N, and S, such as pyridyl, pyrimidyl, pyrroleyl, furyl, benzofuryl, thienyl, benzothienyl, imidazolyl, triazolyl, quinolyl, iso-quinolyl, benzoimidazolyl, thiazolyl, benzothiazolyl, oxazolyl, and indolyl. The aralkyl moiety of the aralkyl and the aralkyloxy groups having 7 to 15 carbon atoms, such as benzyl, phenethyl, benzhydryl, and naphthylmethyl. The heteroaralkyl moiety of the heteroaralkyl and the heteroaralkyloxy groups having 7 to 15 carbon such as pyridylmethyl, quinolinylmethyl, and iso-quinolinylmethyl. The substituted lower alkyl group has 1 to 3 independently-substitutuents, such as hydroxyl, lower alkyloxy, carboxyl, lower alkylcarbonyl, nitro, amino, mono- or di-lower alkylamino, dioxolane, dioxane, dithiolane, and dithione. The lower alkyl moiety of the substituted lower alkyl, and the lower alkyl moeity of the lower alkoxy, the lower alkoxycarbonyl, and the mono- and di-lower alkylamino in the substituents of the substituted lower alkyl group have the same meaning as lower alkyl defined above. The substituted aryl, the substituted heteroaryl, the substituted aralkyl, and the substituted heteroaralkyl groups each has 1 to 5 independently-selected substituents, such as lower alkyl, hydroxy, lower alkoxy, carboxy, lower alkoxycarbonyl, nitro, amino, mono or di-lower alkylamino, azido, and halogen. The lower alkyl moiety of the lower alkyl, the lower alkoxy, the lower alkylamino, and the mono- and di-lower alkylamino groups amoung the susbtituents has the same meaning as lower alkyl defined above. The heterocyclic group formed with a nitrogen atom includes rings such as pyrrolyl, piperidinyl, piperidino, morpholinyl, morpholino, thiomorpholino, N-methylpiperazinyl, indolyl, and isoindolyl. The cycloalkyl moeity means a cycloalkyl group of the indicated number of carbon atoms, containing one or more rings anywhere in the structure, such as cycloalkyl groups include cyclopropyl, cyclopropylmethyl, cyclobutyl, cyclopentyl, cyclohexyl, 2-norbornyl, 1-adamantyl and the like. The fluoroalkyl moiety means a lower fluoroalkyl group in which one or more hydrogens of the corresponding lower alkyl group, as defined above, is replaced by a fluorine atom, such as $CH_2F$, $CHF_2$, $CF_3$, $CH_2CF_3$, and $CH_2CH_2CF_3$.

Some of the compounds described herein contain one or more chiral centres and may thus give rise to diastereomers and optical isomers. The present invention is meant to comprehend such possible diastereomers as well as their racemic, resolved and enantiomerically pure forms, and pharmaceutically acceptable salts thereof.

The term "subject" or "patient" as used herein may refer to mammals including humans, primates, horses, cows, pigs, sheep, goats, dogs, cats and rodents.

The pharmaceutical compositions of the invention are administered to subjects in effective amounts. An effective amount means that amount necessary to delay the onset of, inhibit the progression of, halt altogether the onset or progression of or diagnose the particular condition or symptoms of the particular condition being treated. In general, an effective amount for treating a neurological disorder is that amount necessary to affect any symptom or indicator of the condition In general, an effective amount for treating neuropathies and neuropathic pain will be that amount necessary to favorably affect mammalian cancer cell proliferation in situ. When administered to a subject, effective amounts will depend, of course, on the particular condition being treated; the severity of the condition; individual patient parameters including age, physical condition, size and weight; concurrent treatment; frequency of treatment; and the mode of administration. These factors are well known to those of ordinary skill in the art and can be addressed with no more than routine experimentation. It is preferred generally that a maximum dose be used, that is, the highest safe dose according to sound medical judgment.

A variety of administration routes are available. The particular mode selected will depend, of course, upon the particular condition being treated, the particular drug selected, the severity of the condition being treated and the dosage required for therapeutic efficacy. The methods of this invention, generally speaking, may be practiced using any mode of administration that is medically acceptable, meaning any mode that produces effective levels of the active compounds without causing clinically unacceptable adverse effects. Such modes of administration include oral, rectal, sublingual, topical, nasal, transdermal, intradermal or parenteral routes. The term "parenteral" includes subcutaneous, intravenous, intramuscular, or infusion. Oral routes are preferred.

Dosage may be adjusted appropriately to achieve desired drug levels, locally or systemically. Generally, daily oral doses of active compounds will be from about 0.01 mg/kg per day to 1000 mg/kg per day. It is expected that IV doses in the range of about 1 to 1000 mg/m2 per day will be effective. In the event that the response in a subject is insufficient at such doses, even higher doses (or effective higher doses by a different, more localized delivery route) may be employed to the extent that patient tolerance permits.

The compositions may conveniently be presented in unit dosage form and may be prepared by any of the methods well known in the art of pharmacy. All methods include the step of bringing the conjugates of the invention into association with a carrier that constitutes one or more accessory ingredients. In general, the compositions are prepared by uniformly and intimately bringing the compounds into association with a liquid carrier, a finely divided solid carrier, or both, and then, if necessary, shaping the product.

Compositions suitable for oral administration may be presented as discrete units such as capsules, cachets, tablets, or lozenges, each containing a predetermined amount of the active compound. Other compositions include suspensions in aqueous liquors or non-aqueous liquids such as a syrup, an elixir, or an emulsion.

Other delivery systems can include time-release, delayed release or sustained release delivery systems. Such systems can avoid repeated administrations of the active compounds of the invention, increasing convenience to the subject and the physician. Many types of release delivery systems are available and known to those of ordinary skill in the art. They include polymer based systems such as polylactic and polyglycolic acid, polyanhydrides and polycaprolactone; nonpolymer systems that are lipids including sterols such as cholesterol, cholesterol esters and fatty acids or neutral fats such as mono-, di and triglycerides; hydrogel release systems; silastic systems; peptide based systems; wax coatings, compressed tablets using conventional binders and excipients, partially fused implants and the like. In addition, a pump-based hardware delivery system can be used, some of which are adapted for implantation.

A long-term sustained release implant also may be used. "Long-term" release, as used herein, means that the implant is constructed and arranged to deliver therapeutic levels of the active ingredient for at least 30 days, and preferably 60 days. Long-term sustained release implants are well known to those of ordinary skill in the art and include some of the release systems described above. Such implants can be particularly useful in treating solid tumors by placing the implant near or directly within the tumor, thereby affecting localized, high-doses of the compounds of the invention.

When administered, the Formulations of the invention are applied in pharmaceutically acceptable compositions. Such preparations may routinely contain salts, buffering agents, preservatives, compatible carriers, and optionally other therapeutic ingredients. When used in medicine the salts should be pharmaceutically acceptable, but non-pharmaceutically acceptable salts may conveniently be used to prepare pharmaceutically acceptable salts thereof and are not excluded from the scope of the invention. Such salts include, but are not limited to, those prepared from the following acids: hydrochloric, hydrobromic, sulphuric, nitric, phosphoric, maleic, acetic, salicylic, p-toluenesulfonic, tartaric, citric, methane sulfonic, formic, malonic, succinic, naphthalene-2-sulfonic, benzene sulfonic, and the like. Also, pharmaceutically acceptable salts can be prepared as alkaline metal or alkaline earth salts, such as sodium, potassium or calcium salts.

Suitable buffering agents include: phosphate buffers, acetic acid and a salt (1–2% W/V); citric acid and a salt (1–3% W/V); and phosphoric acid and a salt (0.8–2% W/V), as well as others known in the art.

Suitable preservatives include benzalkonium chloride (0.003–0.03% W/V); chlorobutanol (0.3–0.9% W/V); parabens (0.01–0.25% W/V) and thimerosal (0.004–0.02% W/V), as well as others known in the art.

Suitable carriers are pharmaceutically acceptable carriers. The term pharmaceutically acceptable carrier means one or more compatible solid or liquid filler, dilutants or encapsulating substances that are suitable for administration to a human or other animal. The term "carrier" denotes an organic or inorganic ingredient, natural or synthetic, with which the active ingredient is combined to facilitate the application. The components of the pharmaceutical compositions are capable of being commingled with the molecules of the present invention, and with each other, in a manner such that there is no interaction which would substantially impair the desired pharmaceutical efficacy. Carrier Formulations suitable for oral, subcutaneous, intravenous, and intramuscular administration etc., are those which are known in the art.

The compounds of the invention may be delivered with other therapeutic agents. The invention additionally includes co-administration of compound I of the invention with other compounds known to be useful in treating neurodegenerative diseases, typified by but not limited to, acetylcholinesterase inhibitors for treating AD, such as tacrine, doneprizil, and rivastigmin, and L-dopa for treating PD, and ACE inhibitors and insulin for the treatment of diabetes.

In the case of peripheral neuropathy induced by a toxic agent, compound I would be delivered separately before, simultaneously with (ie. in the form of anti-cancer coctails, see below), or after exposure to the toxic agent. Preferably, compound I and the chemotherapeutic agent are each administered at effective time intervals, during an overlapping period of treatment in order to prevent or restore at least a portion of the neurological function destroyed by the neurotoxic or chemotherapeutic agent. The chemotherapeutic can be any chemotherapeutic agent that causes neurotoxicity, such as dideoxyinosine, deoxy cytizine, D4T, cisplatin, etoposide, vincristine, epithilone or its derivatives, or Taxol™/Taxoter™ and derivatives thereof, which are representative of the classes of agents induce neuropathies.

By "toxic agent" or "neurotixic agent" is meant a substance that through its chemical action injures, impairs, or inhibits the activity of a component of the nervous system. The list of neurotoxic agents that cause neuropathies is lengthy (see a list of candidate agents provided in Table 1). Such neurotoxic agents include, but are not limited to, neoplastic agents such as vincristine, vinblastine, cisplatin, Taxol™, or dideoxy-compounds, eg., dideoxyinosine; alcohol; metals; industrial toxins involved in occupational or environmental exposure; contaminants in food or medicinals; or over-doses of vitamines or therapeutic drugs, eg. Antibiotics such as penicillin or chloramphenicol, or megadoses of vitamins A, D, or B6.

TABLE 1

Neurotoxic Agents

| AGENT | ACTIVITY |
|---|---|
| acetazolimide | diuretic |
| acrylamide | flocculant, grouting agent |
| adriamycin | antineoplastic |
| alcohol (ie. ethanol) | solvent, recreational drug |
| almitine | respiratory stimulant |
| amiodarone | antiarrthymic |
| amphotericin | antimicrobial |
| arsenic | herbicide, insecticide |
| aurothioglucose | antirheumatic |
| barbiturates | anticonvulsive, sedative |
| buckthorn | toxic berry |
| carbamates | insecticide |
| carbon disulfide | industrial applications |
| chloramphenicol | antibacterial |
| chloroquine | antimalarial |
| chlorestyramine | antihyperlipoproteinemic |
| cisplatin | antineoplastic |
| clioquinol | amebicide, antibacterial |
| colestipol | antihyperlipoproteinemic |
| colchicine | gout suppressant |
| colistin | antimicrobial |

TABLE 1-continued

Neurotoxic Agents

| AGENT | ACTIVITY |
|---|---|
| cycloserine | antibacterial |
| cytarabine | antineoplastic |
| dapsone | dermatological including leprosy |
| dideoxycytidine | anatineoplastic |
| dideoxyinosine | antineoplastic |
| dideoxythymidine | antiviral |
| disulfiram | antialcohol |
| doxorubicin | antineoplastic |
| ethambutol | antibacterial |
| ethionamide | antibacterial |
| glutethimide | sedative, hypnotic |
| gold | antirheumatic |
| hexacarbons | solvents |
| hormonal contraceptives | |
| hexamethylolmelamine | fireproofing, crease proofing |
| hydralazine | antihypertensive |
| hydroxychloroquine | antirheumatic |
| imipramine | antidepressant |
| indomethacin | anti-inflammatory |
| inorganic lead | toxic metal in paint, etc. |
| iso-niazid | antituberculousis |
| lithium | antidepressant |
| methylmercury | industrial waste |
| metformin | antidiabetic |
| methylhydrazine | synthetic intermediate |
| metronidazole | antiprotozoal |
| misonidazole | radiosensitizer |
| nitrofurantoin | urinary antiseptic |
| nitrogen mustard | antineoplastic, nerve gas |
| nitous oxide | anesthetic |
| organophosphates | insecticides |
| ospolot | anticonvulsant |
| penicillin | antibacterial |
| perhexiline | antiarrhythmic |
| perhexiline maleate | antiarrythmic |
| phenytoin | anticonvulsant |
| platnim | drug component |
| primidone | anticonvulsant |
| procarbazine | antineoplastic |
| pyridoxine | vitamin B6 |
| sodium cyanate | antisickling |
| streptomycin | antimicrobial |
| sulphonamides | antimicrobial |
| suramin | anteneoplastic |
| tamoxifen | antineoplastic |
| Taxol ™ | antineoplastic |
| thalidomide | antileprous |
| thallium | rat poison |
| triamterene | diuretic |
| trimethyltin | toxic metal |
| L-trypophan | health food additive |
| vincristine | antineoplastic |
| vinblastine | antineoplastic |
| vindesine | antineoplastic |
| vitamine A or D | mega doses |

Several neurotoxic agents and protocols may be used to induce apoptosis in SCG neurons. Several of these insults include the withdrawal of trophic support (for example NGF), treatment with neurotoxic chemotherapeutics such as Taxol™, cisplatin, vincristine, or vinblastine, and treatment with neurotoxic anti-virals such as D4T. Selected compounds represented by Formula I have been found to inhibit apoptosis induced by the above insults.

Neurotrophins are critical to the growth, development, and survival of small fiber neurons of the PNS. SCG neurons are neurons of the PNS that undergo apoptosis upon NGF withdrawal. In a typical experiment SCG neurons are cultured in the presence of NGF, which induces survival and neurite out-growth. After 5 days the NGF is removed by either the addition of anti-NGF polyclonal antibody (Sigma) or by repeated washings (4 times) with NGF free media, resulting in the apoptosis of up to 90% of the neurons after 48 hours, as measured by MTS staining. The addition of selected compounds of Formula I to the final cellular media provides upwards of 100% protection, at drug concentrations ranging from 3 to 50 μM (see Example 154).

Taxol™ is regularly used in breast cancer chemotherapy. In cancer cells Taxol™ binds to the cyto-skeletal protein tubulin, thereby inhibiting normal microtubular assembly and inducing cellular apoptosis. Despite its potency as an anti-tumour agent, Taxol™ is also toxic to neurons, inducing dose limiting peripheral neuropathies. The addition of Taxol™ (100 ng/mL) to cultured SCG neurons induces the degradation or loss of upwards of 80% of the neurons. The addition of selected compounds of Formula I to the cellular media, concurrently with Taxol™, protects upwards of 100% of the neurons, at drug concentrations ranging from 3 to 50 μM (see Example 155 and FIG. 1).

The mechanism of Cisplatin's anti-cancer action is not fully understood, but is believed to involve DNA binding and cleavage. Cisplatin is highly toxic to neurons. The addition of cisplatin (3 μg/mL) to cultured SCG neurons induces apoptosis of upwards of 80% of the neurons. The addition of selected compounds of Formula I to the cellular media, concurrently with cisplatin, protects upwards of 100% of the neurons, at drug concentrations ranging from 1 to 50 μM (see Example 156).

Similarly, vincristine and vinblastine are commonly used anti-tumour agents whose mode of action involve tubulin binding. As above, the addition of vincristine (100 ng/mL) to cultured SCG neurons induces apoptosis of upwards of 80% of the neurons. The addition of selected compounds of Formula I to the cellular media, concurrently with vincristine, protects upwards of 100% of the neurons, at drug concentrations ranging from 1 to 50 μM (see Example 157).

Various neurodegenerative diseases are related to the cellular or functional loss of motor neurons of the CNS and PNS. ALS is a characterized by motor neuron loss as a result of mitochondrial dysfunction, which can be mimicked in culture by the addition of malonate to organotypic brain slices. P1 rat motor cortex brain slices were cultured for 2 weeks prior to drug and malonate addition. After an additional two weeks the slices were fixed and stained with SMI-32 antibody which selectively stains motor neurons found in layer V of the cortex. Compound 91 protected upwards of 80% of these labeled motor neurons at a drug concentration of 1 μM (Example 158).

Taken together, compound of Formula I display remarkable neuroprotective capabilities, against a wide range of insults in both the CNS and the PNS. One of the intended uses of these agent is in the conjugation with chemotherapeutic agents. If compounds represented by Formula I were to protect cancer cells from the same chemotherapeutic agents, it would have limited value. Two pieces of evidence suggest these compounds do not protect cancer cells from chemotherapeutics. Selected compounds represented by Formula I have previously been shown to be anit-proliferative (Gadad, A. K. *India. Arzneim.-Forsch.*, 49(10), 858–863, 1999), suggesting these compounds will be beneficial when used in conjunction with other chemotherapeutic agents. Additionally, we have shown that compound 1 displays no protection when human ovarian carcinoma cells (OV2008) and human lung carcinoma cells (H460) were treated with Taxol™ and/or cisplatin (see Example 159 and FIG. 3).

Compound 1 and several of its derivatives have been reported to be potent inhibitors of carbonic anhydrase (CA) (Barnish, I. T., et. al. *J. Med. Chem.*, 23(2), 117–121, 1980). CA plays an important role in maintaining both intra- and extra-cellular pH levels. In an effort to determine whether the neuroprotective profile of compound 1 was due to CA inhibition, a number of well-known, cell permeable, aryl sulfonamide CA inhibitors were evaluated against the Taxol™ killing of SCGs. Dorzolamide, (Ponticello, G. S., et. al *J. Med Chem.*, 1987, 30, 591) aminobenzolamide N-acetylaminobenzolamide, acetazolamide, and methazolamide (see Marten, T. H. *J. Glaucoma*, 1995, 4, 49) all failed to significantly inhibit Taxol™ induced killing of SCGs at concentrations as high as 50 μM. Additionally, the ability of compounds represented by Formula I to inhibit CAII varied greatly depending upon the substitution patterns found on the sulfonamide or the C6 position (see Example 163). For example, compound 137 is the N-methyl derivative of compound 1, compound 137, displays a 100 fold decrease in CAII activity (CAII(50) 2.06 μM and 250 nM, respectively) while retaining a similar IC(50) against Taxol (7 μM each). Similarly, compound 77 is a poor CAII inhibitor (IC(50) 6.3 μM), but displays a more potent against Taxol killing of SCGs (IC (50) 2 μM). Based on these results it is clear that although compounds of Formula I are known CA inhibitors, the primary mechanism by which it is protecting neurons appears to be independent of CA inhibition.

Adenovirus overexpression of Erk1 and Erk2, two members of the MAP kinase family of signaling proteins, have been shown to stimulate neuronal out-growth and the formation of new synaptic connections in primary neurons of the PNS and CNS. Additionally, the Erks protect cultured neurons from a number of insults including neurotrophin withdrawal (Bonni, A., et al., *Science*, 1999, 286, 1358–1362). A dramatic increase in Erk activity was observed in both PC12 cells and in primary cultures of sympathetic neurons when treated with compound 1. The activity of Akt, however, remained unchanged when both PC12 cells and SCGs were treated with compound 1. Akt is activated by NGF and has been demonstrated to be neuroprotective in both PNS and CNS neurons. Compound 1, therefore, protects neurons by activating a subset of NGF-stimulated signaling pathways.

Taxol™ commonly causes dose dependent peripheral neuropathies during cancer treatment. When treated with Taxol™ (9 mg/kg in Cremophor EL and ethanol) twice weekly for 3 weeks, Sprague Dawley rats displayed acute symptoms of chemotoxicity, characterized by reduced appetite, weight loss, gait disturbance (a general marker of Taxol™ induced peripheral neuropathy), and general poor health (see Example 160). For example, over a thirteen day period control animals gained an average of 50 g, whereas the Taxol™ treated animals displayed no weight gain (see FIG. 4). All of the Taxol™ treated animals developed peripheral neuropathies, characterized by 'tip toe walking'. The extent of this neuropathy was analyzed by quantifying the refracted light captured by a video camera as the animals walked over a glass plate. This data was analyzed by Northern Eclipse software. The Taxol™ treated animals displayed a 46% reduction in foot-pad contact with the glass plate, as compared to control animals (see Example 160).

When compound 1 (5 mg/kg) was given with Taxol™ (9 mg/kg) on a bi-weekly schedule, the animals displayed greatly improved health. This was characterized by normal weight gain, as compared to control (FIG. 4), and a reduction in the severity of the peripheral neuropathies; a 23% loss in foot pad contact was observed, as compared to a 46% loss in the animals treated with Taxol™ alone (see Example 160 and FIGS. 5 and 6). No acute signs of toxicity were observed in animals in acute toxicity studies with compound 1 alone (1, 5, and 10 mg/kg for 3 weeks).

The sciatic nerve crush model is a representative model of axonal repair and regeneration. The sciatic nerve is physically crushed with forceps at the mid-thigh; only the right leg is injured, the left leg serving as a control. The axons die from the crush point to their point of innervation. Functional loss of the axons is rapidly observed as the animals drag their right leg and the toes of the right leg no longer spread. Recovery is observed in approximately 28 days as the animals regain use of their right leg. More quantitative measurements of recovery include toe spread measurements between the digits 1 and 5 and digits 2 and 4, gait analysis and electrical conductivity from the toes to the injury site (see Example 161).

Rats were subjected to the crush injury and treated with either vehicle control or compounds 1,76 or 111 (1 and 10 mg/kg). Functional recovery was measured as above and improved recovery was observed when the animals were treated with compound. For example, increase toe spread was observed for those animal treated with compound (see FIG. 7).

Various diseases which result in loss of vision are related to increased inter-ocular pressure and ocular stroke or ischemia. Loss of the retinal ganglion (RG) occur during ischemic insult and in diseases such as diabetes and glaucoma. A model of inter-ocular ischemia involves an invasive increase in ocular pressure which results in the collapse of the central retinal artery. Retinal isehemia is confirmed by whitening of the iris and loss of red reflex. The inter-ocular pressure is normalized after 30 minutes. This procedure is performed on the right eye and the left eye serves as a control. Compound was given either by intra-vitrial injection or via SC injections at 10 mg/kg (see Example 162).

The health of the RG neurons was assessed by means of histological staining of retinal slices and electro-retinogram (ERG) recordings. Histology of the control animals showed almost complete loss of the RG layer, where as animals treated with compound 1 showed healthy RG layers. Similarly, significant improvements were observed in the ERG for those animals treated with compound verses vehicle control animals (see FIG. 8). This protection was observed for both the animals which received intra-vitrial injections and those that were treated systemically (SC).

Alzheimer's disease is one of the biggest unmet medical needs in neurology. One of the main areas of AD research has been deposition and neurotoxicity of amyloid beta peptide fragments. Amyloid peptides are potently toxic to cortical neurons and protection of the cortical neurons would be a very desirable therapeutic target. We establish mixed neuronal/glial cortical cultures from postnatal rat pups. Amyloid beta peptides are potently toxic to neurons in these cultures. Exposure to 10 uM 25–35 amyloid beta increased the number of apoptotic cells compared to control. Compound 76 prevented the appearance of annexinV positive cells indicating that it protected in vitro against the amyloid beta peptide.

For any of the compounds having the structure of Formula I which bear similarity to those known in the art, the use of these compounds for treatment and/or prevention of neurological disorders, cancer, inflammation, or symptoms related thereto are encompassed by the invention.

Examples of Formula I are provided below in Table 2. These compounds are referred to throughout the disclosure as their corresponding example number.

TABLE 2

Compounds

| Example | STRUCTURE |
|---------|-----------|
| 1 | 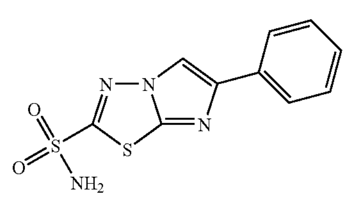 |
| 2 | 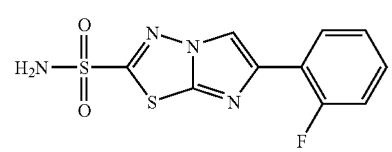 |
| 3 | 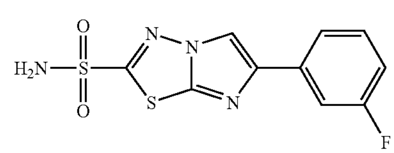 |

TABLE 2-continued

Compounds

| Example | STRUCTURE |
|---|---|
| 4 | 2-sulfamoyl-6-(4-fluorophenyl)imidazo[2,1-b][1,3,4]thiadiazole |
| 5 | 2-sulfamoyl-6-(3,4-difluorophenyl)imidazo[2,1-b][1,3,4]thiadiazole |
| 6 | 2-sulfamoyl-6-(pentafluorophenyl)imidazo[2,1-b][1,3,4]thiadiazole |
| 7 | 2-sulfamoyl-6-(2,3,5,6-tetrafluoro-4-(ethylthio)phenyl)imidazo[2,1-b][1,3,4]thiadiazole |
| 8 | 2-sulfamoyl-6-(2,3,5,6-tetrafluoro-4-(benzylthio)phenyl)imidazo[2,1-b][1,3,4]thiadiazole |
| 9 | 2-sulfamoyl-6-(2,3,5,6-tetrafluoro-4-morpholinophenyl)imidazo[2,1-b][1,3,4]thiadiazole |
| 10 | 2-sulfamoyl-6-(4-chlorophenyl)imidazo[2,1-b][1,3,4]thiadiazole |

TABLE 2-continued

Compounds

| Example | STRUCTURE |
|---|---|
| 11 | 6-(3,4-dichlorophenyl)-imidazo[2,1-b][1,3,4]thiadiazole-2-sulfonamide |
| 12 | 6-(2,3,4-trichlorophenyl)-imidazo[2,1-b][1,3,4]thiadiazole-2-sulfonamide |
| 13 | 6-(3-bromophenyl)-imidazo[2,1-b][1,3,4]thiadiazole-2-sulfonamide |
| 14 | 6-(4-bromophenyl)-imidazo[2,1-b][1,3,4]thiadiazole-2-sulfonamide |
| 15 | 6-(2-methoxyphenyl)-imidazo[2,1-b][1,3,4]thiadiazole-2-sulfonamide |
| 16 | 6-(3-methoxyphenyl)-imidazo[2,1-b][1,3,4]thiadiazole-2-sulfonamide |
| 17 | 6-(4-methoxyphenyl)-imidazo[2,1-b][1,3,4]thiadiazole-2-sulfonamide |
| 18 | 6-(2,5-dimethoxyphenyl)-imidazo[2,1-b][1,3,4]thiadiazole-2-sulfonamide |

TABLE 2-continued

Compounds

| Example | STRUCTURE |
|---|---|
| 19 | 2-sulfamoyl-6-(2,4-dimethoxyphenyl)imidazo[2,1-b][1,3,4]thiadiazole · HBr |
| 20 | 2-sulfamoyl-6-(benzo[1,3]dioxol-5-yl)imidazo[2,1-b][1,3,4]thiadiazole |
| 21 | 2-sulfamoyl-6-(3,4-dihydro-2H-1,5-benzodioxepin-7-yl)imidazo[2,1-b][1,3,4]thiadiazole |
| 22 | 2-sulfamoyl-6-(3,4-dihydroxyphenyl)imidazo[2,1-b][1,3,4]thiadiazole |
| 23 | 2-sulfamoyl-6-(spiro[cyclohexane-1,2'-benzo[1,3]dioxol]-5'-yl)imidazo[2,1-b][1,3,4]thiadiazole |
| 24 | 2-sulfamoyl-6-(3-trifluoromethoxyphenyl)imidazo[2,1-b][1,3,4]thiadiazole |
| 25 | 2-sulfamoyl-6-(4-trifluoromethoxyphenyl)imidazo[2,1-b][1,3,4]thiadiazole |

TABLE 2-continued

Compounds

| Example | STRUCTURE |
|---|---|
| 26 | Sulfamoyl-imidazo-thiadiazole linked to 4-(2-hydroxyethoxy)phenyl |
| 27 | Sulfamoyl-imidazo-thiadiazole linked to 4-(2-acetoxyethoxy)phenyl |
| 28 | Sulfamoyl-imidazo-thiadiazole linked to 4-(2-azidoethoxy)phenyl |
| 29 | Sulfamoyl-imidazo-thiadiazole linked to 4-(3,3,3-trifluoropropoxy)phenyl |
| 30 | Sulfamoyl-imidazo-thiadiazole linked to 4-(2-(2-methoxyethoxy)ethoxy)phenyl |
| 31 | Sulfamoyl-imidazo-thiadiazole linked to 4-(2-(benzyloxy)ethoxy)phenyl |
| 32 | Sulfamoyl-imidazo-thiadiazole linked to 4-(3-(benzyloxy)propoxy)phenyl |

TABLE 2-continued

Compounds

| Example | STRUCTURE |
|---------|-----------|
| 33 | (structure: sulfamoyl-imidazo-thiadiazole with phenyl-O-ethyl-morpholine, 2 CH₃SO₃H) |
| 34 | (structure: sulfamoyl-imidazo-thiadiazole with 3-methoxy-4-(2-hydroxyethoxy)phenyl) |
| 35 | (structure: sulfamoyl-imidazo-thiadiazole with 3-methoxy-4-(2-benzyloxyethoxy)phenyl) |
| 36 | (structure: sulfamoyl-imidazo-thiadiazole with 3-methoxy-4-(3-benzyloxypropoxy)phenyl) |
| 37 | (structure: sulfamoyl-imidazo-thiadiazole with 3-nitrophenyl) |
| 38 | (structure: sulfamoyl-imidazo-thiadiazole with 4-chloro-3-nitrophenyl) |

TABLE 2-continued

Compounds

| Example | STRUCTURE |
|---|---|
| 39 | |
| 40 | |
| 41 | |
| 42 | |
| 43 | |
| 44 | |
| 45 | |

TABLE 2-continued

Compounds

| Example | STRUCTURE |
|---------|-----------|
| 46 | (imidazo[2,1-b][1,3,4]thiadiazole-2-sulfonamide with 6-(4-pentylphenyl) substituent) |
| 47 | (imidazo[2,1-b][1,3,4]thiadiazole-2-sulfonamide with 6-(4-methylphenyl) substituent) |
| 48 | (imidazo[2,1-b][1,3,4]thiadiazole-2-sulfonamide with 6-(2,4-dimethylphenyl) substituent) |
| 49 | (imidazo[2,1-b][1,3,4]thiadiazole-2-sulfonamide with 6-(4-tert-butylphenyl) substituent) |
| 50 | (imidazo[2,1-b][1,3,4]thiadiazole-2-sulfonamide with 6-(6-tert-butyl-1,1-dimethyl-2,3-dihydro-1H-inden-4-yl) substituent) |
| 51 | (imidazo[2,1-b][1,3,4]thiadiazole-2-sulfonamide with 6-(5-adamantan-1-yl-2-methylphenyl) substituent) |

TABLE 2-continued

Compounds

| Example | STRUCTURE |
|---|---|
| 52 | |
| 53 | |
| 54 | |
| 55 | |
| 56 | |
| 57 | |

TABLE 2-continued

Compounds

| Example | STRUCTURE |
|---|---|
| 58 | (structure) |
| 59 | (structure) |
| 60 | (structure) |
| 61 | (structure) |
| 62 | (structure) |
| 63 | (structure) |
| 64 | (structure) |
| 65 | (structure) |

TABLE 2-continued
Compounds
| Example | STRUCTURE |
|---|---|
| 66 | 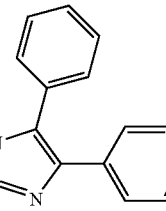 |
| 67 | 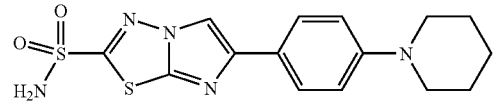 |
| 68 | 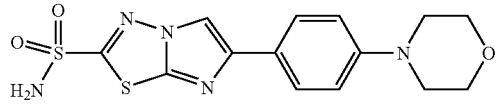 |
| 69 | 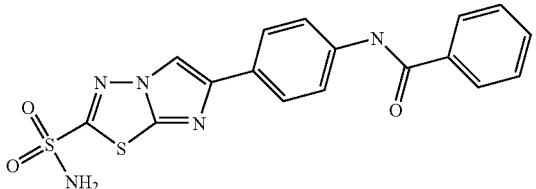 |
| 70 | 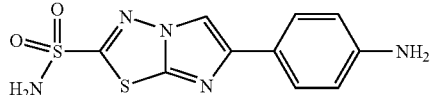 |
| 71 | 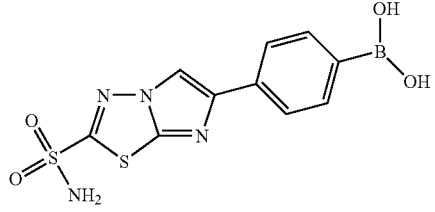 |
| 72 | 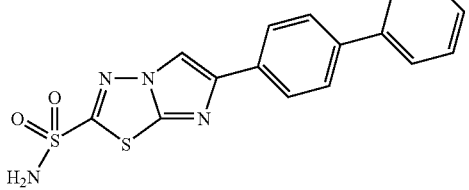 |
| 73 | 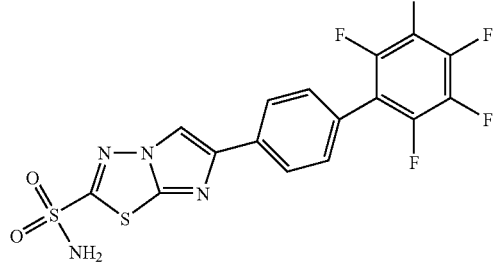 |

TABLE 2-continued

Compounds

| Example | STRUCTURE |
|---|---|
| 74 | 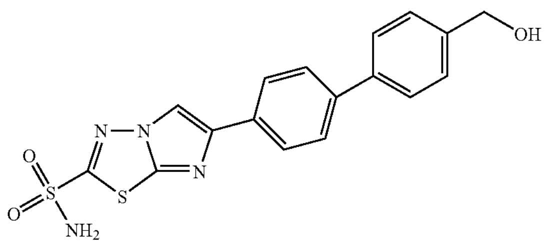 |
| 75 | 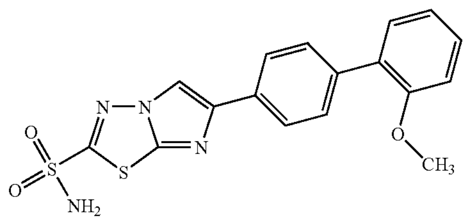 |
| 76 | 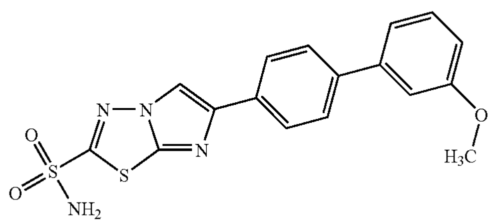 |
| 77 | 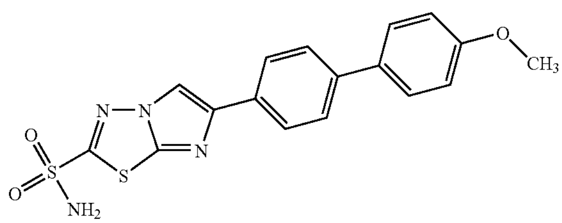 |
| 78 | 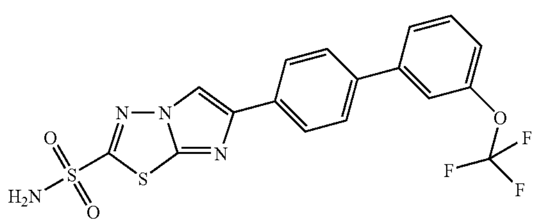 |
| 79 | 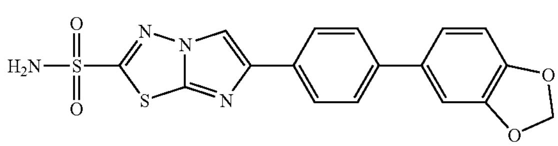 |
| 80 | 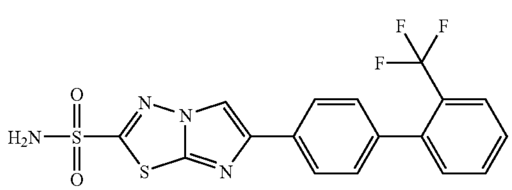 |

TABLE 2-continued

Compounds

| Example | STRUCTURE |
|---|---|
| 81 | |
| 82 | |
| 83 | |
| 84 | |
| 85 | |
| 86 | |

TABLE 2-continued
Compounds
| Example | STRUCTURE |
|---|---|
| 87 | 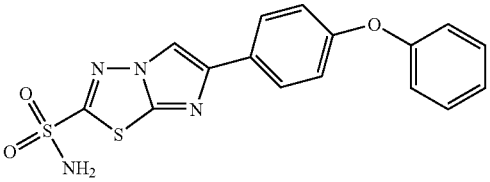 |
| 88 | 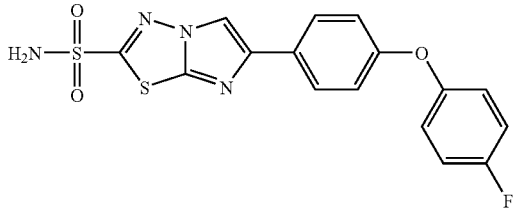 |
| 89 | 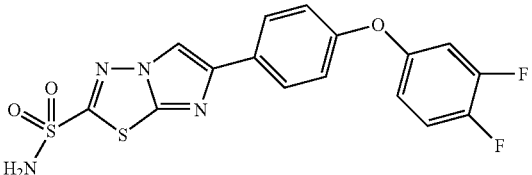 |
| 90 | 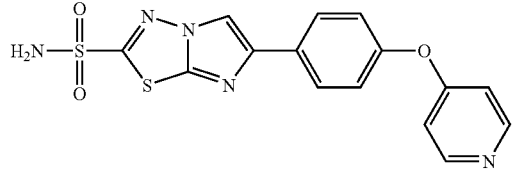 |
| 91 | 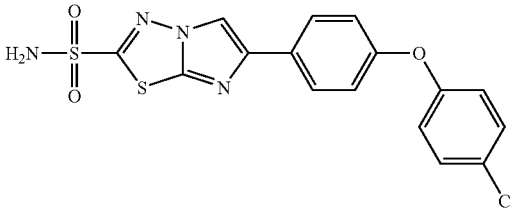 |
| 92 | 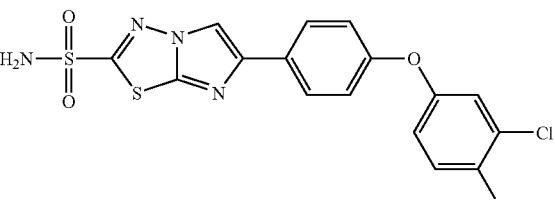 |
| 93 | 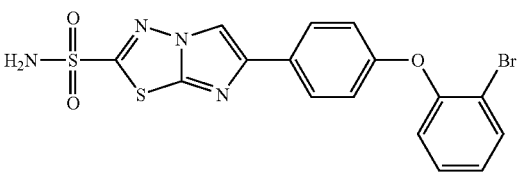 |

TABLE 2-continued

| Example | Compounds STRUCTURE |
|---|---|
| 94 | 6-[4-(3-bromophenoxy)phenyl]imidazo[2,1-b][1,3,4]thiadiazole-2-sulfonamide |
| 95 | 6-[4-(4-bromophenoxy)-3-ethylphenyl]imidazo[2,1-b][1,3,4]thiadiazole-2-sulfonamide |
| 96 | 6-{4-[3-(dimethylamino)phenoxy]phenyl}imidazo[2,1-b][1,3,4]thiadiazole-2-sulfonamide |
| 97 | 6-[4-(4-isopropylphenoxy)phenyl]imidazo[2,1-b][1,3,4]thiadiazole-2-sulfonamide |
| 98 | 6-[4-(4-methoxyphenoxy)phenyl]imidazo[2,1-b][1,3,4]thiadiazole-2-sulfonamide |
| 99 | 6-[4-(4-nitrophenoxy)phenyl]imidazo[2,1-b][1,3,4]thiadiazole-2-sulfonamide |

TABLE 2-continued

Compounds

| Example | STRUCTURE |
|---|---|
| 100 | 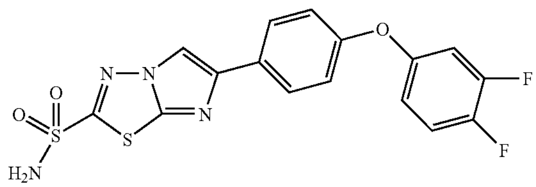 |
| 101 | 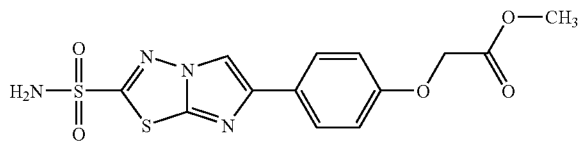 |
| 102 | 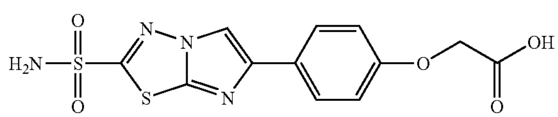 |
| 103 | 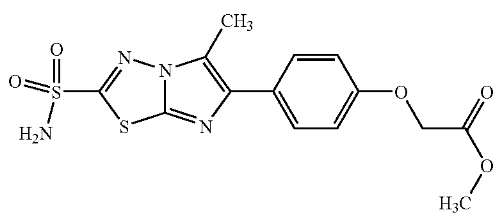 |
| 104 | 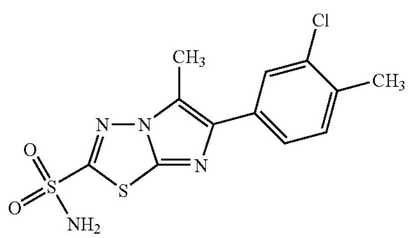 |
| 105 | 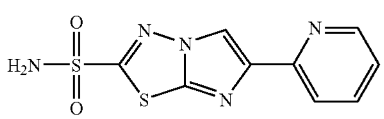 |
| 106 | 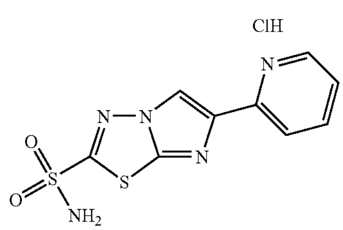 |
| 107 | 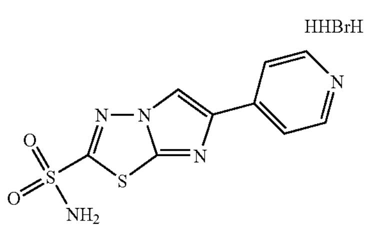 |

TABLE 2-continued

Compounds

| Example | STRUCTURE |
|---|---|
| 108 | (imidazo-thiadiazole sulfonamide with pyrazinyl substituent) |
| 109 | (imidazo-thiadiazole sulfonamide with coumarin-3-yl substituent) |
| 110 | (imidazo-thiadiazole sulfonamide with 3-oxo-3,4-dihydro-2H-benzo[b][1,4]oxazin-6-yl substituent) |
| 111 | (imidazo-thiadiazole sulfonamide with benzofuran-2-yl substituent) |
| 112 | (imidazo-thiadiazole sulfonamide with thiophen-2-yl substituent) |
| 113 | (imidazo-thiadiazole sulfonamide with 5-phenylthiophen-2-yl substituent) |
| 114 | (imidazo-thiadiazole sulfonamide with 5-nitrothiophen-2-yl substituent, HBr salt) |

TABLE 2-continued

Compounds

| Example | STRUCTURE |
|---|---|
| 115 | 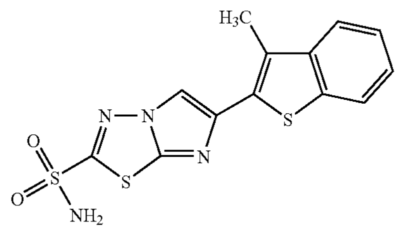 |
| 116 | 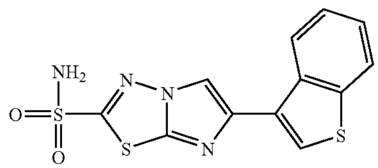 |
| 117 | 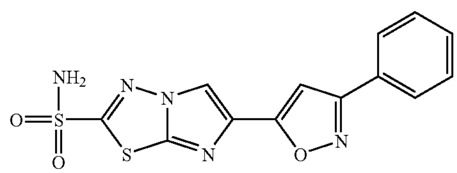 |
| 118 | 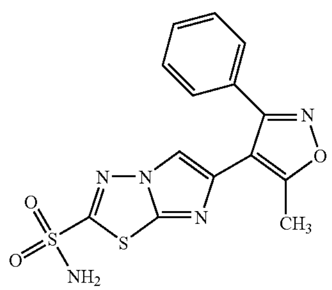 |
| 119 | 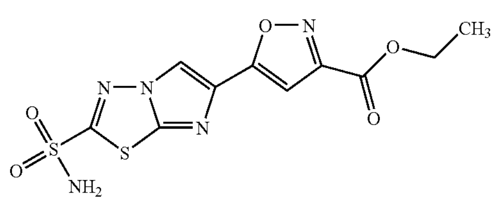 |
| 120 | 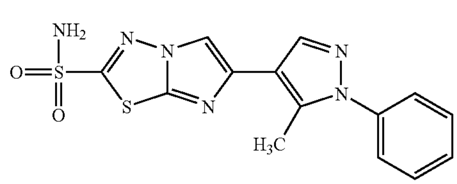 |
| 121 | 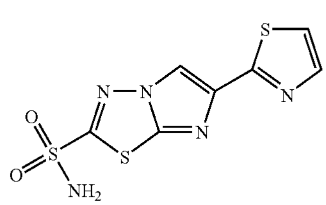 |

TABLE 2-continued

Compounds

| Example | STRUCTURE |
|---|---|
| 122 | 5-(2,4-dimethylthiazol-5-yl)imidazo[2,1-b][1,3,4]thiadiazole-2-sulfonamide |
| 123 | 5-chloro-6-phenylimidazo[2,1-b][1,3,4]thiadiazole-2-sulfonamide |
| 124 | 5-bromo-6-phenylimidazo[2,1-b][1,3,4]thiadiazole-2-sulfonamide hydrobromide |
| 125 | 5-bromo-6-(pyridin-2-yl)imidazo[2,1-b][1,3,4]thiadiazole-2-sulfonamide |
| 126 | 5-bromo-6-(4-nitrophenyl)imidazo[2,1-b][1,3,4]thiadiazole-2-sulfonamide |
| 127 | 5-bromo-6-(4-chlorophenyl)imidazo[2,1-b][1,3,4]thiadiazole-2-sulfonamide |
| 128 | 5-bromo-6-(4-bromophenyl)imidazo[2,1-b][1,3,4]thiadiazole-2-sulfonamide |

TABLE 2-continued

Compounds

| Example | STRUCTURE |
|---|---|
| 129 | (structure) |
| 130 | (structure) |
| 131 | (structure) |
| 132 | (structure) |
| 133 | (structure) |
| 134 | (structure) |
| 135 | (structure) |

TABLE 2-continued

Compounds

| Example | STRUCTURE |
|---|---|
| 136 | |
| 137 | |
| 138 | |
| 139 | |
| 140 | |
| 141 | |

TABLE 2-continued
Compounds
| Example | STRUCTURE |
|---|---|
| 142 | 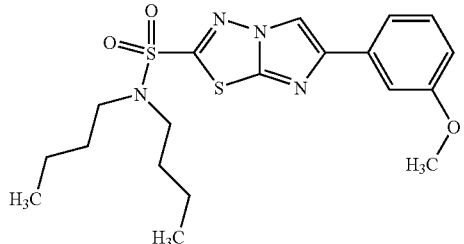 |
| 143 | 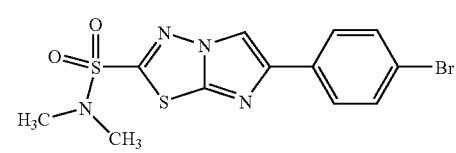 |
| 144 | 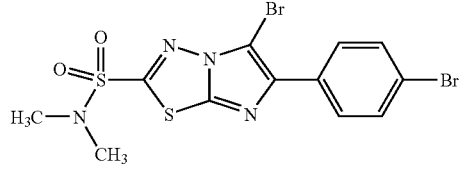 |
| 145 | 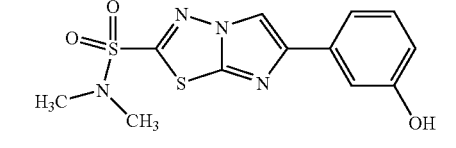 |
| 146 | 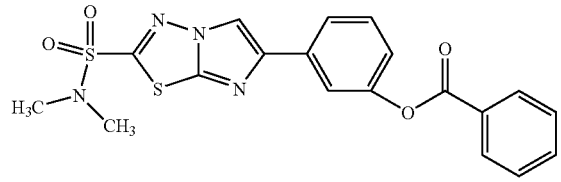 |
| 147 | 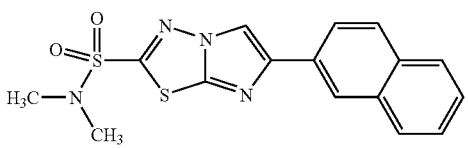 |
| 148 | 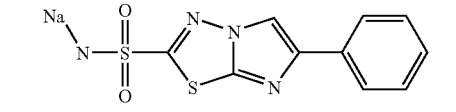 |
| 149 | 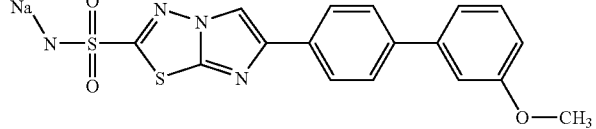 |

TABLE 2-continued

Compounds

| Example | STRUCTURE |
|---|---|
| 150 | 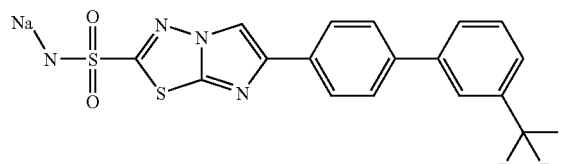 |
| 151 | 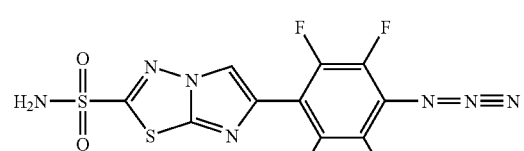 |
| 152 | 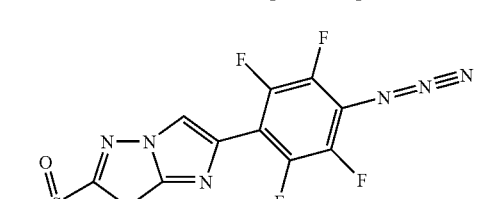 |

Synthetic Procedures

5-Amino-1,3,4-thiadiazole-2-sullonamlue, intermediate E1, was prepared by the acid hydrolysis of acetazolamide (Aldrich). Selected 2-bromoethanones were purchased from either Aldrich Chemical Co. or from Maybridge Inc.

Various acetophenones were readily prepared by the following protocols. A selection of 4-phenoxyacetophenones were prepared under standard Ullmann condensation conditions by heating 4-fluoroacetophenone with the appropriate phenol and $K_2CO_3$ in DMF or DMAc.

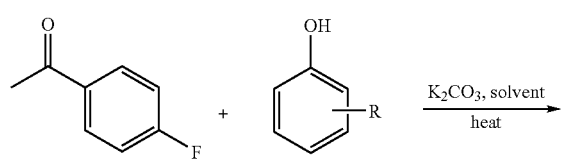

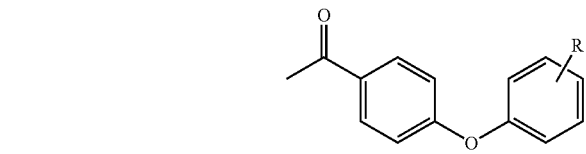

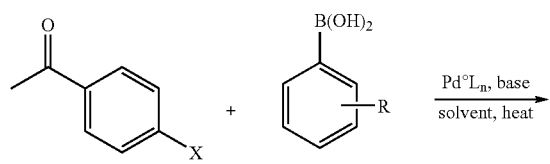

Selected 4'-arylacetophenones were prepared by Suzuki coupling of either 3'- or 4'-haloacetophenone with an arylboronic acid, or 4-acetylbenzeneboronic acid with an arylbromide, using an appropriate palladium catalyst, base, and solvent system. These products may be obtained using alternative coupling partners; ie. Suzuki coupling between aryl bromides and aetophenone boronic acids, the use of flouroboranate salts, the use of Stille couplings between aryl bromides and arylstannanes, etc.

Various acetophenones were α-brominated using bromine or pyridinium tribromide in an appropriate solvent system.

The imidazo[2,1-b]-1,3,4-thiadiazole sulfonamides were prepared according to literature procedures. For example, compound 1 was prepared in good yield by refluxing intermediate A1, with an 2-bromoacetophenone, intermediate B1, in either alcohol or 1,4-dioxane, for 48 hours.

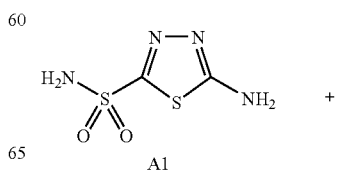

-continued

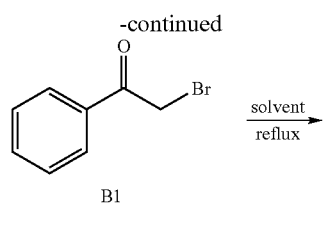

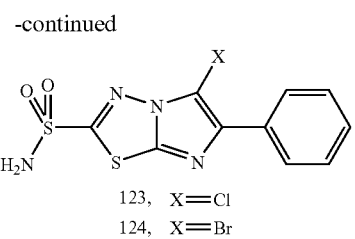

123, X=Cl
124, X=Br

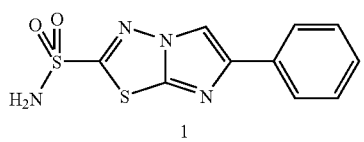

1

Compound 1 was either mono- or dialkylated by the treatment of compound 1 with the appropriate alcohol (1 or 2 equiv), triphenyphosphine, and DIAD or polymer supported DIAD to yield compounds such as 137 and 139. Alternatively, N-alkylation may be accomplished using MeI and NaF/alumina ( ) as base, for the conversion of 1 to 137.

Demethylation of intermediate D with $BBr_3$ provides the phenolic compound 145. Acylation of compound 145 with benzoyl chloride provides compound 146.

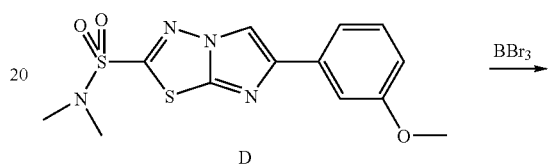

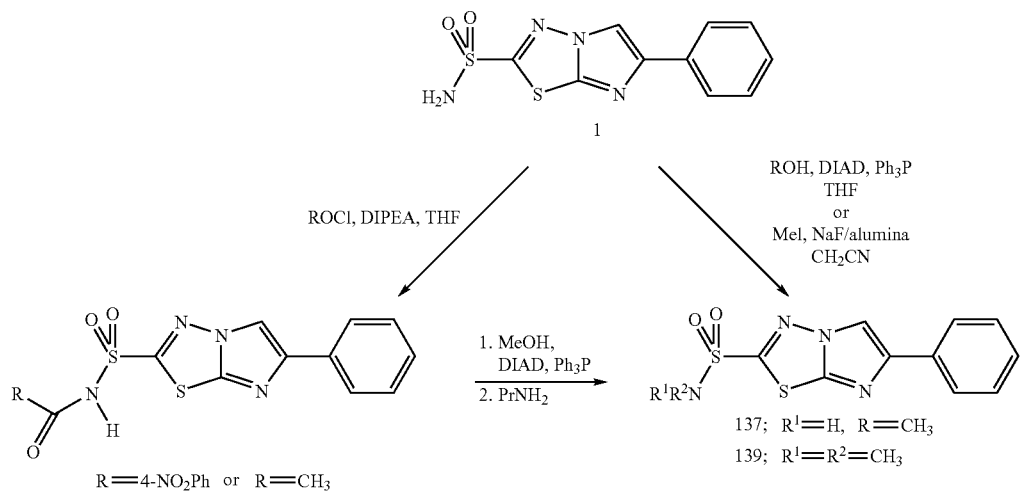

137; $R^1$=H, R=$CH_3$
139; $R^1$=$R^2$=$CH_3$

Selective mono alklylation may be accomplished by alkylation of the N-acyl derivatives of 1, followed by alkylation using Mitsunobu conditions, as above, followed by deacylation with $PrNH_2$, to provide the mono N-methyl derivative 137. This last series of reactions also works with solid supported chemistry.

Compound 1 was readily functionalized at the imidazole methine position by treatment with NaOCl or $Br_2$, to provide compounds 123 and 124, respectively.

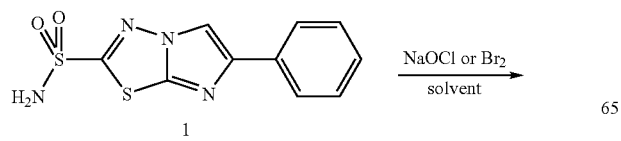

-continued

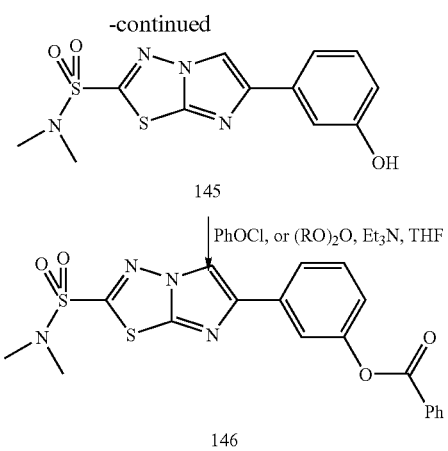

In several cases the requisite 2-bromoacetophenones were commercially available. In other cases they were prepared by the treatment of an appropriately substituted acetophenone with bromine, in an appropriate solvent, as exemplified below. Acylation of 4-aminoacetophenone was followed by bromination in MeOH to provide intermediate A69. Condensation of intermediate A69 with intermediate E1, yielded the desired compound 69.

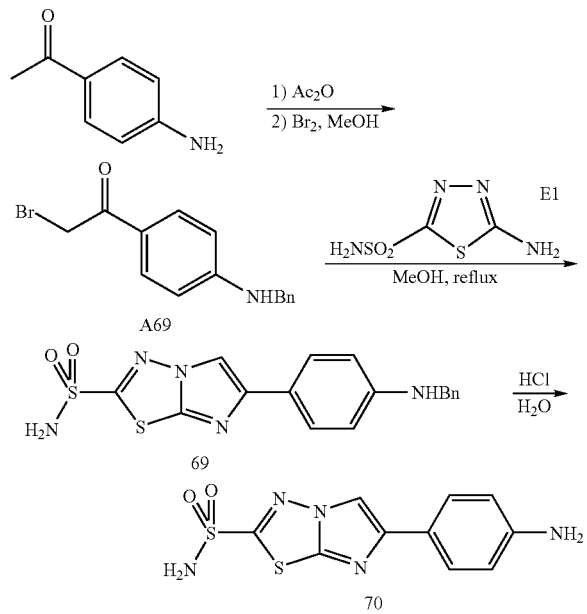

Treatment of compound 69 with methanolic HCl provided compound 70.

Several α-bromoketones were prepared by bromination of the appropriate enol silyl ether. Therefore, deprotonation of either 4'-piperidenylaceophenone (A67) or 4'-morpholinoacetophenone (A68) with LiHMDS, silation with TMSCl, and quenching with N-bromosuccinamide, yielding the desired α-bromoketone intermediates B67 and B68, respectively, as shown below.

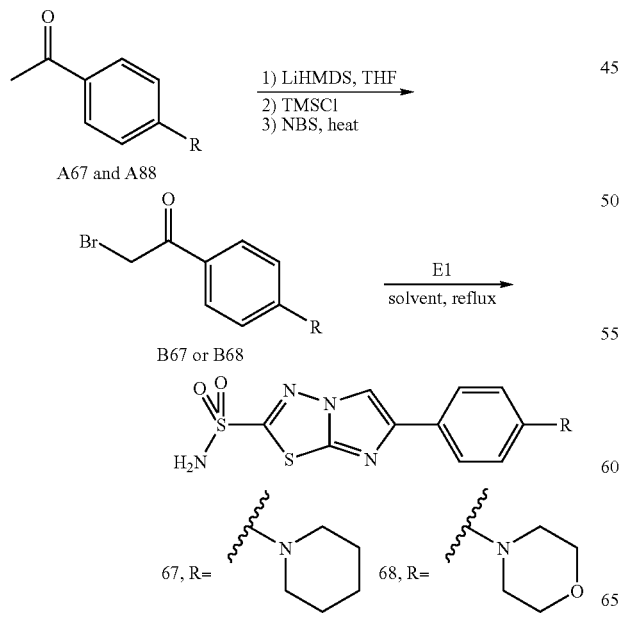

Condensation of B67 and B68 with E1, provided compounds 67 and 68, respectively.

Treatment of selected aryl ketones with bromine or pyridinium perbromide also provided the desired 2-bromoacetophenones, which were again condensed with 2-amino-1,3,4-thiadiazole-5-sulfonamide to provide the desired 6-aryl-imidazo[2,1-b]-1,3,4-thiadiazole-2-sulfonamides, as shown below for compound 58.

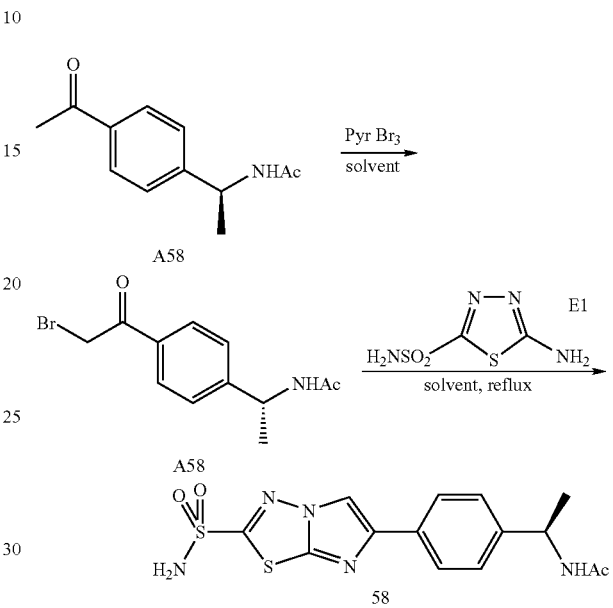

Compound 151 was prepared using the following strategy. 2',3',4',5',6'-Pentafluoroacetophenone, A6 was treated with sodium azide, followed by bromide, to provide 2-bromo-4'-azido-2',3',5',6'-tetrafluoroacetophenone, A151 (Keana, J. F. W.; Cai, S. X. J. *Org. Chem.*, 1990, 55, 3640).

Condensation of A151 with E1 to provided compound 151.

Selected Compound Synthesis

General Preparative Methods

Commercially available acetophenones, 2-haloacetophenones (Intermediates A and B, respectively), phenols (Intermediate C), and benzeneboronic acids (Intermediate D) were purchased from either Aldrich Chemical Company, Lancaster, Maybridge mc, or FisherScientific. The remainder of starting materials were obtained from Aldrich Chemical Company. 5-Amino-1,3,4-thiadiazole-2-sulfonamide, intermediate E1, was prepared by the acid hydrolysis of acetazolamide (Aldrich).

Method A: Bromination of Acetophenones with Bromine

The appropriate acetophenone (Intermediate A) was dissolved in diethyl ether, methylene chloride, or chloroform, and cooled to 0° C. Bromine (1.1 equiv) was dissolved in either methylenechloride or diethyl ether and added to the solution of acetophenone via a dropping funnel. After the addition of bromine was complete 2 drops of acetic acid were added and the solution was warmed to room temperature. Solvent was removed under reduced pressure to provide crude 2-bromoacetophenone (Intermediate B) which was generally used without further purification.

Method B: Bromination of Acetophenones with Pyridinium Tribromide

The appropriate acetophenone (Intermediate A) was dissolved in acetic acid and treated with pyridinium tribromide (1.1 equiv). The solution was stirred until all solid had reacted, the solvent was removed under reduced pressure and the residue was extracted with an appropriate solvent, washing with water. The organic layer was dried over anhydrous magnesium sulphate, filtered, and the solvent removed under reduced pressure to provide the title compounds, which was generally used without further purification.

Method C: Condensation of 2-bromoacetophenone with 2-amino-1,3,4-thiadiazole-5-sulfonamide The appropriate 2-rromoacetophenone and 2-amino-1,3,4-thiadiazole-5-sulfonamide (1.0 equiv) were refluxed in 1,4-dioxane or an appropriate alcohol for 12–60 hrs. The resulting solution was cooled on ice and the resulting precipitate was collected by filtration to provide the title compound as crystalline solid. If no solid was observed the solvent was removed under reduced pressure and the title compounds were purified by silica gel chromatography, trituration, or recrystallization from an appropriate solvent.

EXAMPLE 1

6-Phenylimidazo[2,1-b]-1,3,4-thiadiazole-2-sulfonamide

2-Bromoacetophenone (4.00 g, 20.0 mmol) and 2-amino-1,3,4-thiadiazole-5-sulfonamide (3.60 g, 20.0 mmol) were refluxed in ethanol (150 mL) for 60 hrs. The resulting solution was cooled on ice and the resulting precipitate was collected by filtration to provide compound 1 as a white crystalline solid (2.50 g, 44%). $^1$H NMR (200 MHz, DMSO-$d^6$) δ 8.89 (s, 1H), 8.72 (br s, 2H), 7.90 (d, 2H), 7.43 (t, 2H), 7.32 (t, 1H).

EXAMPLE 2

6-(2-Fluorophenyl)imidazo[2,1-b]-1,3,4-thiadiazole-2-sulfonamide

Compound 2 was prepared by the bromination of 2'-fluoroacetophenone with bromine, according to Method A, followed by condensation with 2-amino-1,3,4-thiadiazole-5-sulfonamide hydrochloride, according to Method C, to provide a white solid. $^1$H NMR (200 MHz, DMSO-$d^6$) δ 8.75 (br s, 2H), 8.6 (d, 1H, j=3.6 Hz), 8.1 (m, 1H), 7.3 (m, 3H).

EXAMPLE 3

6-(3-Fluorophenyl)imidazo[2,1-b]-1,3,4-thiadiazole-2-sulfonamide

Compound 3 was prepared by the bromination of 3'-fluoroacetophenone with bromine, according to Method A, followed by condensation with 2-amino-1,3,4-thiadiazole-5-sulfonamide hydrochloride, according to Method C, to provide a white solid $^1$H NMR (200 MHz, DMSO-$d^6$) δ 8.95 (s, 1H), 8.74 (s, 1H), 7.73 (m, 2H), 7.5 (m, 1H), 7.1 (m, 1H).

EXAMPLE 4

6-(4-Fluorophenyl)imidazo[2,1-b]-1,3,4-thiadiazole-2-sulfonamide

2-Bromo-4'-fluoroacetophenone (1.08 g, 5.0 mmol) 2-amino-1,3,4-thiadiazole-5-sulfonamide hydrochloride (900 mg, 5.0 mmol) were refluxed in ethanol (25 mL) for 48 hrs. The resulting solution was cooled on ice and the resulting precipitate was collected by filtration to provide compound -4 as a white crystalline solid (17 mg). $^1$H NMR (200 MHz, DMSO-$d^6$) δ 8.87 (s, 1H), 8.74 (br s, 2H), 7.40 (m, 2H), 7.28 (m, 2H).

EXAMPLE 5

6-(3,4-Difluorophenyl)imidazo[2,1-b]-1,3,4-thiadiazole-2-sulfonamide

2-Chloro-3',4'-difluoroacetophenone (190 mg, 1.0 mmol) and 2-amino-1,3,4-thiadiazole-5-sulfonamide (150 mg, 1.0 mmol), and CETAB (437 mg, 1.20 mmol) were refluxed in dioxane (5 mL) for 48 hrs. The solvent was removed under reduced pressure and the resulting solid was purified by silica gel chromatography, eluting with 1:1 hexane/ethyl acetate, to provide compound 5 (173 mg, 57%) as a white crystalline solid. $^1$H NMR (200 MHz, acetone-$d^6$) δ 8.41 (d, 1H), 8.26 (m, 1H), 7.92 (br s, 2H), 7.24–7.08 (m, 2H).

EXAMPLE 6

6-(2,3,4,5,6-Pentafluorophenyl)imidazo[2,1-b]-1,3,4-thiadiazole-2-sulfonamide

2-Bromo-1-(pentafluorophenyl)ethan-1-one (2.89 g, 10.0 mmol) and 2-amino- 1,3,4-thiadiazole-5-sulfonamide (1.80 g, 10.0 mmol) were refluxed in ethanol (20 mL) for 60 hrs. Solvent was evaporated and the crude solid was purified by flash chromatography using 20: 80: 0.1 ethyl acetate: hexanes: acetic acid to provide compound 6 as white needles (125 mg, 3.4%). $^1$H NMR (200 MHz, DMSO-$d^6$) δ 8.82 (s, 1H), 8.78 (s, 2H).

EXAMPLE 7

6-(4-Ethylthio-2,3,5,6-tetrafluorophenyl)imidazo[2,1-b]-1,3,4-thiadiazole-2-sulfonamide 2',3',4',5',6'-Pentafluoroacetophenone (2.5 mmol) was heated with ethanethiol (2.5 mmol) in THF (5 mL). Solvent was removed underreduced pressure to provide the desired compounds as a white solid. Pyridinium tribromide (920 mg, 2.5 mmol)) was added and the mixture stirred for 16 hours. Solvent was removed under reduced pressure and 2-amino-1,3,4-thiadiazole-5-sulfonamide (450 mg, 2.5 mmol) was added and solution was refluxed for 48 hours. The solution was cooled to room temperature and filtered to provide compound 7 as a white solid (173 mg, 17%). $^1$H NMR (200 MHz, DMSO-d$^6$) δ 8.82 (s, 1H), 8.79 (br s, 2H), 3.00 (quart, J=8.2 Hz, 2H), 1.98 (t, J=8.2 Hz, 3H).

EXAMPLE 8

6-(4-Benzylthio-2,3,5,6-tetrafluorophenyl)imidazo[2,1-b]-1,3,4-thiadiazole-2-sulfonamide Compound 8 was prepared according to the procedure described for compound 7, using benzylmercaptan in the place of ethanethiol, to provide compound 8 as a white solid (204 mg, 16%). $^1$H NMR (200 MHz, DMSO-d$^6$) δ 8.83 (s, 1H), 8.79 (br s, 2H), 7.23 (s, 5H), 4.21 (s, 2H).

EXAMPLE 9

6-(4-Morpholino-2,3,5,6-tetrafluorophenyl)imidazo[2,1-b]-1,3,4-thiadiazole-2-sulfonamide Compound 6 (100 mg) was dissolved in 1 ml of DMSO and 1 ml of morpholine was added, the solution was heated to 90° C. for 2 hrs. The solution was allowed to cool down to room temperature and ethyl acetate was added. The solution was washed twice with water and once with brine. The organic layer was separated dried over magnesium sulfate and evaporated under reduced pressure. The residue was purified by silica gel chromatography using a 20% to 50% ethyl acetate in hexanes gradient to give a white solid (30 mg). $^1$H NMR (200 MHz, CDCl$_3$) δ 8.05 (s, 1H), 3.76 (m, 4H), 3.27 (m 4H),

EXAMPLE 10

6-(4-Chlorophenyl)imidazo[2,1-b]-1,3,4-thiadiazole-2-sulfonamide

Compound 10 was obtained from Talon.

EXAMPLE 11

6-(3,4-Dichlorophenyl)imidazo[2,1-b]-1,3,4-thiadiazole-2-sulfonamide

2-Bromo-3',4'-dichloroacetophenone (267 mg, 1.0 mmol) and 2-amino-1,3,4-thiadiazole-5-sulfonamide hydrochloride (180 mg, 1.00 mmol) were refluxed in ethanol (20 mL) for 48 hrs. The resulting solution was cooled on ice and the resulting precipitate was collected by filtration to provide compound 11 as a white crystalline solid (91 mg, 26%). $^1$H NMR (200 MHz, DMSO-d$^6$) δ 9.01 (s, 1H), 8.74 (s, 2H), 8.13 (d, 1H), 7.89 (dd, 1H), 7.70 (d, 1H).

EXAMPLE 12

6-(2,3,4-trichlorophenyl)imidazo[2,1-b]-1,3,4-thiadiazole-2-sulfonamide

Compound 12 was prepared by bromination of 2',3',4'-trichloroacetophenone with bromine according to Method A, and condensation of the corresponding 2-bromoacetophenone with 2-amino-1,3,4-thiadiazole-5-sulfonamide, according to Method C, to yield compound 12 as a white solid (22% yield). $^1$H NMR (200 MHz, DMSO-d$^6$) δ 9.00 (s, 1H), 8.74 (br s, 2H), 8.07 (d, J=8.5 Hz, 2H), 7.74 (d, J=8.5 Hz, 2H).

EXAMPLE 13

6-(3-bromophenyl)imidazo[2,1-b]-1,3,4-thiadiazole-2-sulfonamide

Compound 13 was prepared by bromination of 3'-bromoacetophenone with bromine according to Method A, and condensation of the corresponding 2-bromoacetophenone with 2-amino-1,3,4-thiadiazole-5-sulfonamide, according to Method C, to yield compound 13 as a white solid. $^1$H NMR (200 MHz, DMSO-d$^6$) δ 8.94 (d, J=1.3 Hz, 1H), 8.74 (br s, 2H), 8.08 (d, J=1.1 Hz, 1H), 7.90 (dd, J=1.4, 7.7 Hz, 1H), 7.48 (d, J=7.7 Hz, 1H), 7.38(t, J=8.6 Hz, 1H).

EXAMPLE 14

6-(4-Bromophenyl)-imidazo[2,1-b]-1,3,4-thiadiazole-2-sulfonamide

2-Bromo-4'-bromoacetophenone (2.78 g, 10.0 mmol) and 2-amino- 1,3,4-thiadiazole-5-sulfonamide (1.80 g, 12.0 mmol) were refluxed in 1,4-dioxane (25 mL) for 16 hrs. The resulting solution was cooled on ice and the resulting precipitate was collected by filtration to provide compound 14 as a white crystalline solid (3.60 g). $^1$H NMR (200 MHz, DMSO-d$^6$) δ 8.92 (s, 1H), 8.75 (br s, 2H), 7.85 (d, 2H), 7.62 (d, 2H).

EXAMPLE 15

6-(2-Methoxyphenyl)imidazo[2,1-b]-1,3,4-thiadiazole-2-sulfonamide

2-Bromo-2'-methoxyacetophenone (916 mg, 4.0 mmol) and 2-amino-1,3,4-thiadiazole-5-sulfonamide (720 mg, 4.0 mmol) were refluxed in ethanol (20 mL) for 48 hrs. The resulting solution was cooled on ice and the resulting precipitate was collected by filtration to provide compound 15 as a white crystalline solid. $^1$H NMR (200 MHz, DMSO-d$^6$) δ 9.68 (br s, 1H), 8.78 (br s, 2H), 8.12 (d, 1H), 7.34 (t, 1H), 7.11 (d, 1H), 7.05 (t, 1H), 3.96 (s, 3H).

EXAMPLE 16

6-(3-Methoxyphenyl)imidazo[2,1-b]-1,3,4-thiadiazole-2-sulfonamide

2-Bromo-3'-methoxyacetophenone (1.00 g, 4.37 mmol) and 2-amino-1,3,4-thiadiazole-5-sulfonamide (786 mg, 4.37 mmol) were refluxed in 1,4-dioxane (25 mL) for 48 hrs. The resulting solution was cooled on ice and the resulting precipitate was collected by filtration to provide compound 16 as a white crystalline solid (375 mg, 28%).

$^1$H NMR (200 MHz, DMSO-d$^6$) δ 8.89 (s, 1H), 8.73 (br s, 2H), 7.46 (s, 2H), 7.33 (t, J=8.1 Hz, 1H), 6.88 (d, J=7.3 Hz, 1H), 3.80 (s, 3H). $^{13}$C NMR (50 MHz, DMSO-d$^6$) δ 164.3, 159.8, 146.7, 145.2, 134.8, 130.0, 117.4, 113.7, 111.4, 110.3, 55.1.

EXAMPLE 17

6-(4-Methoxyphenyl)imidazo[2,1-b]-1,3,4-thiadiazole-2-sulfonamide

2-Bromo-4'-methoxyacetophenone (2.29 g, 10.0 mmol) and 2-amino-1,3,4-thiadiazole-5-sulfonamide (1.80 g, 12.0 mmol) were refluxed in 1,4-dioxane (25 mL) for 24 hrs. The resulting solution was cooled on ice and the resulting precipitate was collected by filtration to provide compound 17 as a white crystalline solid (2.65 g, 86%). $^1$H NMR (200 MHz, DMSO-d$^6$) δ 8.83 (s, 1H), 8.00 (d, 2H), 7.13 (d, 2H), 3.88 (s, 3H).

EXAMPLE 18

6-(2,5-Dimethoxyphenyl)imidazo[2,1-b]-1,3,4-thiadiazole-2-sulfonamide

2-Bromo-2',5'-dimethoxyacetophenone (261 mg, 1.00 mmol) and 2-amino-1,3,4-thiadiazole-5-sulfonamide (180 mg, 1.20 mmol) were refluxed in 1,4-dioxane (7 mL) for 48 hrs. The resulting solution was cooled on ice and the resulting precipitate was collected by filtration to provide compound 18 as a white crystalline solid (15.5 mg, 5%). $_1$H NMR (200 MHz, DMSO-d$^6$) δ 8.72 (br s, 2H), 8.60 (s, 1H), 7.70 (d, 1H), 7.04 (d, 1H), 6.87 (dd, 1H), 3.89 (s, 3H), 3.74 (s, 3H).

EXAMPLE 19

6-(2,4-Dimethoxyphenyl)imidazo[2,1-b]-1,3,4-thiadiazole-2-sulfonamide

2-Bromo-2',4'-dimethoxyacetophenone (259 mg, 1 mmol) and 2-amino-1,3,4-thiadiazole-2-sulfonamide (180 mg, 1 mmol) were refluxed in ethanol for 5 days. After cooling the resulting precipitate was filtered and washed with methanol, providing 19 (56 mg) as a beige powder. $^1$H NMR (200 MHz, DMSO-d$^6$) δ 8.69 (br s, 2H), 8.47 (s, 1H), 8.06 (d, J=8.8 Hz, 1H), 6.66 (s, 1H), 6.62 (d, J=2.4 Hz, 1H), 3.93 (s, 3H), 3.80 (s, 3H).

EXAMPLE 20

6-(1,3-Benzodioxol-5-yl)imidazo[2,1-b]-1,3,4-thiadiazole-2-sulfonamide 1-(1,3-benzodioxol-5-yl)-2-bromoethan-1-one (100 mg, 0.41 mmol) and 2-amino-1,3,4-thiadiazole-5-sulfonamide (74 mg, 0.41 mmol) were refluxed in ethanol (5 mL) for 30 hrs. The resulting solution was cooled on ice and the resulting precipitate was collected by filtration to provide compound 20 as a pale yellow powder (40 mg, 44%). $^1$H NMR (200 MHz, DMSO-d$^6$) δ 8.75 (s, 1H), 8.69 (s, 2H), 7.43 (m, 2H), 6.97 (d, J=8.6 Hz, 1H), 6.04 (s, 2H).

EXAMPLE 21

6-(3,4-dihydro-2H-1,5-benzodioxepin-7-yl)imidazo[2,1-b]-1,3,4-thiadiazole-2-sulfonamide 2-Bromo-1-(3,4-dihydro-2H-1,5-benzodioxepin-7-yl)ethan-1-one (542 mg, 2 mmol) and 2-amino-1,3,4-thiadiazole-5-sulfonamide (360 mg, 2 mmol) were refluxed in ethanol (10 ml) for 60 hours. The resulting mixture was cooled on ice and the resulting precipitate collected by suction filtration, giving 21 (310 mg) as a yellow powder. $^1$H NMR (200 MHz, DMSO-d$^6$) δ 8.79 (s, 1H), 8.71 (br s, 2H), 7.49 (s, 1H), 7.45 (d, J=7.9 Hz, 1H), 7.00 (d, J=7.9 Hz, 1H), 4.2–4.0 (m, 4H), 2.10 (t, J=4.9 Hz, 2H). $^{13}$C NMR (50 MHz, DMSO-d$^6$) δ 163.9, 151.4, 151.0, 146.2, 145.1, 128.9, 122.0, 120.1, 118.2, 110.7, 70.6, 31.5.

EXAMPLE 22

6-(3,4-Dihydroxyphenyl-imidazo[2,1-b]-1,3,4-thiadiazole-2-sulfonamide

2-Chloro-3',4'-dihydroxyacetophenone (186 mg, 1.0 mmol) and 2-amino-1,3,4-thiadiazole-5-sulfonamide (150 mg, 1.0 mmol), and CETAB (10 mg) were refluxed in dioxane (5 mL) for 48 hrs. The solvent was removed under reduced pressure and the resulting solid was purified by silica gel chromatography, eluting with 1:1 hexane/ethyl acetate, to provide compound 22 (11 mg, 4%) as a white crystalline solid. $^1$H NMR (200 MHz, acetone-d$^6$) δ 8.38 (s, 1H), 8.10 (br s, 2H), 7.84 (br s, 2H), 7.44 (d, 1H), 7.39 (dd, 1H), 6.88 (d, 1H).

EXAMPLE 23

6-(2-spiro(cyclohexyl)benzo-1,3-dioxol-5-yl)imidazo[2,1,-b]-1,3,4-thiadiazole-2-sulfonamide Compound 23 was prepared by the bromination of 6-(2-spiro(cyclohexyl)benzo-1,3-dioxol-5-yl)ethanone with bromine, according to Method A, followed by condensation with 2-amino-1,3,4-thiadiazole-5-sulfonamide hydrochloride, according to Method C, to provide a white solid.

EXAMPLE 24

6-(3-trifloromethoxyphenyl)imidazo[2,1-b]-1,3,4-thiadiazole-2-sulfonamide

Compound 24 was prepared by bromination of 3'-trifluoromethoxyacetophenone with bromine according to Method A, and condensation of the corresponding 2-bromoacetophenone with 2-amino-1,3,4-thiadiazole-5-sulfonamide, according to Method C, to yield compound 24 as a white solid (22% yield). $^1$H NMR (200 MHz, DMSO-d$^6$) δ 9.01 (s, 1H), 8.74 (br s, 2H), 7.92 (d, J=7.6 Hz, 1H), 7.91 (s, 1H), 7.57 (t, J=7.6 Hz, 1H), 7.30 (d, J=7.6 Hz, 1H).

EXAMPLE 25

6-(4-trifloromethoxyphenyl)imidazo[2,1-b]-1,3,4-thiadiazole-2-sulfonamide

Compound 25 was prepared by bromination of 4'-trifluoromethoxyacetophenone with bromine according to Method A, and condensation of the corresponding 2-bromoacetophenone with 2-amino-1,3,4-thiadiazole-5-sulfonamide, according to Method C, to yield compound 25 as a white solid (22% yield). $^1$H NMR (200 MHz, DMSO-d$^6$) δ 8.93 (s, 1H), 8.73 (s, 2H), 8.00 (d, J=8.8 Hz, 2H), 7.43 (d, J=8.4 Hz, 2H).

EXAMPLE 26

Compound 26 was prepared in a manner similar to compound 31.
$^1$H NMR (200 MHz, DMSO-d$^6$) δ=3.71 (t, 2H, J=4.6 Hz), 4.00 (t, 2H, J=4.9 Hz), 6.99 (d, 2H, J=8.3 Hz), 7.81 (d, 2H, J=8.2 Hz), 8.67 (s, 2H), 8.73 (s, 1H)

EXAMPLE 27

Step 1: Compound 26 (472 mg, 1.39 mmol), di-tert-butyldicarbonate (383 μL, 1.67 mmol), triethylamine (194 μL, 1.39 mmol), DMAP (20 mg, 0.16 mmol) were added to DMF (5 mL) and stirred at RT under N$_2$ for 45 min. The volatiles were removed under reduced pressure and the contents washed with H$_2$O and EtOAc. The organic layer was collected, dried over MgSO$_4$. $^1$H NMR (200 MHz, CDCl$_3$) δ 1.23 (s, 9H), 3.73 (t, 2H, J=5.4 Hz), 4.00 (t, 2H, J=5.6 Hz), 7.02 (d, 2H, J=8.8 Hz), 7.82 (d, 2H, J=8.4 Hz), 8.69 (s, 1H).

Step 2: The material from step 1 (627 mg, 1.39 mmol), acetic anhydride (158 μL, 1.67 mmol), triethylamine (233 μL, 1.67 mmol), DMAP (21 mg, 0.17 mmol) were added to DMF (5 mL) and stirred under N$_2$ for 3 h. The volatiles were removed under reduced pressure and the contents washed with H$_2$O and EtOAc. The organic layer was collected, dried over MgSO$_4$. $^1$H NMR (200 MHz, CDCl$_3$) δ 1.20 (s, 9H), 2.08 (s, 3H), 4.09 (b, 2H), 4.40 (b, 2H), 6.90 (d, 2H, J=8.8 Hz), 7.62 (d, 2H, J=8.4 Hz).

Step 3: The material from Step 3 was dissolved in 10 mL TFA/CH$_2$Cl$_2$ (1:1) and stirred for 30 min at RT. The volatiles were removed under reduced pressure and the contents washed with NaHCO$_3$ (aq) and EtOAc. The organic layer was collected, dried over MgSO$_4$. The product was recrytalized from ethanol. $^1$H NMR (200 MHz, DMSO-d$^6$) δ 2.03 (s, 3H), 4.20 (b, 2H), 4.31 (b, 2H), 7.02 (d, 2H, J=8.8 Hz), 7.82 (d, 2H, J=8.4 Hz), 8.69 (s, 2H), 8.76 (s, 1H).

EXAMPLE 28

Step 1: 2-Bromoethanol, K$_2$CO$_3$ and 4-hydroxy acetophenone were refluxed together in MeOH. The solvent was removed under reduced pressure and the residue treated to standard ethyl acetate/water work-up to provide a white semi-sold. $^1$H NMR (200 MHz, CDCl$_3$) δ 2.55 (s, 3H), 3.65 (t, 2H, J=6.1 Hz), 4.35, t, 2H, J=6.4 Hz), 6.94 (d, 2H, J=9.5 Hz), 7.93 (d, 2H, J=8.8 Hz).

Step 2: The material from Step 1 (50 mg, 0.216 mmol), NaN$_3$ (20 mg, 0.307 mmol) were dissolved in acetone (5 mL) and H$_2$O (0.5 mL) and heated to reflux with stirring for 16 h. Solvent was removed and the desired compounds was obtained in quantitative yield. $^1$H NMR (200 MHz, CDCl$_3$) δ 2.55 (s, 3H), 3.63 (t, 2H, J=4.6 Hz), 4.21 (t, 2H, J=5.19 Hz), 6.95 (d, 2H, J=8.85 Hz), 7.94 (d, 2H, J=8.9 Hz).

Step 3: The material from Step 2 was brominated according to Method A and purified on silica gel (4:1, CH$_2$Cl$_2$: Hexanes) to give 1-(4-(2-azidoethoxy)phenyl)-2-bromo ethanone. $^1$H NMR (200 MHz, CDCl$_3$) δ 3.63 (t, 2H, J=4.9 Hz), 4.21 (t, 2H, J=5.2 Hz), 4.40 (s, 2H), 6.95 (d, 2H, J=9.2 Hz), 7.94 (d, 2H, J=8.6 Hz).

Step 4: 1-(4-(2-azidoethoxy)phenyl)-2-bromo ethanone was condensed with 1,3,4-thiadiazole-2-sulfonamide according to Method C yielding an off yellow solid. $^1$H NMR (200 MHz, DMSO-d$^6$) δ 3.65 (t, 2H, J=4.0 Hz), 4.20 (t, 2H, J=4.3 Hz), 7.02 (d, 2H, J=8.2 Hz), 7.83 (d, 2H, J=8.2 Hz), 8.71 (s, 2H), 8.76 (s, 1H).

EXAMPLE 29

Step 1: 3-Bromo-1,1,1-trifluoropropane, K$_2$CO$_3$ and 4'-hyrdoxyacetophenone were refluxed together in MeOH for 16 hours. Volatiles were removed under reduced pressure and the residue subjected to standard ethyl acetate/water work-up. $^1$H NMR (200 MHz, CDCl$_3$) δ 2.48–2.70 (m, 5H), 4.19 (t, 2H, J=6.4 Hz), 6.87 (d, 2H, J=8.8 Hz), 7.87 (d, 2H, 9.2 Hz).

Step 2: 4'-(3,3,3-trifluoropropoxy)acetophenone was brominated according to Method A. $^1$H NMR (200 MHz, CDCl$_3$) δ 2.48–2.70 (m, 2H), 4.27 (t, 2H, J=6.4 Hz), 4.40 (2,2H) 6.96 (d, 2H, J=8.8 Hz), 7.98 (d, 2H, 9.2 Hz).

Step 3: 2-Bromo-4'-(3,3,3-trifluoropropoxy)acetophenone was condensed with 5-Amino-1,3,4-thiadiazole-2-sulfonamide according to Method C, yielding an off yellow solid. $^1$H NMR (200 MHz, DMSO-d$^6$) δ 2.65–2.85 (m, 2H), 4.23 (t, 2H, J=6.2 Hz), 7.02 (d, 2H, J=8.6 Hz), 7.83 (d, 2H, J=8.6 Hz), 8.71 (s, 2H), 8.76 (s, 1H).

EXAMPLE 30

Step 1:1-Bromo-2-(2-methoxyethoxy)ethane, K$_2$CO$_3$ and 4'-hyrdoxyacetophenone were refluxed together in MeOH for 16 hours. Volatiles were removed under reduced pressure and the residue subjected to standard ethyl acetate/water work-up. $^1$H NMR (200 MHz, CDCl$_3$) δ 2.55(s, 3H) 3.39 (s, 3H), 3.56 (t, 2H, J=4.0 Hz), 3.71 (t, 2H, J=4.6 Hz), 3.88 (t, 2H, 4.3 Hz), 4.21 (t, 2H, J=4.9 Hz), 6.94 (d, 2H, J=8.8. Hz), 7.92 (d, 2H, J=8.2 Hz).

Step 2: The material from Step 1 was brominated according to Method A. $^1$H NMR (200 MHz, CDCl$_3$) δ 3.40 (s, 3H), 3.56 (t, 2H, J=4.0 Hz), 3.71 (t, 2H, J=4.6 Hz), 3.88 (t, 2H, 4.3 Hz), 4.21 (t, 2H, J=4.9 Hz), 4.40 (s, 2H), 6.94 (d, 2H, J=8.8. Hz), 7.92 (d, 2H, J=8.2 Hz).

Step 3: The Material from Step 2 was condensed with 2-amino-1,3,4-thiadiazole-2-sulfonamide according to Method C to provide a yellow solid. $^1$H NMR (200 MHz, DMSO-d$^6$) δ 3.23 (s, 3H), 3.47 (b, 2H), 3.57 (b, 2H), 3.73 (b, 2H), 4.11 (b, 2H), 7.00 (d, 2H, J=8.2 Hz), 7.81 (d, 2H, J=8.6 Hz), 8.70 (s, 2H), 8.74 (s, 1H).

EXAMPLE 31

Step 1: 4-Hydroxyacetophenone (500 mg, 3.67 mmol), K$_2$CO$_3$ (510 mg, 3.69 mmol) and benzyl-2-bromoethyl ether (580 μL, 3.67 mmol) were suspended in ethanol (25 mL). The mixture was heated to reflux with stirring for 21 h. The volatiles were removed under reduced pressure and the contents washed with H$_2$O and EtOAc. The organic layer was collected, dried over MgSO$_4$ and purified on silica gel (1:3 EtOAc/Hexanes) yielding 4'-(2-Benzyloxyethoxy)acetophenone as a white crystalline solid (600 mg, 61%). $^1$H NMR (200 MHz, CDCl$_3$) δ 2.55 (s, 3H), 3.85 (t, 2H, J=4.9 Hz), 4.21 (t, 2H, J=4.9 Hz), 4.64 (s, 2H), 6.95 (d, 2H, J=8.9 Hz), 7.35 (b, 5H), 7.93 (d, 2H, J=8.8 Hz).

Step 2: 4-(2-Benzyloxyethoxy)acetophenone (447 mg, 1.65 mmol) was brominated using Method A to yield a yellow oil (51% conversion). $^1$H NMR (200 MHz, CDCl$_3$) δ 3.85 (t, 2H, J=4.9 Hz), 4.21 (t, 2H, J=4.9 Hz), 4.64 (s, 2H), 4.80 (s, 2H), 6.95 (d, 2H, J=8.9 Hz), 7.35 (b, 5H), 7.93 (d, 2H, J=8.8 Hz).

Step 3: 6-(4'-(2-Benzyloxyethoxy)phenyl)-imidazo[2,1-b]-1,3,4-thidiazole-2 sulfonamide The crude material from Step 2 (299 mg, 0.86 mmol) was condensed with 2-amino-1,3,4-thiadiazole-2-sulfonamide using Method C in 2-propanol, yielding a yellow solid (140 mg, 38%). $^1$H NMR (200 MHz, DMSO-d$^6$) δ 3.77 (b, 2H), 4.18 (b, 2H), 4.55 (s, 2H), 7.01 (d, 2H, J=8.5 Hz), 7.33 (b, 5H) 7.81 (d, 2H, J=8.5 Hz), 8.69 (s, 2H), 8.74 (s, 1H).

EXAMPLE 32

Step1: 4-Hydroxyacetophenone (500 mg, 3.67 mmol), K$_2$CO$_3$ (510 mg, 3.69 mmol) and benzyl-3-bromopropyl ether (547 µL, 3.67 mmol) were suspended in ethanol (25 mL). The mixture was heated to reflux with stirring for 21 h. The volatiles were removed under reduced pressure and the contents washed with H$_2$O and EtOAc. The organic layer was collected, dried over MgSO$_4$ and purified on silica gel (1:3 EtOAc/Hex) yielding 4'-(2-Benzyloxyethoxy)acetophenone as a white crystalline solid (737 mg, 71%). $^1$H NMR (200 MHz, CDCl$_3$) δ 2.08–2.14 (m, 2H), 2.56 (s, 3H), 3.67 (t, 2H, J=6.1 Hz), 4.16 (t, 2H, J=6.1 Hz), 4.53 (s, 2H), 6.92 (d, 2H, J=8.5 Hz), 7.31 (s, 5H), 7.93 (d, 2H, J=8.9 Hz).

Step 2: 4'-(3-Benzyloxy)propoxyacetophenone (447 mg, 1.65 mmol) was brominated using Method A to provide a yellow oil (82% conversion). $^1$H NMR (200 MHz, CDCl$_3$) δ 2.08–2.14 (m, 2H), 3.67 (t, 2H, J=6.1 Hz), 4.16 (t, 2H, J=6.1 Hz), 4.40 (s, 2H), 4.53 (s, 2H), 6.92 (d, 2H, J=8.5 Hz), 7.93 (d, 2H, J=8.9 Hz).

Step 3: The crude material from step 3 (671 mg, 1.85 mmol) was condensed with 2-amino-1,3,4-thiadiazole-2-sulfonamide using Method C (2-propanol) provided a yellow solid (85 mg, 10%). $^1$H NMR (200 MHz, DMSO-d$^6$) δ 1.96–2.06 (m, 2H), 3.58 (t, 2H, J=6.4 Hz), 4.08 (t, 2H, J=5.8 Hz), 4.47 (s, 2H), 6.98 (d, 2H, J=8.5 Hz), 7.30 (s, 2H), 7.80 (d, 2H, J=8.5 Hz), 8.69 (s, 2H), 8.73 (s, 1H).

EXAMPLE 33

6-(4-(2-Morpholinoethoxy)phenyl)imidazo[2,1-b]-1,3,4-thiadiazole-2-sulfonamide bis(methanesulfonic acid)

6-(4-(2-Morpholinoethoxy)phenyl)imidazo[2,1-b]-1,3,4-thiadiazole-2-sulfonamide was prepared according to Method C. $^1$H NMR (200 MHz, DMSO-d$^6$) δ 8.70 (s, 1H), 7.82 (8.2 Hz, 2H), 7.05 (d, J=8.2 Hz, 2H), 4.34 (m, 4H), 3.81 (m, 4H), 3.48 (m, 2HH), 3.26 (m, 2H).

6-(4-(2-Morpholinoethoxy)phenyl)imidazo[2,1-b]-1,3,4-thiadiazole-2-sulfonamide (100 mg) was suspended in MeOH (2 mL) and treated with methanesulfonic acid (100 uL). Diethyl ether (10 mL) was added and the resulting solid was filtered and washed with diethyl ether to provide compound 33. $^1$H NMR (200 MHz, D$_2$O) δ 8.09, 7.53 (d, J=6.7 Hz, 2H), 6.97 (d, J=6.7 Hz, 2H), 4.43 (s, 2H), 4.20 (m, 2H), 3.96 (br t, 2H), 3.70 (m, 4H), 3.35 (m, 2H), 2.80 (br s, 4H).

EXAMPLE 34

Compound 34 was prepared in a manner similar to that described for compound 32.

$^1$H NMR (200 MHz, DMSO-d$^6$) δ 3.71 (t, 2H, J=4.9 Hz), 3.82 (s, 2H), 3.98 (t, 2H, J=4.6 Hz), 7.01 (d, 1H, J=8.2 Hz), 7.40–7.48 (m, 3H), 8.71 (s, 2H), 8.79 (s, 1H).

EXAMPLE 35

Compound 35 was prepared in a manner similar to compound 32.

$^1$H NMR (200 MHz, DMSO-d$^6$) δ 8.78 (s, 1H), 8.67 (s, 2H), 7.48 (s, 1H), 7.40 (d, J=8.6 Hz, 1H), 7.34 (s, 5H), 7.02 (d, J=8.6 Hz, 1H), 4.56 (s, 2H), 4.14 (br s, 2H), 3.83 (s, 3H), 3.77 (br s, 2H).

EXAMPLE 36

Compound 36 was prepared in a manner similar to compound 32.

$^1$H NMR (200 MHz, DMSO-d$^6$) δ 8.78 (s, 1H), 8.70 (s, 2H), 7.47 (s, 1H), 7.42 (d, J=8.2 Hz, 1H), 7.30 (s, 5H), 7.01 (d, J=8.2 Hz, 1H), 4.47 (s, 2H), 4.06 (t, J=6.1 Hz, 2H), 3.80 (s, 3H), 3.59 (t, J=6.3 Hz, 2H), 1.99 (t, J=6.1 Hz, 2H).

EXAMPLE 37

6-(3-Nitrophenyl)imidazo[2,1-b]-1,3,4-thiadiazole-2-sulfonamide

2-Bromo-3'-nitroacetophenone (224 mg, 1.0 mmol) and 2-amino-1,3,4-thiadiazole-5-sulfonamide (180 mg, 1.20 mmol) were refluxed in 1,4-dioxane (7 mL) for 48 hrs. The resulting solution was cooled on ice and the resulting precipitate was collected by filtration to provide compound 37 as a yellow crystalline solid (54 mg, 15%). $^1$H NMR (200 MHz, DMSO-d$^6$) δ 9.12 (s, 1H), 8.75 (br s, 2H), 8.70 (t, 1H), 8.31 (d, 1H), 8.14 (d, 1H), 7.72 (t, 1H).

EXAMPLE 38

6-(3-nitro-4-chlorophenyl)imidazo[2,1-b]-1,3,4-thiadiazole-2-sulfonamide

Compound 38 was prepared by bromination of 3-nitro-4-chloroacetophenone with bromine according to Method A, and condensation of the corresponding 2-bromoacetophenone with 2-amino-1,3,4-thiadiazole-5-sulfonamide, according to Method C, to yield compound 38 as a white solid (22% yield). $^1$H NMR (200 MHz, DMSO-d$^6$) δ 9.09 (s, 1H), 8.77 (s, 2H), 8.53 (s, 1H), 8.18 (d, J=6.9 Hz, 2H), 7.86 (d, J=8.5 Hz, 2H).

EXAMPLE 39

Step 1: 4-Acetylbenzoic acid (1.00 g, 6.09 mmol) was suspended in methanol (10 mL). Hydrochloric acid (500 µL) was added. The reaction mixture was refluxed overnight. The resulting suspension was cooled to −10° C., filtered and the solid washed with cold methanol (3×2 mL) to provide methyl 4-acetylbenzoate as a white solid (799 mg, 74%). $^1$H NMR (200 MHz, CDCl$_3$) δ 8.12 (d, J=8.9 Hz, 2H), 8.01 (d, J=8.9 Hz, 2H), 3.95 (s, 3H), 2.65 (s, 3H).

Step 2 Methyl 4-acetylbenzoate (200 mg, 1.12 mmol) was suspended in chloroform (5 mL) and treated with pyridinium tribromide (359 mg, 1.12 mmol). The reaction mixture was stirred overnight. One half equivalent of pyridinium tribromide (179 mg, 0.56 mmol) was added to the reaction mixture and stirred for two days. The solvent was removed under reduced pressure. Standard aqueous/ethyl acetate workup provided a brown solid, which was identified as a 8:12:3 mixture of starting material, methyl 4-(2-bromoacetyl)benzoate and methyl 4-(2,2-dibromoacetyl)benzoate compound. $^1$H NMR (200 MHz, DMSO-d$^6$) δ 8.08 (d, J=6.7 Hz, 4H), 4.98 (s, 2H), 3.87 (s, 3H).

Step 3 Methyl 4-(2-bromoacetyl)benzoate (100 mg, 0.39 mmol) and 5-amino-1,3,4-thiadiazole-2-sulfonamide (70 mg, 0.39 mmol) were refluxed together in methanol (10 mL) for 48 hours. The resulting suspension was cooled to −10° C., filtered and the solid washed with cold methanol (3×2 mL) to provide compound 39 as a white solid (12.9 mg, 9.35%). $^1$H NMR (200 MHz, DMSO-d$^6$) δ 9.03 (s, 1H), 8.70 (br s, 2H), 8.03 (s, 4H), 3.85 (s, 3H).

EXAMPLE 40

6-(4-carboxyphenyl)imidazo[2,1-b]-1,3,4-thiadiazole-2-sulfonamide

Step 1: 4-Acetylbenzoic acid (186 mg, 1.14 mmol) was dissolved in warm acetic acid (5 mL) and treated with bromine (58 mL, 1.14 mmol). The solution was stirred overnight before being cooled on ice. The resulting solid was filtered, washed with 1:1 methanol/water (3×10 mL) and dried in vacuo to provide 4-(2-bromoacetyl)benzoic acid as a white solid (102 mg). $^1$H NMR (200 MHz, DMSO-d$^6$) δ 8.07 (s, 4H), 4.98 (s, 2H).

Step 2: 4-(2-bromoacetyl)benzoic acid (102 mg) and 5-amino-1,3,4-thiadiazole-2-sulfonamide (75 mg, 0.42 mmol) were refluxed together in methanol (20 mL) for 48 hours. The resulting suspension was cooled to −10° C., filtered and the solid washed with cold methanol (3×5 mL) to provide compound 40 as a white crystalline solid (16 mg). $^1$H NMR (200 MHz, DMSO-d$^6$) δ 9.02 (s, 1H), 8.00 (s, 4H).

EXAMPLE 41

6-(3-cyanophenyl)imidazo[2,1-b]-1,3,4-thiadiazole-2-sulfonamide 3-(2-bromoacetyl)benzonitrile (100 mg, 0.45 mmol) and 2-amino-1,3,4-thiadiazole-5-sulfonamide (80 mg, 0.45 mmol) were refluxed in ethanol (10 mL) for 60 hrs. The resulting solution was cooled on ice and the resulting precipitate was collected by filtration to provide compound 41 as a white crystalline solid (78 mg, 57%). $^1$H NMR (200 MHz, DMSO-d$^6$) δ 9.03 (s, 1H), 8.76 (s, 2H), 8.32 (s, 1H), 8.23 (d, J=7.6 Hz, 1H), 7.71 (m, 2H); $^{13}$C NMR (50 MHz, DMSO) δ 164.9, 145.8, 144.6, 134.6, 131.3, 130.2, 129.4, 128.3, 118.7, 112.4, 112.1.

EXAMPLE 42

6-(4-cyanophenyl)imidazo[2,1-b]-1,3,4-thiadiazole-2-sulfonamide 4-(2-bromoacetyl)benzonitrile (448 mg, 2 mmol) and 2-amino-1,3,4-thiadiazole-5-sulfonamide (360 mg, 2 mmol) were refluxed in ethanol for 60 hours. The resulting mixture was cooled on ice and the precipitate collected by suction filtration to provide 42 (300 mg) as a white powder. $^1$H NMR (200 MHz, DMSO-d$^6$) δ 9.07 (s, 1H), 8.77 (br s, 2H), 8.09 (d, 2H), 7.90 (d, 2H).

EXAMPLE 43

6-(4-(methylsulfonyl)phenyl)imidazo[2,1-b]-1,3,4-thiadiazole-2-sulfonamide

2-Bromo-1-[4-(methylsulfonyl)phenyl]ethan-1-one (100 mg, 0.36 mmol) and 2-amino-1,3,4-thiadiazole-5-sulfonamide (65 mg, 0.36 mmol) were refluxed in ethanol (5 mL) for 60 hrs. The resulting solution was cooled on ice and the resulting precipitate was collected by filtration to provide compound 43 as a white powder (55 mg, 43%). $^1$H NMR (200 MHz, DMSO-d$^6$) δ 9.08 (s, 1H), 8.76 (s, 2H), 8.15 (d, J=8.1 Hz, 2H), 7.96 (d, J=8.1 Hz, 2H), 3.23 (s, 3H).

EXAMPLE 44

6-(4-(phenylmethylsulfonyl)phenyl)imidazo[2,1-b]-1,3,4-thiadiazole-2-sulfonamide Compound 44 was prepared by bromination of 4'-(phenylmethylsulfonyl)acetophenone with bromine according to Method A, and condensation of the corresponding 2-bromoacetophenone with 2-amino-1,3,4-thiadiazole-5-sulfonamide, according to Method C, to yield compound 44 as a white solid. $^1$H NMR (200 MHz, DMSO-d$^6$) δ 9.06 (s, 1H), 8.74 (s, 2H), 8.02 (m, 6H), 7.65 (m, 3H).

EXAMPLE 45

Compound 44 was prepared by according to Methods A and C, to yield compound 45 as a white solid. $^1$H NMR (200 MHz, DMSO-d$^6$) δ 9.08 (s, 1H), 8.65 (s, 2H), 8.08 (d, J=8.0 Hz, 2H), 7.85 (d, J=8.0 Hz, 2H), 3.18 (quart, J=7.6 Hz, 2H), 1.05 (t, J=7.6 Hz, 3H).

EXAMPLE 46

6-(4-Pentylphenyl)imidazo[2,1-b]-1,3,4-thiadiazole-2-sulfonamide

2-Bromo-1-(4-pentylphenyl)ethan-1-one (269 mg, 1.0 mmol) and 2-amino-1,3,4-thiadiazole-5-sulfonamide (180 mg, 1.0 mmol) were refluxed in ethanol (10 mL) for 48 hrs. The resulting solution was cooled on ice and the resulting precipitate was collected by filtration to provide compound 46 as a white powder (180 mg, 51%). $^1$H NMR (200 MHz, DMSO-d$^6$) δ 8.81 (s, 1H), 8.71 (s, 2H), 8.79 (d, J=8.2 Hz, 2H), 7.24 (d, J=8.2 Hz, 2H), 2.54 (t, J=7.0 Hz, 2H), 1.57 (quintet, J=7.6 Hz, 2H), 1.27 (m, 4H), 0.85 (t, J=6.7 Hz, 3H); $^{13}$C NMR (50 MHz, DMSO): δ 164.0, 147.1, 145.3, 142.5, 130.9, 128.9, 125.2, 110.7, 34.9, 30.9, 30.6, 22.0, 14.0.

EXAMPLE 47

6-(4-Methylphenyl)imidazo[2,1-b]-1,3,4-thiadiazole-2-sulfonamide

2-Bromo-1-(4-methylphenyl)ethan-1one (213 mg, 1 mmol) and 2-amino-1,3,4-thiadiazole-5-sulfonamide (148 mg, 1 mmol) were refluxed in ethanol (10 mL) for 60 hours. Solvent was removed under reduced pressure. The suspension was cooled to −4° C., filtered and washed with cold methanol (3×5 mL), to provide compound 47 (118 mg, 42%) as a white powder. $^1$H NMR (200 MHz, DMSO-d$^6$) δ 8.80 (s, 1H), 8.71 (s, 2H), 7.78 (d, 2H), 7.23 (d, 2H), 2.31 (s, 3H).

EXAMPLE 48

6-(2,4-dimethylphenyl)imidazo[2,1-b]-1,3,4-thiadiazole-2-sulfonamide

2-Bromo-1-(2,4-dimethylphenyl)ethan-1-one (227 mg, 1 mmol) and 2-amino-1,3,4-thiadiazole-2-sulfonamide (180 mg, 1 mmol) were refluxed in ethanol for 5 days. The volatiles were removed in vacuo. The residue was purified by column chromatography on silica using 30% ethyl acetate/1% acetic acid in hexane as eluant. Recrystallization from dichloromethane gave 48 (30 mg) as a white powder. $^1$H NMR (200 MHz, DMSO-d$^6$) δ 8.71 (br s, 2H), 8.52 (s, 1H), 7.70 (d, J=7.6 Hz, 1H), 7.10 (s, 1H), 7.06 (s, 1H), 2.46 (s, 3H), 2.29 (s, 3H).

EXAMPLE 49

6-(4-(phenylmethylsulfonyl)phenyl)imidazo[2,1-b]-1,3,4-thiadiazole-2-sulfonamide Compound 49 was prepared by bromination of 4'-tert-butylacetophenone with bromine according to Method A, and condensation of the corresponding 2-bromoacetophenone with 2-amino-1,3,4-thiadiazole-5-sulfonamide, according to Method C, to yield compound 49 as a white solid. $^1$H NMR (200 MHz, DMSO-d$^6$) δ 8.81 (s, 1H), 8.70 (s, 2H), 7.81 (d, J=7.9 Hz, 2H), 7.44 (d, J=8.2 Hz, 2H), 1.29 (s, 9H).

EXAMPLE 50

Compound 50 was prepared according to Method A and Method C, to yield compound 50 as a white solid. $^1$H NMR (200 MHz, DMSO-d$^6$) δ 8.72 (br s, 2H), 8.54 (s, 1H), 7.80 (s, 1H), 7.18 (s, 1H), 3.05 (t, 2H), 1.95 (t, 2H), 1.15 (s, 9H).

EXAMPLE 51

MS (m/z) M$^+$=249.10.

EXAMPLE 52

6-(4-(Trifluoromethyl)phenyl)imidazo[2,1-b]-1,3,4-thiadiazole-2-sulfonamide

2-Bromo-1-[4-(trifluoromethyl)phenyl]ethan-1-one (534 mg, 2.0 mmol) and 2-amino-1,3,4-thiadiazole-5-sulfonamide (360 mg, 2.0 mmol) were refluxed in ethanol (10 mL) for 60 hrs. The resulting solution was cooled on ice and the resulting precipitate was collected by filtration to provide compound 52 as a white powder (270 mg, 39%). $^1$H NMR (200 MHz, DMSO-d$^6$) δ 9.05 (s, 1H), 8.74 (s, 2H), 8.10 (d, J=8.0 Hz, 2H), 7.80 (d, J=8.0 Hz, 2H).

EXAMPLE 53

6-(5-chloro-2-trifluoromethylphenyl)imidazo[2,1-b]-1,3,4-thiadiazole-2-sulfonamide Compound 51 was prepared by bromination of 5'-chloro-4'-trifluoromethylacetophenone with bromine according to Method A, and condensation of the corresponding 2-bromoacetophenone with 2-amino-1,3,4-thiadiazole-5-sulfonamide, according to Method C, to yield compound 53 as a white solid. $^1$H NMR (200 MHz, DMSO-d$^6$) δ 9.04 (s, 1H), 8.78 (s, 2H), 8.47 (s, 1H), 7.82 (d, J=8.6 Hz, 1H), 7.72 (d, J=8.6 Hz, 1H).

EXAMPLE 54

6-(3,5-di(trifluoromethyl)phenyl)imidazo[2,1-b]-1,3,4-thiadiazole-2-sulfonamide

2-Bromo-1-[3,5-di(trifluoromethyl)phenyl]ethan-1-one (670 mg, 2.0 mmol) and 2-amino-1,3,4-thiadiazole-5-sulfonamide (360 mg, 2.0 mmol) were refluxed in ethanol (10 mL) for 60 hrs. The resulting solution was cooled on ice and the resulting precipitate was collected by filtration to provide compound 54 as a white powder (292 mg, 70%). $^1$H NMR (200 MHz, DMSO-d$^6$) δ 9.26 (s, 1H), 8.77 (s, 2H), 8.54 (s, 2H), 8.04 (s, 1H).

EXAMPLE 55

6-(3,4-Di-tert-butyl-4-hydroxyphenyl)imidazo[2,1-b]-1,3,4-thiadiazole-2-sulfonamide 2-Bromo-1-(3,4-di-tert-butyl-4-hydroxyphenyl)ethan-1-one (327 mg, 1 mmol) and 2-amino-1,3,4-thiadiazole-5-sulfonamide (148 mg, 1 mmol) were refluxed in ethanol (10 mL) for 60 hours. Solvent was removed under reduced pressure. The resulting solid was suspended in methanol (5 mL) and stirred for 30 minutes prior to suction filtration, washing twice for cold methanol (2 mL), to provide compound 55 (93 mg, 24%) as a white powder. $^1$H NMR (200 MHz, DMSO-d$^6$) δ 8.72 (s, 1H), 8.68 (s, 2H), 7.63 (s, 2H), 1.41 (s, 9H).

EXAMPLE 56

6-(5,5,8,8-Tetramethyl-5,6,7,8-tetrahydronaphthalen-2-yl)imidazo[2,1-b]-1,3,4-thiadiazole-2-sulfonamide 2-Bromo-1-(5,5,8,8-tetramethyl-5,6,7,8-tetrahydronaphthalen-2-yl)ethan-1-one (250 mg, 0.81 mmol) and 2-amino-1,3,4-thiadiazole-5-sulfonamide (146 mg, 0.81 mmol) were refluxed in ethanol (10 mL) for 60 hours. Solvent was evaporated under reduced pressure and the resulting solid suspended in ethanol (3 ml). The precipitate was collected by suction filtration and washed with ethanol to provide compound 56 (45 mg) as an off white solid. $^1$H NMR (200 MHz, DMSO-d$^6$) δ 8.8 (s, 1H), 8.6 (br s, 2H), 7.8 (br s, 1H), 7.6 (dd, 1H), 7.3 (d, 1H), 1.6 (s, 4H), 1.3 (s, 6H), 1.2 (s, 6H).

EXAMPLE 57

$^1$H NMR (200 MHz, DMSO-d$^6$) δ 8.73 (s, 2H), 8.48 (s, 1H), 7.75 (s, 1H), 7.18 (s, 1H), 5.42 (br s, 4H), 2.21 (s, 3H), 1.63 (s, 3H), 1.23 (s, 9H).

EXAMPLE 58

6-(4-(S-1-acetamidoethyl)phenyl)imidazo[2, 1-b]-1,3 ,4-thiadiazole-2-sulfonamide 2-Bromo-4'-(S-1-acetamidoethyl)acetophenone (426 mg, 1.5 mmol) and 2-amino-1,3,4-thiadiazole -5-sulfonamide (222 mg, 1.5 mmol) were refluxed in ethanol (10 mL) for 60 hours. The resulting solution was cooled to −4° C. for 2 hours and the resulting solid was filtered, washing twice for cold methanol (2 mL), to provide compound 58 (172 mg, 34 %) as white crystals. $^1$H NMR (200 MHz, DMSO-d$^6$) δ 8.82 (s, 1H), 8.70 (s, 2H), 8.28 (d, 1H), 7.83 (d, 2H), 7.34 (d, 2H), 4.91 (dt, 1H), 1.83 (s, 3H), 1.33 (d, 3H).

EXAMPLE 59

6-(4-(Trifluoromethyl)imidazo[2,1-b]-1,3,4-thiadiazole-2-sulfonamide

3 -bromo-1,1,1 -trifluoropropan-2-one (534 mg, 2.0 mmol) and 2-amino-1,3,4-thiadiazole-5-sulfonamide (360 mg, 2.0 mmol) were refluxed in ethanol (10 mL) for 60 hrs. The resulting solution was cooled on ice and the resulting precipitate was collected by filtration to provide compound 59 as a white powder (270 mg, 39%). $^1$H NMR (200 MHz, DMSO-d$^6$) δ 9.05 (s, 1H), 8.74 (s, 2H).

EXAMPLE 60

6-(1-adamantyl)imidazo[2,1-b]-1,3,4-thiadiazole-2-sulfonamide 1-(1-Adamantyl)-2-bromoethan-1-one (514 mg, 2.0 mmol) and 2-amino-1,3,4-thiadiazole-5-sulfonamide (360 mg, 2.0 mmol) were refluxed in ethanol (10 mL) for 60 hrs. The resulting solution was cooled on ice and the resulting precipitate was collected by filtration to provide compound 60 as a white powder (120 mg, 18%). $^1$H NMR (200 MHz, DMSO-d$^6$) δ 8.64 (s, 2H), 8.03 (s, 1H), 2.03 (m, 3H), 1.90 (m, 6H), 1.72 (m, 6H).

EXAMPLE 61

6-(1-Naphthyl)imidazo[2,1-b]-1,3,4-thiadiazole-2-sulfonamide

Compound 61 was prepared by bromination of 1-acetyl-napthylene with bromine according to Method A, followed by condensation of the corresponding bromide with 2-amino-1,3,4-thiadiazole-5-sulfonamide, according to Metod C, to yield an off white solid. $^1$H NMR (200 MHz, DMSO-d$^6$) δ 9.25 (br s, 2H), 8.79 (s, 1H), 8.77 (s, 1H), 8.63 (dd, 1H), 7.97 (m, 2H), 7.78 (dd, J=1.2, 7.0 Hz, 1H), 7.61–7.49 (m, 2H).

EXAMPLE 62

6-(2-Naphthyl)imidazo[2,1-b]-1,3,4-thiadiazole-2-sulfonamide

2-Bromonaphthone (2.50 g, 10.0 mmol) and 2-amino-1,3,4-thiadiazole-5-sulfonamide (1.80 g, 1.2 mmol) were refluxed in 1,4-dioxane (20 mL) for 96 hrs. The resulting solution was cooled on ice and the resulting precipitate was collected by filtration to provide compound 62 as a tan crystalline solid (2.36 g, 38%) in two crops. $^1$H NMR (200 MHz, DMSO-d$^6$) δ 8.99 (s, 1H), 8.74 (br s, 2H), 8.42 (s, 1H), 8.05 (d, 1H), 7.96–7.89 (m, 2H), 7.51 (m, 2H).

EXAMPLE 63

6-(8-Bromo-7-methoxylnaphth-2-yl)imidazo[2,1-b]-1,3,4-thiadiazole-2-sulfonamide

Step 1: 2-Acetyl-6-methoxyacetophenone (1.00 g, 5.0 mmol) was dissolved in methanol (5 mL) and was treated with bromine (500 μL, 10.0 mmol). The reaction was stirred at room temperature for 2 hours before the volatiles were removed in vacuo to provide a 95:5 mixture of 2,7'-dibromo-6'-methoxylnaphone and 2-acetyl-6-methoxyacetophenone. This crude mixture was advanced to the next step without further purification. $^1$H NMR (200 MHz, DMSO-d$^6$) δ 8.75 (s, 1H), 8.20 (d, 1H), 8.10 (d, 1H), 8.07 (dd, 1H), 7.64 (d, 1H), 5.01 (s, 2H), 4.03 (s, 3H).

Step 2: To the crude mixture obtained above was added 5-amino-1,3,4-thiadiazole-2-sulfonamide (740 mg, 5.0 mmol) and methanol (20 mL). The resulting suspension was refluxed for 48 hours, cooled on ice and the solid filtered off, to provide compound 63 as a white solid (230 mg). $^1$H NMR (200 MHz, DMSO-d$^6$) δ 8.95 (s, 1H), 8.76 (d, 1H), 8.44 (s, 1H), 8.11 (s, 2H), 8.02 (d, 1H), 7.52 (d, 1H), 3.99 (s, 3H).

EXAMPLE 64

6-pyrenylimidazo[2,1-b]-1,3,4-thiadiazole-2-sulfonamide 1-(Bromoacetyl)-pyrene (646 mg, 2 mmol) and 2-amino-1,3,4-thiadiazole-5-sulfonamide (360 mg, 2 mmol) were refluxed in ethanol (20 ml) for 60 hrs. Solvent was removed under reduced pressure. The resulting solid was purified by silica gel chromatography, eluting with solvent gradient of 30–100% ethyl acetate/hexane, to afford compound 64 as a brownish orange solid (4.5 mg). $^1$H NMR (200 MHz, DMSO-d$^6$) δ 9.0 (s, 1H), 8.8 (s, 2H), 8.50–8.00 (m, 9H).

EXAMPLE 65

5-Methyl-6-phenyl-imidazo[2,1-b]-1,3,4-thiadiazole-2-sulfonamide

2-Bromopropiophenone (1.07 mg, 5.00 mmol) and 2-amino-1,3,4-thiadiazole-5-sulfonamide hydrochloride (900 mg, 5.0 mmol) were refluxed in ethanol (25 mL) for 48 hrs. The resulting solution was cooled on ice and the resulting precipitate was collected by filtration to provide compound 65 as a white crystalline solid (100 mg). $^1$H NMR (200 MHz, DMSO-d$^6$) δ 8.75 (br s, 3H), 7.75 (d, 2H), 7.45 (t, 2H), 7.30 (t, 1H), 2.65 (s, 3H).

EXAMPLE 66

5,6-Diphenyl-imidazo[2,1-b]-1,3,4-thiadiazole-2-sulfonamide

2-Desyl bromide (550 mg, 2 mmol) and 2-amino-1,3,4-thiadiazole-5-sulfonamide (360 mg, 2 mmol) were refluxed in ethanol (20 ml) for 60 hrs. Solvent was removed under reduced pressure. Purification by silica gel chromatography, eluting with 30:0.1:70 ethyl acetate/acetic acid/hexane, and recrystallization from dichloromethane gave compound 66 as a white crystalline solid (175 mg). $^1$H NMR (200 MHz, DMSO-d$^6$) δ 8.8–8.6 (s, 2H), 7.7–7.4 (m, 7H), 7.4–7.2 (m, 3H).

EXAMPLE 67

6-(4-Piperidinophenyl)imidazo[2,1-b]-1,3,4-thiadiazole-2-sulfonamide

Step 1: 4'-Piperidinoacetophenone (203 mg, 1.00 mmol) was dissolved in THF (5 mL) and treated with lithium bis(trimethylsilyl)amide (1.10 mL, 1.0M in THF, 1.10 mmol). The solution was stirred for 30 minutes prior to the addition of chlorotrimethylsilane (140 μL, 1.10 mmol). After stirring for an additional 30 minutes N-bromosuccinamide (300 mg, 1.73 mmol) was added and the mixture was refluxed from 4 hours. Standard aqueous/ethyl acetate workup provided a yellow solid which was further purified by silica gel chromatography, eluting with 3:1 hexane/ethyl acetate, to provide 2-bromo-4'-piperidinoacetophenone as an off white solid (209 mg, 74%). $^1$H NMR (200 MHz, CDCl$_3$) δ 8.75 (d, 2H), 6.84 (d, 2H), 4.61 (s, 2H), 3.40 (m, 4H), 1.68 (m, 6H).

Step 2: 2-Bromo-4'-piperidinoacetophenone (209 mg, 0.74 mol) and 5-amino-1,3,4-thiadiazole-2-sulfonamide (220 mg, 1.48 mmol) were suspended in 1,4-dioxane (10 mL) and refluxed for 48 hours. The solvent was removed under reduced pressure and the residue was purified by silica gel chromatography, eluting with 1:1 hexane/ethyl acetate, to provide compound 67 as a yellow solid (8.0 mg, 2.7%). $^1$H NMR (200 MHz, DMSO-d$^6$) δ 8.68 (s, 3H), 7.75 (d, 2H), 6.98 (d, 2H), 3.23 (m, 4H), 1.57 (m, 6H).

EXAMPLE 68

6-(4-Morpholinophenyl)imidazo[2,1-b]-1,3,4-thiadiazole-2-sulfonamide

Step 1: 4'-Morpholinoacetophenone (218 mg, 1.0 mmol) was dissolved in THF (5 mL) and treated with lithium bis(trimethylsilyl)amide (1.1 mL, 1.0M in THF, 1.1 mmol). The solution was stirred for 30 minutes prior to the addition of chlorotrimethylsilane (140 μL, 1.1 mmol). After stirring for an additional 30 minutes N-bromosuccinamide (300 mg, 1.73 mmol) was added and the mixture was refluxed from 4 hours. Standard aqueous/ethyl acetate workup provided a yellow solid, which was identified as a 3:1 mixture of 2-bromo-4'-morpholinoacetophenone and starting material. $^1$H NMR (200 MHz, CDCl$_3$) δ 7.86 (d, 2H), 6.84 (d, 2H), 4.62 (s, 2H), 3.84 (t, 4H), 3,32 (t, 4H).

Step 2: The crude 2-Bromo-4'-morpholinoacetophenone from above and 5-amino-1,3,4-thiadiazole-2-sulfonamide (100 mg, 0.66 mmol) were suspended in 1,4-dioxane (10 mL) and refluxed for 48 hours. The solvent was removed under reduced pressure and the residue was purified by silica gel chromatography, eluting with 1:1 hexane/ethyl acetate, to provide compound 68 as a yellow solid (23 mg). $^1$H NMR (200 MHz, DMSO-d$^6$) δ 8.67 (s, 3H), 7.74 (d, 2H), 6.99 (d, 2H), 3.75 (t, 4H), 3.13 (t, 4H).

EXAMPLE 69

6-(4-Benzoylamidophenyl)imidazo[2,1-b]-1,3,4-thiadiazole-2-sulfonamide

Step 1: 4-Aminoacetophenone (1.35 g, 10.0 mmol) was dissolved in dichloromethane (10 mL) and treated with benzoyl chloride (1.74 mL, 15.0 mmol). The mixture was stirred for 16 hours at which time a white precipitate had formed. The solid was removed by filtration, washing with dichloromethane (3×20 mL) to provide 4-acetamidoacetophenone as a white sold (2.74 g). $^1$H NMR (200 MHz, DMSO-d$^6$) δ 10.53 (s, 1H), 7.92 (s, 7H), 7.54 (m, 3H), 2.50 (s, 3H).

Step 2: 4-Benzoylamidoacetophenone (2.55 g) was dissolved in acetic acid (25 mL) and was treated with pyridinium tribromine (3.00 g, 8.0 mmol). The reaction was stirred at room temperature for 24 hours before the volatiles were removed in vacuo to provide 2-bromo-4'-benzoylamidoacetophenone. This crude mixture was advanced to the next step without further purification. $^1$H NMR (200 MHz, DMSO-d$^6$) δ 10.61 (s, 1H), 8.96 (d, 2H), 8.61 (t, 1H), 8.15–8.00 (m, 7H), 4.86 (s, 2H).

Step 3: To the crude mixture obtained above was added 5-amino-1,3,4-thiadiazole-2-sulfonamide (1.50 mg, 10.0 mmol) and methanol (20 mL). The resulting suspension was refluxed for 48 hours. The solvent was removed under reduced pressure and the residue was triturated from acetone to provide compound 69 as a yellow solid (120 mg). $^1$H NMR (200 MHz, DMSO-d$^6$) δ 10.35 (s, 1H), 8.82 (s, 1H), 8.70 (br s, 2H), 7.92 (d, 2H), 7.82 (s, 5H), 7.54 (d, 2H).

EXAMPLE 70

6-(4-Aminophenyl)imidazo[2,1-b]-1,3,4-thiadiazole-2-sulfonamide

Compound 66 (60 mg) was suspended in methanol (10 mL) and treated with 6N HCl (1 mL). The suspension was refluxed for 16 hours until all solids had dissolved. The solvent was removed under reduced pressure and the residue was suspended in water (10 mL), neutralized with saturated aqueous NaHCO$_3$. The resulting precipitate was extracted with ethyl acetate to provide compound 70 as a yellow solid (15 mg). $^1$H NMR (200 MHz, DMSO-d$^6$) δ 8.65 (br s, 2H), 8.53 (s, 1H), 7.58 (d, 2H), 6.58 (d, 2H), 5.32 (br s, 2H).

EXAMPLE 71

Compound 77 was prepared by the bromination of 4-acetylphenylboronic acid according to Method A to yield the desired α-bromoacetophenone, which was condensed with 2-amino-1,3,4-thiadiazole-5-sulfonamide according to Method C, to yield compound 71 as a white solid. $^1$H NMR (200 MHz, DMSO-d$^6$) δ 8.89 (s, 1H), 8.73 (s, 2H), 8.05 (br s, 2H), 7.86 (s, 4H).

EXAMPLE 72

6-(Biphenyl)imidazo[2,1-b]-1,3,4-thiadiazole-2-sulfonamide

2-Bromo-4'-phenylacetophenone (1.38 g, 5.0 mmol) and 2-amino-1,3,4-thiadiazole-5-sulfonamide hydrochloride (0.90 g, 5.0 mmol) were refluxed in ethanol (20 mL) for 60 hrs. The resulting solution was cooled on ice and the resulting precipitate was collected by filtration to provide compound 72 as a white solid (0.75 g, 45%). $^1$H NMR (200 MHz, DMSO-d$^6$) δ 8.95 (s, 1H), 8.74 (s, 2H), 8.00 (d, J=8.6 Hz, 2H), 7.74 (m, 4H), 7.44 (m, 3H).

EXAMPLE 73

6-(4-(2,3,4,5,6-tetrafluorophenyl)phenyl)imidazo[2,1-b]-1,3,4-thiadiazole-2-sulfonamide Step 1: 4'-Bromoacetopherione and 2,3,4,5,6-tetrafluorobenzene boronic (5.0 mmol) acid, K$_2$CO$_3$ (10 mmol), and PdCl$_2$(PPh)$_2$ (0.1 equiv) were refluxed in toluene for 16 hours. The solvent was removed under reduced pressure and the residue was purified by silica gel chromatography, eluting with 4:1 hexane/ethyl acetate, to provide 4'-(2,3,4,5,6-tetrafluorophenylacetophenone as a white solid.

Step 2: 4'-(2,3,4,5,6-Tetrafluorophenylacetophenone was dissolved in diethyl ether and treated with bromine (5 mmol). Solvent was removed under reduced pressure to provide 2-bromo-4'-(2,3,4,5,6-tetrafluorophenylacetophenone, which was used without further purification.

Step 3: 2-bromo-4'-(2,3,4,5,6-tetrafluorophenylacetophenone and 2-amino-1,3,4-thiadiazole-5-sulfonamide hydrochloride (0.90 g, 5.0 mmol) were refluxed in ethanol (20 mL) for 60 hrs. The resulting solution was cooled on ice and the resulting precipitate was collected by filtration to provide compound 73 as a white solid (0.75 g, 45%). $^1$H NMR (200 MHz, DMSO-d$^6$) δ 8.99 (s, 1H), 8.74 (s, 2H), 8.05 (d, J=8.6 Hz, 2H), 7.57 (d, J=8.6 Hz, 2H).

EXAMPLE 74

6-(4-(hydroxymethylphenyl)phenyl)imidazo[2,1-b]-1,3,4-thiadiazole-2-sulfonamide

Compound 74 was prepared in a manner similar to compound 73.

$^1$H N (200 MHz, DMSO-d$^6$) δ 8.93 (s, 1H), 8.73 (s, 2H), 7.98 (d, J=8.2 Hz, 2H), 7.73 (d, J=8.2 Hz, 2H), 7.67 (d, J=8.2 Hz, 2H), 7.39 (d, J=8.2 Hz, 2H), 4.53 (s, 2H).

EXAMPLE 75

6-(4-(2-methoxyphenyl)phenyl)imidazo[2,1-b]-1,3,4-thiadiazole-2-sulfonamide

Compound 75 was prepared in a manner similar to compound 73.

$^1$H NMR (200 MHz, DMSO-d$^6$) δ 8.89 (s, 1H), 8.73 (s, 2H), 7.92 (d, J=8.3 Hz, 2H), 7.53 (d, J=8.3 Hz, 2H), 7.31 (m, 2H), 7.10 (d, J=8.5 Hz, 1H), 7.02 (t, J=7.3 Hz, 1H), 3.76 (s, 3H).

EXAMPLE 76

6-(4-(3-methoxyphenyl)phenyl)imidazo[2,1-b]-1,3,4-thiadiazole-2-sulfonamide

Compound 76 was prepared in a manner similar to compound 73.

$^1$H NMR (200 MHz, DMSO-d$^6$) δ 8.94 (s, 1H), 8.73 (s, 2H), 7.97 (d, J=8.2 Hz, 2H), 7.74 (d, J=8.3 Hz, 2H), 7.34 (t, J=7.3 Hz, 1H), 7.26 (d, J=7.3 Hz, 1H), 7.23 (s, 1H), 6.92 (d, J=7.3 Hz, 1H), 3.81 (s, 3H).

EXAMPLE 77

6-(4-(4-trifluoromethylphenyl)phenyl)imidazo[2,1-b]-1,3,4-thiadiazole-2-sulfonamide Compound 77 was prepared in a manner similar to compound 73.

$^1$H NMR (200 MHz, DMSO-d$^6$) δ 8.91 (s, 1H), 8.73 (s, 2H), 7.96 (d, J=8.6 Hz, 2H), 7.70 (d, J=8.8 Hz, 2H), 7.66 (d, J=8.6 Hz, 2H), 7.02 (d, J=8.8 HZ, 2H), 3.80 (s, 3H).

EXAMPLE 78

6-(4-(3-trifluoromethoxyphenyl)phenyl)imidazo[2,1-b]-1,3,4-thiadiazole-2-sulfonamide Compound 78 was prepared in a manner similar to compound 73.

$^1$H NMR (200 MHz, DMSO-d$^6$) δ 9.00 (s, 1H), 8.75 (s, 2H), 8.01 (d, J=8.0 Hz, 2H), 7.79 (m, 3H), 7.69 (s, 1H), 7.59 (t, J=8.1 Hz, 1H), 7.35 (d, J=7.9 Hz, 1H).

EXAMPLE 79

6-(4-(hydroxymethylphenyl)phenyl)imidazo[2,1-b]-1,3,4-thiadiazole-2-sulfonamide

Compound 79 was prepared in a manner similar to compound 73. MS (m/z) M+1=401.

EXAMPLE 80

6-(4-(2-trifluoromethylphenyl)phenyl)imidazo[2,1-b]-1,3,4-thiadiazole-2-sulfonamide Compound 80 was prepared in a manner similar to compound 73.

$^1$H NMR (200 MHz, DMSO-d$^6$) δ 8.93 (s, 1H), 8.71 (s, 2H), 7.95 (d, 2H), 7.77 (d, 2H), 7.66 (t, 1H), 7.60 (t, 1H), 7.35 (m, 2H).

EXAMPLE 81

6-(4-(3-trifluoromethylphenyl)phenyl)imidazo[2,1-b]-1,3,4-thiadiazole-2-sulfonamide Compound 81 was prepared in a manner similar to compound 73.

$^1$H NMR (200 MHz, DMSO-d$^6$) δ 8.98 (s, 1H), 8.74 (s, 2H), 8.02 (m, 4H), 7.84 (d, J=8.2 Hz, 2H), 7.70 (m, 2H).

EXAMPLE 82

6-(4-(4-trifluoromethylphenyl)phenyl)imidazo[2,1-b]-1,3,4-thiadiazole-2-sulfonamide Compound 82 was prepared in a manner similar to compound 73.

$^1$H NMR (200 MHz, DMSO-d$^6$) δ 8.97 (s, 1H), 8.73 (s, 2H), 8.05–7.80 (m, 8H).

EXAMPLE 83

6-(4-(3,5-ditrifluoromethylphenyl)phenyl)imidazo[2,1-b]-1,3,4-thiadiazole-2-sulfonamide Compound 83 was prepared in a manner similar to compound 73.

$^1$H NMR (200 MHz, DMSO-d$^6$) δ 9.02 (s, 1H), 8.75 (s, 2H), 8.38 (s, 2H), 8.01 (m, 5H).

EXAMPLE 84

6-(thiophen-2-yl-phenyl)imidazo[2, 1-b]-1,3,4-thiadiazole-2-sulfonamide

Compound 84 was prepared in a manner similar to compound 73.

$^1$H NMR (200 MHz, DMSO-d6) δ 8.92 (s, 1H), 8.70 (s, 2H), 7.94 (d, J=8.2 Hz, 2H), 7.73 (d, J=8.2 Hz, 2H), 7.56 (m, 2H), 7.15 (m, 1H).

EXAMPLE 85

6-(thiophen-3-yl-phenyl)imidazo[2,1-b]-1,3,4-thiadiazole-2-sulfonamide

Compound 85 was prepared in a manner similar to compound 73.

$^1$H NMR (200 MHz, DMSO-d6) δ 8.79 (s, 1H), 8.72 (s, 2H), 7.88 (d, J=8.2 Hz, 2H), 7.16 (t, J=8.2 Hz, 1H), 7.03 (d, J=8.2 Hz, 2H), 6.49 (d, J=8.2 Hz, 1H), 6.38 (s, 1H), 6.27 (d, J=7.3 Hz, 1H), 2.86 (s, 6H).

Example 86

6-(4'methoxybiphen-3-yl)imidazo[2,1-b]-1,3,4-thiadiazole-2-sulfonamide

Compound 86 was prepared in a manner similar to compound 73.
$^1$H NMR (200 MHz, DMSO-d$^6$) δ 8.98 (s, 1H), 8.72 (s, 2H), 8.14 (s, 1H), 7.84 (d, J=7.3 Hz, 1H), 7.67 (d, J=8.5HZ, 2H), 7.54 (m, 2H), 7.05 (d, J=8.9Hz, 2H), 2.80 (s, 3H).

EXAMPLE 87

6-(4-phenoxyphenyl)imidazo[2,1-b]-1,3,4-thiadiazole-2-sulfonamide

Step 1: 4-Phenoxyacetopheneone was prepared by refluxing 4-fluoroaceotone and phenol in DMAc for 16 hours. The solvent was removed under reduced pressure and the reside subjected to standard ethyl acetate/water work-up and the resulting material purified by silica gel chromatography.

Step 2: 4-Phenoxyacetophenone was brominated with bromine according to Method A to provide the desired α-bromoacetophenone, which was condensed with 2-amino-13,4,-thiadiazole-5-sulfonamide according to method C, to provide compound 87 as an off white, solid. $^1$H NMR (200 MHz, DMSO-d$^6$) δ 8.82 (s, 1H), 8.71 (s, 2H), 7.90 (d, J=7.9 Hz, 2H), 7.40 (t, J=7.3 Hz, 2H), 7.07 (t, J=7.3 Hz, 1H), 7.08–7.03 (m, 6H).

EXAMPLE 88

6-(4-chlorophenoxyphenyl)imidazo[2,1-b]-1,3,4-thiadiazole-2-sulfonamide

Compound 88 was prepared in a manner similar to compound 87.
$^1$H NMR (200 MHz, DMSO-d$^6$) δ 8.81 (s, 1H), 8.72 (s, 2H), 7.89 (d, J=8.5 Hz, 2H), 7.23 (m, 2H), 7.11–7.01 (m, 4H).

EXAMPLE 89

6-(4-(3,4-difluorophenoxy)phenyl)imidazo[2,1-b]-1,3,4-thiadiazole-2-sulfonamide Compound 89 was prepared in a manner similar to that described for compound 87. MS (m/z) M+1=409.

EXAMPLE 90

6-(4-(4-azaphenoxy)phenyl)imidazo[2,1-b]-1,3,4-thiadiazole-2-sulfonamide

Compound 90 was prepared in a manner similar to that described for compound 87. $^1$H NMR (200 MHz, DMSO-d$^6$) δ 9.02, 8.76 (s, 2H), 8.41 (d, J=8.6 Hz, 2H), 8.10 (d, J=8.6 Hz, 2H), 7.71 (d, J=8.6 Hz, 2H), 7.01 (d, J=8.6 Hz, 2H).

EXAMPLE 91

6-(4-chlorophenoxyphenyl)imidazo[2,1-b]-1,3,4-thiadiazole-2-sulfonamide

Compound 91 was prepared in a manner similar to compound 87.
$^1$H NMR (200 MHz, DMSO-d$^6$) δ 8.84 (s, 1H), 8.72 (s, 2H), 7.92 (d, J=8.5 Hz, 2H), 7.44 (d, J=8.5 Hz, 2H), 7.08 (m, 4H).

EXAMPLE 92

6-(3,4-dichlorophenoxyphenyl)imidazo[2,1-b]-1,3,4-thiadiazole-2-sulfonamide

Compound 92 was prepared in a manner similar to compound 87.
$^1$H NMR (200 MHz, DMSO-d$^6$) δ 8.86 (s, 1H), 8.72 (s, 2H), 7.94 (d, J=8.5 Hz, 2H), 7.63 (d, J=8.9 Hz, 1H), 7.34 (d, J=2.7 Hz, 1H), 7.16 (d, J=8.9 Hz, 2H), 7.04 (dd, $^1$J=8.9 Hz $^2$J=2.8 Hz, 1H).

EXAMPLE 93

6-(2-bromophenoxyphenyl)imidazo[2,1-b]-1,3,4-thiadiazole-2-sulfonamide

Compound 93 was prepared in a manner similar to compound 87.
$^1$H NMR (200 MHz, DMSO-d$^6$) δ 8.82 (s, 1H), 8.72 (s, 2H), 7.90 (d, J=8.2 Hz, 2H), 7.74 (d, J=7.9 Hz, 1H), 7.37 (t, J=7.5 Hz, 1H), 7.15 (t, J=8.4 Hz, 2H), 7.00 (d, J=8.5 Hz, 2H).

EXAMPLE 94

6-(3-bromophenoxyphenyl)imidazo[2,1-b]-1,3,4-thiadiazole-2-sulfonamide

Compound 94 was prepared in a manner similar to compound 87. MS (m/z) M+1=452, M+2=454.

EXAMPLE 95

6-(4-bromophenoxypohenyl)imidazo[2,1-b]-1,3,4-thiadiazole-2-sulfonamide

Compound 95 was prepared in a manner similar to compound 87. $^1$H NMR (200 MHz, DMSO-d$^6$) δ 6.98–7.19 (m, 4H), 7.55 (d, 2H, J=8.5 Hz), 7,92 (d, 2H, J=8.5 Hz), 8.71 (s, 2H), 8.84 (s, 1H).

EXAMPLE 96

6-(3-dimethylaminophenoxyphenyl)imidazo[2,1-b]-1,3,4-thiadiazole-2-sulfonamide Compound 96 was prepared in a manner similar to compound 87.
$^1$H NMR (200 MHz, DMSO-d$^6$) δ 8.79 (s, 1H), 8.72 (s, 2H), 7.88 (d, J=8.2 Hz, 2H), 7.16 (t, J=8.2 Hz, 1H), 7.03 (d, J=8.2 Hz, 2H), 6.49 (d, J=8.2 Hz, 1H), 6.38 (s, 1H), 6.27 (d, J=7.3 Hz, 1H), 2.86 (s, 6H).

EXAMPLE 97

6-(4-(4-iso-propylphenoxy)phenyl)imidazo[2,1-b]-1,3,4-thiadiazole-2-sulfonamide Compound 97 was prepared in a manner similar to compound 87.
$^1$H NMR (200 MHz, DMSO-d$^6$) δ 8.81 (s, 1H), 8.72 (s, 2H), 7.89 (d, J=8.9 Hz, 2H), 7.26 (d, J=8.5 Hz, 2H), 7.03 (d, J=8.9 Hz, 2H), 6.97 (d, J=8.5 Hz, 2H), 2.88 (septet, J=6.9 Hz, 1H), 1.19 (d, J=6.7 Hz, 6H).

EXAMPLE 98

6-(4-(4-methoxyphenoxy)phenyl)imidazo[2,1-b]-1,3,4-thiadiazole-2-sulfonamide

Compound 98 was prepared in a manner similar to that described for compound 87. $^1$H NMR (200 MHz, DMSO-d$^6$) δ 8.79 (s, 1H), 8.71 (s, 2H), 7.84 (d, J8.8 Hz, 2H), 7.06–6.94 (m, 4H), 3.74 (s, 3H).

EXAMPLE 99

6-(4-(4-nitrophenoxy)phenyl)imidazo[2,1-b]-1,3,4-thiadiazole-2-sulfonamide

Compound 99 was prepared in a manner similar to compound 87.
$^1$H NMR (200 MHz, DMSO-d$^6$) δ 8.91 (s, 1H), 8.73 (s, 2H), 8.25 (d, J=8.9 Hz, 2H), 8.00 (d, J=8.2 Hz, 2H), 7.27 (d, J=8.5 Hz, 2H), 7.18 (d, J=8.9 Hz, 2H).

EXAMPLE 100

6-4-(3,4-difluorophenoxy)phenyl)imidazo[2,1-b]-1,3,4-thiadiazole-2-sulfonamide

Compound 100 was prepared in a manner similar to compound 87. MS (m/z) M+1=409.

EXAMPLE 101

Step 1: 4-Hydroxyacetophenone (5.00 g, 36.7 mmol) was dissolved in THF (100 mL) and cooled on ice. Sodium bis(trimethylsilyl)amide (40.5 mL, 1.0M in THF, 40.5 mmol) was added and the solution was warmed to room temperature. After stirring for 2 hours the solution was cooled on ice and ethyl bromoacetate (6.14 mL, 55.1 mmol) was added; The solution was stirred over night. Standard aqueous workup provided the desired ester as a clear oil, which was dissolved in 3:2:1 THF/methanol/1.0M NaOH (36 mL). After stirring over night the solution was diluted with diethyl ether and water. The aqueous layer was separated, washed with diethyl ether, and acidified. The resulting solid was extracted with ethyl acetate to provide 2-(4-acetylphenoxy)acetic acid as a white solid (2.91 g).
Step 2: 2-(4-acetylphenoxy)acetic acid (2.81 g, 14.5 mmol) was dissolved in acetic acid (100 mL) and treated with bromine (740 μL, 14.5 mmol) and stirred 48 hours. Bromine (370 mL, 7.25 mmol) was added and solution was stirred for an additional 16 hours. Volatiles were removed under reduced pressure to provide a brown solid which was titurated with diethyl ether to provide 2-(4-(2-bromoacetyl)phenoxy)acetic acid (1.82 g) as a light brown solid.
Step 3: 2-(4-(2-Bromoacetyl)phenoxy)acetic acid (1.00 g, 3.66 mmol) and 5-amino-1,3,4-thiadiazole-2-sulfonamide (659 mg, 3.66 mmol) were refluxed together in methanol (20 mL) for 48 hours. The resulting suspension was cooled to −10° C., filtered and the solid washed with cold methanol (3×5 mL) to provide compound 101 as a white crystalline solid (578 mg, 44%). $^1$H NMR (200 MHz, DMSO-d$^6$) δ 8.69 (s, 1H), 7.65 (d, 2H), 7.02 (d, 2H), 4.83 (s, 2H), 3.70 (s, 3H), 2.64 (s, 3H).

EXAMPLE 102

Compound 101 (50 mg, 0.14 mmol) was dissolved in 3:2:1 THF/methanol/1M NaOH (9 mL) and stirred over night. The resulting solution was diluted with ethyl acetate and water. The aqueous layer was washed with ethyl acetate and acidified to yield a white suspension. The suspension was extracted with ethyl acetate, the organic layer was dried over anhydrous MgSO$_4$, filtered, and the solvent removed under reduced pressure to provide compound 102 as a white solid (10.2 mg). $^1$H NMR (200 MHz, DMSO-d$^6$) δ 8.74 (s, 1H), 7.80 (d, J=8.8 Hz, 2H), 6.96 (d, J=8.8 Hz, 2H), 4.66 (s, 2H).

EXAMPLE 103

4-(2-Bromopropionyl)phenylacetic acid (256 mg, 1.0 mmol) and 5-amino-1,3,4-thiadiazole-2-sulfonamide (185 mg, 1.22 mmol) were refluxed together in methanol (20 mL) for 48 hours. The resulting suspension was cooled to −10° C., filtered and the solid washed with cold methanol (3×5 mL) to provide compound 103 as a white crystalline solid (22 mg, 7%). $^1$H NMR (200 MHz, DMSO-d$^6$) δ 8.69 (s, 1H), 7.65 (d, 2H), 7.02 (d, 2H), 4.83 (s, 2H), 3.70 (s, 3H), 2.64 (s, 3H).

EXAMPLE 104

6-(3-chloro-4-methylphenyl)-5-methylimidazo[2,1-b]-1,3,4-thiadiazole-2-sulfonamide 2-Bromo-1-(3-chloro-4-methylphenyl)propan-1-one (262 mg, 1.0 mmol) and 2-amino-1,3,4-thiadiazole-5-sulfonamide (180 mg, 1.0 mmol) were refluxed in ethanol (10 mL) for 5 days. The resulting solution was concentrated and the crude material was purified by column chromatography on silica gel, eluting with 25:75 ethyl acetate/hexanes to provide compound 104 as a yellow powder (38 mg, 11%). $^1$H NMR (200 MHz, DMSO-d$^6$) δ 8.72 (s, 2H), 7.74 (m, 1H), 7.59 (m, 1H), 7.48 (m, 1H), 2.68 (s, 3H), 2.39 (s, 3H).

EXAMPLE 105

6-(2-Pyridyl)imidazo[2,1-b]-1,3,4-thiadiazole-2-sulfonamide 2-(2-bromoacetyl)pyridine (2.5 g, 12.4 mmol) and 2-amino-1,3,4-thiadiazole-5-sulfonamide (2.2 g, 12.4 mmol) were refluxed in methanol (75 mL) for 48 hrs. After evaporation of methanol 1M sodium hydroxide (25 mL) was added and the resulting solution was washed with ether (3×20 mL). The aqueous layer was acidified to a pH of 7 with 1M hydrochloric acid and extracted with ethyl acetate (3×25 mL). The solid obtained from the organic layers was recrystallized in acetone to provide compound 105 as a light brown powder (84 mg, 2.4%). $^1$H NMR (200 MHz, DMSO-d$^6$) δ 8.82 (s, 1H), 8.74 (br s, 2H), 8.58 (d, J=5.5 Hz, 1H), 7.92 (m, 2H), 7.33 (m, 1H).

EXAMPLE 106

6-(2-Pyridyl)imidazo[2,1-b]-1,3,4-thiadiazole-2-sulfonamide HCl

Compound 105 (25 mg) was dissolved in methanol and HCl gas was bubbled through for 30 seconds. Volatiles were removed under reduced pressure to provide a white solid (99%). $^1$H NMR (200 MHz, D$_2$O-d$^6$) δ 8.86 (s, 1H), 8.57 (d, J=5.8 Hz, 1H), 8.50 (t, J=7.5 Hz, 1H), 8.27 (d, J=8.2 Hz, 1H), 7.80 (t, J=6.7 Hz, 1H).

EXAMPLE 107

6-(4-Pyridyl)imidazo[2,1-b]-1,3,4-thiadiazole-2-sulfonamide

2-Bromo-1-(4-pyridinyl)-1-ethanone hydrobromide (100 mg, 0.356 mmol) and 2-amino-1,3,4-thiadiazole-5-sulfonamide (64 mg, 0.356 mmol) were refluxed in 1,4-dioxane (5 mL) for 48 hours. The resulting solid was isolated by filtration and recrystallized from methanol to provide compounds 107 as a brown solid (129 mg, 42% yield). $^1$H NMR (200 MHz, DMSO-d$^6$)δ 9.52 (s, 1H), 8.90 (d, 2H), 8.84 (s, 2H), 8.39 (d, 2H).

EXAMPLE 108

6-(2-Pyrimidenyl)imidazo[2,1-b]-1,3,4-thiadiazole-2-sulfonamide

Step 1: Acetylpyrazine (244 mg, 2.0 mmol) was suspended in glacial acetic acid (10 mL) and treated with pyridinium tribromide (640 mg, 2.0 mmol). The reaction mixture was stirred overnight. The solvent was removed under reduced pressure and the residue was purified by silica gel chromatography, eluting with 1:1 hexane/ethyl acetate, to provide 2-(2-bromoacetyl)pyrazine as a brown solid (154 mg, 38%). $^1$H NMR (200 MHz, DMSO-d$^6$) δ 9.16 (d, J=1.5 Hz, 1H), 8.94 (d, J=2.4 Hz, 1H), 8.82 (dd, J=1.5, 2.4 Hz, 1H), 4.99 (s, 2H).

Step 2 2-(2-Bromoacetyl)pyrazine (154 mg, 0.764 mmol) and 5-amino-1,3,4-thiadiazole-2-sulfonamide (138 mg, 0.764 mmol) were refluxed together in methanol (10 mL) for 48 hours. The resulting suspension was cooled to −10° C., filtered and the solid washed with cold methanol (3×2 mL) to provide compound 108 as a brown solid (6.6 mg, 3.1%). $^1$H NMR (200 MHz, DMSO-d$^6$) δ 9.19 (s, 1H), 8.98 (s, 1H), 8.78 (s, 2H), 8.65 (d, J=1.5 Hz, 1H), 8.59 (d, J=2.7 Hz, 1H).

EXAMPLE 109

6-(coumaran-2-yl)imidazo[2,1-b]-1,3,4-thiadiazole-2-sulfonamide 2-(2-Bromoacetyl)coumaran (mg, 1.0 mmol) and 5-amino-i ,3,4-thiadiazole-2-sulfonamide (180 mg, 1.0 mmol) were refluxed together in methanol (10 mL) for 72 hours. The resulting suspension was cooled to −10° C., filtered and the solid washed with cold methanol (3×2 mL) to provide compound 109 as a white solid (15.6 mg, 5.4%).
$^1$H NMR(200 MHz, DMSO-d$^6$) δ 8.79 (s, 1H), 8.65 (br s, 1H), 8.61 (s, 1H), 7.81 (d, J=7.6 Hz, 1H), 7.58 (m, 1H), 7.38 (m, 2H). $^{13}$C NMR (50 MHz, DMSO-d$^6$) δ 164.7, 158.5, 152.5, 139.9, 137.5, 131.9, 128.9, 124.8, 119.8, 119.1, 116.0, 114.6, 96.7.

EXAMPLE 110

6-(Chloroacetyl)-2-H-1,4-benzoxazin-3(4H)-one (248 mg, 1.1 mmol), n-Bu$_4$NI (405 mg, 1.1 mmol) and 5-amino-1,3,4-thiadiazole-2-sulfonamide (148 mg, 1.0 mmol) were refluxed together in methanol (12 mL) for 4 days. The resulting precipitate was isolated by filtration, washing with cold methanol, to provide compounds 110 as a white solid (58 mg). $^1$H NMR (200 MHz, DMSO-d$^6$) δ 10.84 (s, 1H), 8.79 (s, 3H), 7.48 (s, 1H), 7.42 (d, 2H), 7.00 (d, 2H), 4.58 (s, 2H).

EXAMPLE 111

6-(Benzo[b]furan-2-yl)imidazo[2,1-b]-1,3,4-thiadiazole-2-sulfonamide 1-(1-benzofuran-2-yl)-2-bromoethan-1-one (100 mg, 0.41 mmol) and 2-amino-1,3,4-thiadiazole-5-sulfonamide (74 mg, 0.41 mmol) were refluxed in ethanol (5 mL) for 30 hrs. The resulting solution was cooled on ice and the resulting precipitate was collected by filtration to provide compound 111 as an off white powder (47 mg, 33%). $^1$H NMR (200 MHz, DMSO-d$^6$) δ 8.86 (s, 1H), 8.77 (br s, 2H), 7.65 (m, 2H), 7.29 (m, 3H).

EXAMPLE 112

6-(2-Thiophenyl)-imidazo[2,1-b]-1,3,4-thiadiazole-2-sulfonamide

2-Acetylthiophene (252 mg, 2.0 mmol) was dissolved in acetic acid (5 mL) and treated with bromine (100 μL, 2.0 mmol). The solution was stirred overnight before the volatiles were removed under reduced pressure to provide a white solid, which contained a 3:1 mixture of (2-bromoacetyl)thiophene and starting material. This crude mixture was refluxed in methanol (10 mL) with 5-amino-1,3,4-thiadiazole-2-sulfonamide (300 mg, 2.0 mmol) for 5 days. The resulting solid was filtered, washing with methanol (3×5 mL) to provide compounds 112 as a light pink solid (60.5 mg). $^1$H NMR (200 MHz, DMSO-d$^6$) δ 8.70 (s, 1H), 7.48 (m, 2H), 7.11 (t, 1H).

EXAMPLE 113

6-(5-Phenylthiophen-2-yl)-imidazo[2,1-b]-1,3,4-thiadiazole-2-sulfonamide

2-Bromo-1-(5-phenyl-2-thienyl)-1-ethanone (100 mg, 0.36 mmol) and 2-amino-1,3,4-thiadiazole-2-sulfonamide were refluxed in ethanol for 120 hours. The volatiles were removed in vacuo. The residue was purified by column chromatography on silica gel using 20% ethyl acetate/1% acetic acid in hexane followed by 30% ethyl acetate/1% acetic acid in hexane as eluant. Triturating with diethyl ether provided compound 113 (7 mg) as an orange solid. $^1$H NMR (200 MHz, DMSO-d$^6$) δ 8.82 (s, 1H), 8.70 (br s, 2H), 7.70–7.20 (m, 7H).

EXAMPLE 114

6-(5-Nitro-2-thiophenyl)-imidazo[2,1-b]-1,3,4-thiadiazole-2-sulfonamide hydrobromide

EXAMPLE 115

6-(3-Methylbenzo[b]thiophen-2-yl)imidazo[2,1-b]-1,3,4-thiadiazole-2-sulfonamide 2-Bromo-1-(3-methylbenzo[b]thiophen-2-yl)ethan-1-one (125 mg, 0.5 mmol) and 2-amino-1,3,4-thiadiazole-5-sulfonamide (74 mg, 0.5 mmol) were refluxed in ethanol (10 mL) for 72 hrs. The resulting solution was cooled on ice and the resulting precipitate was collected by filtration to provide compound 115 as a white crystalline solid (63 mg, 39%). $^1$H NMR (200 MHz, DMSO-d$^6$) δ 8.80 (s, 1H), 8.78 (s, 2H), 8.94 (dd, 1H), 8.83 (dd, 1H), 7.42 (dt, 1H), 7.37 (dt, 1H), 2.58 (s, 3H).

EXAMPLE 116

6-(Benzo[b]thiophen-3-yl)imidazo[2,1-b]-1,3,4-thiadiazole-2-sulfonamide

1-Benzo[b]thiophen-3-yl-2-bromoethan-1-one (125 mg, 0.5 mmol) and 2-amino-1,3,4-thiadiazole-5-sulfonamide (74 mg, 0.5 mmol) were refluxed in ethanol (10 mL) for 72 hrs. The resulting solution was cooled on ice and the resulting precipitate was collected by filtration to provide compound 116 as a white crystalline solid (63 mg, 39%). $^1$H NMR (200 MHz, DMSO-d$^6$) δ 8.91 (s, 1H), 8.74 (br s, 2H), 8.52 (d, 1H), 8.13 (s, 1H), 8.05 (d, 1H), 7.50–7.42 (m, 2H).

EXAMPLE 117

6-(3-Phenylisoxazol-5-yl)imidazo[2,1-b]-1,3,4-thiadiazole-2-sulfonamide

Prepared according to Method C. $^1$H NMR (200 MHz, DMSO-d$^6$) δ 9.03 (s, 1H), 8.79 (s, 2H), 7.95 (m, 3H), 7.53 (m, 2H), 7.36 (s, 3H).

EXAMPLE 118

6-(5-Methyl-3-phenylisoxazol-4-yl)imidazo[2,1-b]-1,3,4-thiadiazole-2-sulfonamide 2-Bromo-1-(5-methyl-3-phenylisoxazol-4-yl)ethan-1-one (100 mg, 0.36 mmol) and 2-amino-1,3,4-thiadiazole-5-sulfonamide (65 mg, 0.36 mmol) were refluxed in ethanol (5 mL) for 60 hrs. Solvent was evaporated and the crude solid was purified by flash chromatography using 35:65 ethyl acetate:hexanes to provide compound 118 as a yellowish powder (64 mg, 50%). $^1$H NMR (200 MHz, DMSO-d$^6$) δ 8.73 (br s, 2H), 8.25 (s, 1H), 7.58 (m, 2H), 7.45 (m, 3H), 2.56 (s, 3H).

EXAMPLE 119

6-(Ethyl isoxazol-5-yl-3-carboxylate)imidazo[2,1-b]-1,3,4-thiadiazole-2-sulfonamide Ethyl 5-(2-bromoacetyl)isoxazole-3-carboxylate (100 mg, 0.38 mmol) and 2-amino-1,3,4-thiadiazole-5-sulfonamide (70 mg, 0.38 mmol) were refluxed in ethanol (5 mL) for 60 hrs. The resulting solution was cooled on ice and the resulting precipitate was collected by filtration to provide compound 119 as an orange powder (21 mg, 16 %). $^1$H NMR (200 MHz, DMSO-d$^6$) δ 9.14 (s, 1H), 8.82 (s, 2H), 7.16 (s, 1H), 4.39 (q, J=7.0 Hz, 2H), 1.34 (t, J =7.1 Hz, 3H).

EXAMPLE 120

6-(5-methyl-1-phenyl-1H-pyrazol-4-yl)imidazo[2,1-b]-1,3,4-thiadiazole-2-sulfonamide 2-Bromo-1-(5-methyl-1-phenyl-1H-pyrazol-4-yl)ethan-1-one (100 mg, 0.36 mmol) and 2-amino-1,3,4-thiadiazole-5-sulfonamide (65 mg, 0.36 mmol) were refluxed in ethanol (5 mL) for 45 hrs. Solvent was evaporated and the solid was recrystallized from ethanol to provide compound 120 as a beige powder (30 mg, 28%). $^1$H NMR (200 MHz, DMSO-d$^6$) δ 8.71 (s, 2H), 8.55 (s, 1H), 7.98 (s, 1H), 7.52 (m, 5H), 2.56 (s, 3H).

EXAMPLE 121

6-(Thiaxol-2-yl)imidazo[2,1-b]-1,3,4-thiadiazole-2-sulfonamide

Step 1 2-Acetylthiazole (400 μL, 3.86 mmol) was suspended in chloroform (10 mL) and treated with pyridinium tribromide (1.23 g, 3.86 mmol). The reaction mixture was stirred for two days. The solvent was removed under reduced pressure. Standard aqueous/ethyl acetate workup provided a dark orange solid, which was identified as a 8:1 mixture of 2-(2-bromoacetyl)thiazole and starting material. $^1$H NMR (200 MHz, DMSO-d$^6$) δ 8.30 (d, J=2.1 Hz, 1H), 8.18 (d, J=2.1 Hz, 1H), 4.93 (s, 2H).

Step 2 2-(2-Bromoacetyl)thiazole (206 mg, 1.0 mmol) and 5-amino-1,3,4-thiadiazole-2-sulfonamide (180 mg, 1.0 mmol) were refluxed together in methanol (10 mL) for 72 hours. The resulting suspension was cooled to −10° C., filtered and the solid washed with cold methanol (3×2 mL) to provide compound 121 as a white solid (15.6 mg, 5.4%). $^1$H NMR (200 MHz, DMSO-d$^6$) δ 8.90 (s, 1H), 8.74 (br s, 2H), 7.90 (d, J=3.1 Hz, 1H), 7.75 (d, J=3.3 Hz, 1H).

EXAMPLE 122

6-(2,4-Thiaxol-5-yl)imidazo[2,1-b]-1,3,4-thiadiazole-2-sulfonamide

Compound 122 was prepared according to the method described for compound 103 to provide compound 122 as an off white solid. $^1$H NMR (200 MHz, DMSO-d$^6$) δ 8.74 (s, 2H), 8.65 (s, 1H), 2.63 (s, 3H), 2.47 (s, 3H).

EXAMPLE 123

5-Chloro-6-phenyl-imidazo[2,1-b]-1,3,4-thiadiazole-sulfonamide

Compound 1 (250 mg, 0.891 mmol) was dissolved in 10:1 THF/water (22 mL) and treated with 40% sodium hypochlorite (1 mL). The solution was stirred for 3 hours before the volatiles were removed under reduced pressure to provide a light yellow solid (310 mg, 98%). $^1$H NMR (200 MHz, DMSO-d$^6$) δ 7.96 (m, 2H), 7.43 (t, 2H), 7.39 (t, 1H).

EXAMPLE 124

5-Bromo-6-phenyl-imidazo[2,1-b]-1,3,4-thiadiazole-2-sulfonamide hydrobromide

Compound 1 (5.00 g, 17.8 mmol) in AcOH (200 mL) was treated with bromine (0.96 mL, 18.7 inmol). The solution was stirred overnight and the formation of a white precipitate was observed. The solvent was evaporated and the solid was suspended in MeOH (50 mL). That suspension was put in the fridge for one hour and filtered to provide compound 124 as a white powder (4.8 g, 76% after 3$^{rd}$ crop). $^1$H NMR (200 MHz, DMSO) : δ 8.82 (s, 2H), 7.98 (d, J=8.2 Hz, 2H), 7.46 (m, 3H).

EXAMPLE 125

5-Bromo-6-(2-pyridyl)imidazo[2,1-b]-1,3,4-thiadiazole-2-sulfonamide hydrobromide Compound 105 (50 mg, 0.18 mmol) was suspended in acetic acid (5 mL) and treated with bromine (10 μL, 0.20 mmol). After stirring overnight the volatiles were removed under reduced pressure and the solid was dried under vacuum to provide compound 125 as a yellow solid (54 mg, 84%). $^1$H NMR (200 MHz, DMSO-d$^6$) δ 8.84 (s, 2H), 8.67 (d, J=4.6 Hz, 1H), 8.02 (m, 2H), 7.43 (m, 1H); $^{13}$C NMR (50 MHz, DMSO) δ 166.9, 147.1, 146.0, 142.6, 137.9, 124.8, 122.4, 98.7.

EXAMPLE 126

5-Bromo-6-(4-nitrophenyl)imidazo[2,1-b]-1,3,4-thiadiazole-2-sulfonamide hydrobromide

EXAMPLE 127

5-Bromo-6-(4-chlorophenyl)imidazo[2,1-b]-1,3,4-thiadiazole-2-sulfonamide hydrobromide

EXAMPLE 128

5-Bromo-6-(4-bromophenyl)imidazo[2,1-b]-1,3,4-thiadiazole-2-sulfonamide hydrobromide Compound 14 (100 mg, 0.278 mmol) was suspended in acetic acid (5 mL) and treated with neat bromine (16 μL, 0.306 mmol). The reaction mixture was stirred overnight and volatiles were removed under reduced pressure to provide compounds 128 as a light orange solid (143 mg, 99%). $^1$H NMR (200 MHz, DMSO-d$^6$) δ 8.82 (s, 2H), 7.92 (d, 2H), 7.68 (d, 2H).

EXAMPLE 129

5-Bromo-6-(2-bromo3-methoxyphenyl)imidazo[2,1-b]-1,3,4-thiadiazole-2-sulfonamide hydrobromide Prepared according to the method described for compound 128.

EXAMPLE 130

5-Bromo-6-(2-naphthyl)imidazo[2,1-b]-1,3,4-thiadiazole-2-sulfonamide hydrobromide Compound 62 (192 mg, 0.582 mmol) was suspended in acetic acid (10 mL) and treated with neat bromine (31 μL, 0.612 mmol). After stirring overnight the volatiles were removed under reduced pressure, to provide compound 130 as a tan solid (279 mg, 93%). $^1$H NMR (200 MHz, DMSO-d$^6$) δ 8.83 (br s, 2H), 8.42 (s, 1H), 8.04 (d, 1H), 7.98–7.80 (m, 3H), 7.48 (m, 2H).

EXAMPLE 131

5-Chloro-6-(biphenyl)imidazo[2,1-b]-1,3,4-thiadiazole-2-sulfonamide hydrobromide Compound 131 was prepared according to the method described for compound 123 to provide a white solid.

EXAMPLE 132

5-Bromo-6-(biphenyl)imidazo[2,1-b]-1,3,4-thiadiazole-2-sulfonamide hydrobromide

Compound 72 (1.00 g, 2.80 mmol) was suspended in AcOH (20 mL) and treated with bromine (172 μL, 3.4 mmol). The solution was stirred overnight and the formation of a white precipitate was observed. The solvent was evaporated and the solid was dissolved in 10 mL MeOH. That suspension was put in the fridge for one hour to increase precipitation. Successive precipitations and filtrations provided compound 132 as a yellow powder (1.10 g, 79%). $^1$H NMR (200 MHz, DMSO) δ 8.82 (s, 1H), 8.11 (d, J=8.5 Hz, 2H), 7.82 (d, J=8.6 Hz, 2H), 7.74 (d, J=8.5 Hz, 2H), 7.45 (m, 3H).

EXAMPLE 133

5-Bromo-6-(5-nitrothiophen-2-yl)imidazo[2,1-b]-1,3,4-thiadiazole-2-sulfonamide hydrobromide

EXAMPLE 134

5-Bromo-6-trifluoromethylimidazo[2,1-b]-1,3,4-thiadiazole-2-sulfonamide

Compound 59 (430 mg, 1.59 mmol) was suspended in acetic acid (10 mL) and treated with bromine (244 μL, 4.76 mmol). After stirring stirring overnight the volatiles were removed under reduced pressure to provide a 1:1 mixture of compounds 59 and 134 The above process was repeated to provide compound 134 as a white solid (477 mg). $^1$H NMR (200 MHz, DMSO-d$^6$) δ 8.89 (s, 2H).

EXAMPLE 135

5-Thiophenyl-6-(2-naphthyl)imidazo[2,1-b]-1,3,4-thiadiazole-2-sulfonamide

Compound 130 (100 mg, 0.204 mmol) and mercaptobenzene (28 uL, 0.269 mmol) were combined in THF (10 mL) and refluxed for 16 hours, followed by 72 hours at room temperature. Volatiles were removed under reduced pressure and the resulting residue was triturated with diethyl ether to provide compound 135 as a yellow solid (62 mg, 69% yield). $^1$H NMR (200 MHz, DMSO-d$^6$) δ 8.82 (br s, 2H), 8.58 (s, 1H), 8.19 (d, 1H), 7.92 (d, 1H), 7.83 (m, 2H), 7.53 (m, 2H), 7.38–7.12 (m, 5H).

EXAMPLE 136

5-(S-(2-Thio-5-amino-1,3,4-thiadiazolyl)-6-(2-naphthyl)imidazo[2,1-b]-1,3,4-thiadiazole-2-sulfonamide Compound 130 (102 mg, 0.208 mmol) and 5-amino-1,3,4-thiadiazole-2-thiol (37 mg, 0.275 mmol) were combined in a 2:1 mixture of ethyl acetate/methanol (15 mL) and refluxed for 16 hours, followed by 72 hours at room temperature. Volatiles were removed under reduced pressure and the resulting residue was recrystallized from methanol to provide compound 136 as a yellow solid (32 mg, 34% yield). $^1$H NMR (200 MHz, DMSO-d$^6$) δ 8.86 (br s, 2H), 8.66 (s, 1H), 8.28 (d, 1H), 8.02 (d, 1H), 7.98 (m, 2H), 7.57 (m, 2H), 7.36 (br s, 2H).

EXAMPLE 137

6-Phenyl-imidazo[2,1-b]-1,3,4-thiadiazole-2-N-methylsulfonamide

Compound 1 (110 mg, 0.50 mmol), methanol (30 mg, 0.5 mmol), and triphenylphosphine (130 mg, 0.5 mmol) were combined in THF (5 mL). This solution was added to a reaction vessel containing polymer supported DIAD (500 mg, 0.50 mmol). After being shaken overnight, the solid resin was removed by filtration and the filtrate was concentrated under reduced pressure. The resulting semi-solid was purified by silica gel chromatography, eluting with 10% ethyl acetate/hexane, to provide compound 137 as a white solid. $^1$H NMR (200 MHz, acetone-d$^6$) δ 8.58 (s, 1H), 7.98 (d, 2H), 7.42 (t, 2H), 7.31 (t, 1H), 2.93 (s, 3H).

EXAMPLE 138

6-(2,3,4,5,6-pentafluorophenyl)imidazo[2,1-b]-1,3,4-thiadiazole-2-N-methylsulfonamide MS (m/z) M+1=385.

EXAMPLE 139

6-Phenyl-imidazo[2,1-b]-1,3,4-thiadiazole-2-N,N-dimethylsulfonamide

Compound 1 (140 mg, 0.5 mmol), methanol (64 mg, 2.0 mmol), and triphenylphosphine (525 mg, 2.0 mmol) were combined in THE (2 mL) and treated with DIAD (200 µL, 2.0 mmol). The resulting solution was stirred over night. The resulting solid was filtered and washed with THF (2×3 mL) to provide compound 139 as a white crystalline solid. $^1$H NMR (200 MHz, DMSO-d$^6$) δ 8.92 (s, 1H), 8.91 (d, 2H), 7.44 (t, 2H), 7.34 (t, 1H), 2.93 (s, 6H).

EXAMPLE 140

6-(2,3,4,5,6-pentafluorophenyl)imidazo[2,1-b]-1,3,4-thiadiazole-2-N,N-dimethylsulfonamide Compound 140 was prepared in a manner similar to compound 137. $^1$H NMR (200 MHz, DMSO-d$^6$) δ 8.86 (t, 1H), 2.95 (s, 6H).

EXAMPLE 141

6-(3-Methoxyphenyl-imidazo[2,1-b]-1,3,4-thiadiazole-2-N,N-diethylsulfonamide

Compound 16 (50 mg, 0.162 mmol), ethanol (28 µL, 0.486 mmol), and triphenylphosphine (127 mg, 0.86 mmol) were combined in THF (10 mL) and treated with DIAD (96 µL, 0.468 mmol). The resulting solution was stirred over night. Solvent was removed under reduced pressure and the resulting semi-solid was triturated with diethyl ether to provide compound 141 as a white crystalline solid (19.6 mg, 33%). $^1$H NMR (200 MHz, CDCl$_3$) δ 8.06 (s, 1H), 7.38 (d, 2H), 7.35 (t, 1H), 6.88 (d, 1H), 3.88 (s, 3H), 3.45 (q, 4H), 1.35 (t, 6H).

EXAMPLE 142

6-(3-Methoxyphenyl)imidazo[2,1-b]-1,3,4-thiadiazole-2-N,N-dibutylsulfonamide

Compound 16 (50 mg, 0.162 mmol), butanol (44 µL, 0.486 mmol), and triphenylphosphine (127 mg, 0.486 mmol) were combined in THF (10 mL) and treated with DIAD (96 µL, 0.486 mmol). The resulting solution was stirred over night. The solvent was removed under reduced pressure and the resulting semi-solid was purified by silica gel chromatography, eluting with 10% ethyl acetate/hexane, to provide compound 142 as a light yellow solid (49 mg, 72%). $^1$H NMR (200 MHz, CDCl$_3$) δ 8.08 (s, 1H), 7.38 (d, 2H), 7.35 (t, 1H), 3.89 (s, 3H), 3.34 (t, 4H), 1.67 (m, 4H), 1.36 (m, 3H), 0.93 (t, 6H).

EXAMPLE 143

6-(4-Bromophenyl)imidazo[2,1-b]-1,3,4-thiadiazole-2-N,N-dimethylsulfonamide

Compound 143 was prepared from compound 14 according to the method described for compound 142.

EXAMPLE 144

6-(4-Bromophenyl)imidazo[2,1-b]-1,3,4-thiadiazole-2-N,N-dimethylsulfonamide hydrobromide 6-(4-Bromophenyl)imidazo[2,1-b]-1,3,4-thiadiazole-2-N,N-dimethylsulfonamide (100 mg, 0.258 mmol) was suspended in acetic acid (5 mL) and treated with neat bromine (18 µL, 0.315 mmol). The reaction mixture was stirred overnight and volatiles were removed under reduced pressure to provide compounds 144 as a light orange solid (140 mg, 99%). $^1$H NMR (200 MHz, DMSO-d$^6$) δ 7.84 (d, 2H), 7.63 (d, 2H), 2.93 (s, 6H).

EXAMPLE 145

6-(3-Hydroxyphenyl-imidazo[2,1-b]-1,3,4-thiadiazole-2-N,N-dimethylsulfonamide

Step 1: Compound 16 (212 mg, 0.851 mmol), methanol (103 µL. 2.55 mmol), and triphenylphosphine (669 mg, 2.55 mmol) were combined in THF (10 mL) and treated with DIAD (502 uL, 2.55 mmol). The resulting solution was stirred over night. Solvent was removed under reduced pressure and the resulting semi-solid was triturated with methanol to provide white crystalline solid (244 mg, 85%). $^1$H NMR (200 MHz, DMSO-d$^6$) δ 8.12 (s, 1H), 7.40 (dd, 1H), 7.38 (d, 1H), 7.33 (t, 1H), 6.88 (ddd, 1H), 3.87 (s, 3H), 3.02 (s, 6H).

Step 2: The above compound (420 mg, 1.24 mmol) was suspended in methylenechloride (10 mL) and treated with a BBr$^3$ (6.20 mL, 1.0 M in CH$_2$Cl$_2$, 6.20 mmol). The reaction mixture was stirred overnight before being quenched with water (1 mL), followed by saturated NaHCO$_3$ (10 mL). The resulting mixture was diluted with ethyl acetate (20 mL) and subjected to standard workup. The organic layer provided a off yellow solid which was further purified by recrystallization from methanol to provide compounds 145 was a gray solid (14 mg, 32%). $^1$H NMR (200 MHz, DMSO-d$^6$) δ 9.50 (br s, 1H), 8.83 (s, 1H), 7.30 (m, 2H), 7.25 (t, 1H), 6.71 (dd, 1H), 2.93 (s, 6H).

EXAMPLE 146

6-(3-Benzoyloxyphenyl)imidazo[2,1-b]-1,3,4-thiadiazole-2-N,N-dimethylsulfonamide Compound 145 (20 mg, 0.062 mmol) was dissolved in THF (2 mL) and treated with triethylamine (10 mL, 0.068 mmol) followed by benzoyl chloride (9 mL, 0.068 mmol). The reaction mixture was stirred for 4 hours before a second equiv of triethylamine and benzoyl chloride were added. Standard aqueous workup and purification by silica gel chromatography, eluting with 30% ethyl acetate/hexane, provided compound 146 as a white solid (16 mg, 62%). $^1$H NMR (200 MHz, CDCl$_3$) δ 8.22 (m, 2H), 8.12 (s, 1H), 7.77–7.60 (m, 3H), 7.58–7.44 (m, 3H), 7.22 (m, 1H).

EXAMPLE 147

6-(2-Naphthyl)imidazo[2,1-b]-1,3,4-thiadiazole-2-N,N-dimethylsulfonamide

Compound 62 (330 mg, 1.0 mmol), methanol (180 µL, 4.40 mmol), and triphenylphosphine (1.15 g, 4.40 mmol) were combined in THF (10 mL) and treated with DIAD (1.90 mL, 4.40 mmol). The resulting solution was stirred over night. The solvent was removed under reduced pressure and the resulting semi-solid was triturated with diethyl ether, to provide compound 147 as a white crystalline solid (268 mg, 75%). $^1$H NMR (200 MHz, DMSO-d$^6$) δ 9.02 (s, 1H), 8.45 (s, 1H), 8.07–7.83 (m, 3H), 7.56 (m, 2H), 2.91 (s, 6H).

EXAMPLE 148

6-Phenyl-imidazo[2,1-b]-1,3,4-thiadiazole-2-sulfonamide sodium salt

Compound 1 (200 mg, 0.71 mmol) was added to a solution of sodium hydroxide (28 mg, 0.71 mmol) in 4:1 MeOH/H$_2$O (5 mL). The solution was stirred overnight at room temperature before the solvent was removed under reduced pressure to provide compound 148 as a white solid (235 mg, 99%). $^1$H NMR (200 MHz, DMSO-d$^6$) δ 8.59 (s, 1H), 7.85 (d, J =8.2 Hz, 2H), 7.32 (in, 3H).

EXAMPLE 149

6-(3'-methoxybiphen-4-yl)imidazo[2,1-b]-1,3,4-thiadiazole-2-sulfonamide sodium salt Compound 149 was prepared from compound 76 according to the method described for compound 148; white solid (96%). $^1$H NMR (200 MHz, DMSO-d$^6$) δ 8.65 (s, 1H), 7.93 (d, J=8.8 Hz, 2H), 7.70 (d, J=8.8 Hz, 2H), 7.36 (m, 2H), 7.24 (s, 1H), 6.90 (d, J=6.4 Hz, 1H), 3.81 (s, 3H).

EXAMPLE 150

6-(3'-trifluoromethylbiphen-4-yl)imidazo[2,1-b]-1,3,4-thiadiazole-2-sulfonamide sodium salt Compound 150 was prepared from compound 81 according to the method described for compound 148; white solid (96%). $^1$H NMR (200 MHz, DMSO-d$^6$) δ 8.71 (s, 1H), 7.98 (m, 4H), 7.79 (d, J=8.2 Hz, 2H), 7.69 (m, 2H).

EXAMPLE 151

6-(4-Azido-2,3,5,6-tetraflourophenyl)imidazo[2,1-b]-1,3,4-thiadiazole-2-sulfonamide 2-Bromo-4'-azido-2',3',5',6'-tetrafluoroacetophenone (Keana, J. F. W.; Cai, S. X. J. *Org. Chem.*, 1990, 55, 3640) (353 mg, 1 mmol) and 2-amino-1,3,4-thiadiazole-5-sulfonamide (148 mg, 1 mmol) were refluxed in ethanol (10 mL) for 60 hours. The resulting solid was filtered, washing twice for cold methanol (2 mL), to provide compound 151 (102 mg, 25%) as a white powder. $^1$H NMR (200 MHz, DMSO-d$^6$) δ 8.81 (t, J=2.0 Hz, 1H), 8.79 (br s, 2H).

EXAMPLE 152

6-(4-azido-2,3,5,6-pentafluorophenyl)imidazo[2,1-b]-1,3,4-thiadiazole-2-N,N-dimethylsulfonamide Compound 152 was prepred in a manner similar to compound 137. $^1$H NMR (200 MHz, DMSO-d$^6$) δ 8.22 (t, 1H), 3.07 (s, 6H).

EXAMPLE 153

6-(4-Nitrophenyl)imidazo[2,1-b]-1,3,4-thiadiazole-2-sulfonamide

2-Bromo-4'-nitroacetophenone (2.44 g, 10.0 mmol) and 2-amino-1,3,4-thiadiazole-5-sulfonamide (1.50 g, 10.0 mmol) were refluxed in 1,4-dioxane (20 mL) for 48 hrs. The resulting solution was cooled on ice and the resulting precipitate was collected by filtration to provide compound 153 as a white crystalline solid (2.40 g, 67%). $^1$H NMR (200 MHz, DMSO-d$^6$) δ 9.18 (s, 1H), 8.69 (br s, 1H), 8.35 (d, 2H), 8.16 (d, 2H).

EXAMPLE 154

Protection of SCG Neurons from Anti-NGF Killing

SCG neurons were isolated from day 1 neonatal Sprague Dawley rats, plated at a cell density of 5,000 cells/well, and incubated in Biowhittaker Utraculture containing 1% Pen-strep, 1% L-glutamine, 0.7% ARAC, 3% rat serum, and NGF (50 ng/mL, Calomone Labs), at 37° C., under a 5% CO$_2$ atmosphere. After 4 days the cells were treated with anti-NGF antibody (Sigma). At this time compound was added and the cells were maintained serum and NGF free for 48 hours, at which time viability was assessed using Alamar Blue (Medicorp) staining.

Table 3a summarizes selected IC(50) values from compounds tested using this protocol.

TABLE 3a

| Rescue from anti-NGF killing of SCG neurons | |
|---|---|
| Compound | IC(50) (uM)* |
| 1 | 22 |
| 2 | 20 |
| 3 | 10 |
| 9 | 8 |
| 21 | 22 |
| 23 | 25 |
| 26 | 23 |
| 34 | >30 |
| 35 | >30 |

TABLE 3a-continued

Rescue from anti-NGF killing of SCG neurons

| Compound | IC(50) (uM)* |
|---|---|
| 36 | 17 |
| 72 | 17 |
| 74 | 20 |
| 75 | 10 |
| 76 | 5 |
| 79 | 7 |
| 81 | 5 |
| 82 | 25 |
| 84 | >30 |
| 85 | >30 |
| 86 | 17 |
| 87 | 10 |
| 88 | 10 |
| 89 | 10 |
| 91 | 7 |
| 92 | 7 |
| 93 | 7 |
| 94 | 10 |
| 95 | 7 |
| 96 | 20 |
| 97 | 7 |
| 98 | 17 |
| 99 | 7 |
| 106 | 7 |
| 111 | 7 |
| 148 | 22 |
| 149 | 7 |
| 150 | 7 |

*+/−1 uM

EXAMPLE 155

In Vitro Protection of SCG Neurons from Taxol Killing

SCG neurons were isolated from day 1 neonatal Sprague Dawley rats, plated at a cell density of 10,000 cells/well, and incubated in Biowhittaker Utraculture containing 1% Pen-strep, 1% L-glutamine, 0.7% ARAC, 3% rat serum, and NGF (50 ng/mL, Calomone Labs) at 37° C., under a 5% $CO_2$ atmosphere. After 5 days the cells were treated with compound and Taxol™ (50 ng/mL). Viability was assessed 48 hours later using MTS (Promega) staining.

Table 3b summarizes selected IC(50) values from compounds tested using this protocol.

TABLE 3b

Rescue from anti-NGF killing of SCG neurons

| Compounds | IC(50) (uM)* |
|---|---|
| 1 | 7 |
| 4 | 5 |
| 5 | 5 |
| 6 | 3 |
| 7 | 4 |
| 8 | 5 |
| 11 | 3 |
| 12 | 5 |
| 13 | 7 |
| 14 | 5 |
| 15 | 10 |
| 16 | 5 |
| 17 | 3 |
| 18 | 20 |
| 19 | 15 |
| 20 | 15 |

TABLE 3b-continued

Rescue from anti-NGF killing of SCG neurons

| Compounds | IC(50) (uM)* |
|---|---|
| 21 | 7 |
| 22 | 25 |
| 24 | 7 |
| 25 | 5 |
| 26 | 7 |
| 30 | 10 |
| 31 | 10 |
| 32 | 10 |
| 37 | 10 |
| 38 | 3 |
| 40 | 23 |
| 41 | 3 |
| 42 | 3 |
| 46 | 7 |
| 47 | 6 |
| 48 | 5 |
| 49 | 5 |
| 50 | 7 |
| 51 | 5 |
| 52 | 3 |
| 53 | 5 |
| 54 | 10 |
| 55 | 15 |
| 56 | 3 |
| 57 | 6 |
| 58 | 30 |
| 59 | 10 |
| 60 | 25 |
| 61 | 10 |
| 62 | 15 |
| 63 | 7 |
| 64 | 10 |
| 65 | 15 |
| 66 | 20 |
| 67 | 10 |
| 68 | 7 |
| 70 | 22 |
| 71 | >30 |
| 72 | 10 |
| 73 | 2 |
| 74 | 7 |
| 75 | 5 |
| 76 | 2 |
| 77 | 2 |
| 81 | 3 |
| 82 | 2 |
| 87 | 5 |
| 95 | 3 |
| 99 | 2 |
| 101 | >30 |
| 102 | >30 |
| 103 | >30 |
| 104 | 7 |
| 105 | 7 |
| 107 | 20 |
| 108 | 5 |
| 109 | 7 |
| 110 | >30 |
| 111 | 2 |
| 112 | 5 |
| 113 | 7 |
| 114 | 7 |
| 115 | 7 |
| 116 | 7 |
| 117 | 3 |
| 118 | 17 |
| 120 | 7 |
| 121 | 2 |
| 122 | 8 |
| 123 | >30 |
| 124 | 3 |
| 125 | 3 |
| 128 | 2 |
| 129 | 7 |
| 130 | 2 |

TABLE 3b-continued

Rescue from anti-NGF killing of SCG neurons

| Compounds | IC(50) (uM)* |
|---|---|
| 131 | 3 |
| 132 | 1 |
| 134 | 1 |
| 135 | 7 |
| 136 | 5 |
| 137 | 10 |
| 138 | 2 |
| 139 | 10 |
| 140 | 5 |
| 141 | >30 |
| 142 | >30 |
| 143 | 10 |
| 144 | 15 |
| 145 | 20 |
| 146 | 20 |
| 147 | 17 |
| 148 | 7 |
| 151 | 2 |
| 152 | 2 |
| 153 | 5 |

FIG. 1 illustrates the protection provided by compound 1 (referred to here as AEG3482) against Taxol™ induced killing. P1 Sprague Dawley rat SCG neurons were cultured and incubated with NGF (50 ng/mL) for 5 days. Addition of Taxol™ (50 ng/mL) resulted in a 72% loss in viability as measured by MTS staining. Co-treatment with compound 1 resulted in 100% protection at 10 uM, with an $IC_{50}$ of 7 uM.

EXAMPLE 156

In Vitro Protection of SCG Neurons from Cisplatin Killing

SCG neurons were isolated from day 1 neonatal Sprague Dawley rats, plated at a cell density of 10,000 cells/well, and incubated in Biowhittaker Utraculture containing 1% Pen-strep, 1% L-glutamine, 0.7% ARAC, 3% rat serum, and NGF (50 ng/mL, Calomone Labs) at 37° C., under a 5% $CO_2$ atmosphere. After 5 days the cells were treated with compound and cisplatin (3 μg/mL). Viability was assessed 48 hours later using MTS (Promega) staining.

TABLE 4

Protection of SCG neurons against cisplatin killing

| Entry | Compound | $IC_{50}$ (±1 μM) |
|---|---|---|
| 1 | 1 | 5 |

EXAMPLE 157

In Vitro Protection of SCG Neurons from Vincristine Killing

SCG neurons were isolated from day 1 neonatal Sprague Dawley rats, plated at a cell density of 10,000 cells/well, and incubated in Biowhittaker Utraculture containing 1% Pen-strep, 1% L-glutamine, 0.7% ARAC, 3% rat serum, and NGF (50 ng/mL, Calomone Labs) at 37° C., under a 5% $CO_2$ atmosphere. After 5 days the cells were treated with compound and vincristine (50 ng/mL). Viability was assessed 48 hours later using MTS (Promega) staining.

TABLE 5

Protection of SCG neurons against Vincristine killing

| Entry | Compound | $IC_{50}$ (±1 μM) |
|---|---|---|
| 1 | 1 | 10 |

EXAMPLE 158

Protection of Motor Neurons in Layer V of the Motor Cortex 350 uM slices of P1 rat motor cortex were obtained using a McIlwain tissue chopper (Mickle Laboratory Engineering Co., England). Slices were cultured in 50% Neurobasal, 25% HBSS, 25% Horse serum, 1% penicillin/streptomycin, 2 mM glutamine, 6.4 mg/mL glucose for 2 weeks. Neuronal death was initiated by addition of 5 mM malonate. Test compounds were added coincident with malonate and slices were cultured for an additional two weeks. Slices were fixed in 4% paraformaldehyde and stained with SMI-32 antibody (Sternberger monoclonals, Maryland). Large SMI positive cells with apical dendrites residing in layer V of the cortex were identified as motor neurons and counted. Malonate treatment greatly reduced the SMI-positive motor neuron count.

Figure 2:
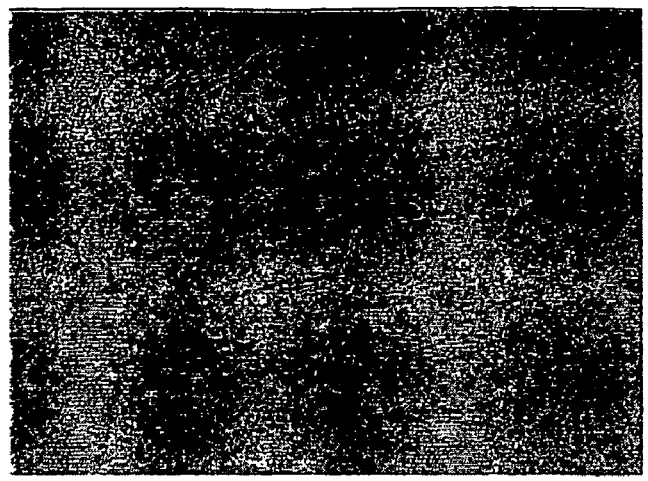
FIG. 2 illustrates the protection of cortical motor neurons from malonate killing in the presence of compound 91. 350 uM slices of P1 rat motor cortex were treated with malonate and incubated in media for 14 days, before malonate and drug were added. Part (a) shows control motor neurons, and illustrates large diamond-shaped neurons; part (b) shows malonate treatment alone, which results in killing with a complete loss of neurons; and part (c) shows 90% rescue of cortical motor neurons in the presence of compound 91 (1 uM) and malonate.
Figure 2:
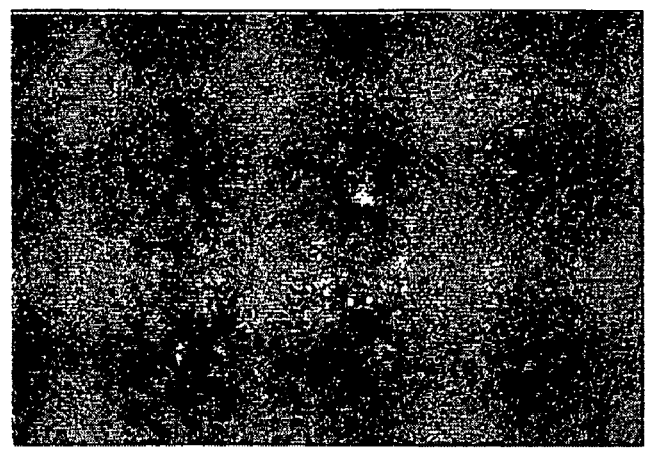
Figure 2:
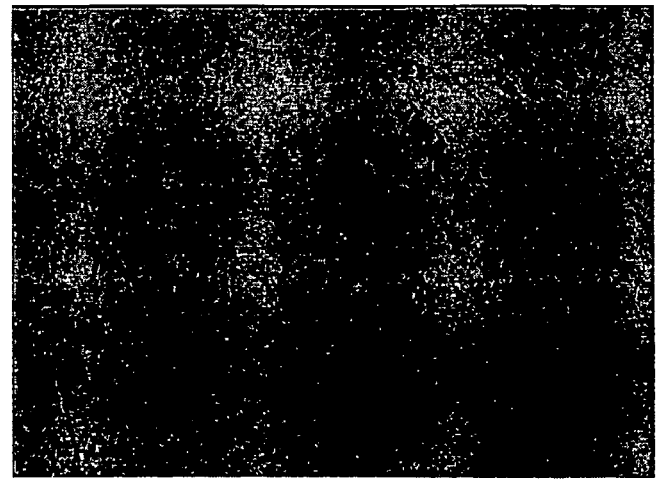

FIG. 2 illustrates the protection of cortical motor neurons from malonate killing. Slices of P1 rat motor cortex (350 uM) were treated with malonate and incubated in media for 14 days, before malonate and drug were added. Part (a) shows control motor neuons. Large sized diamond-shaped neurons are visible; part (b) shows malonate treatment alone, which results in killing with a complete loss of neurons; and part (c) shows 90% rescue of cortical motor neurons in the presence of compound 91 (1 uM) and malonate. In Part C, large diamond-shaped neurons are again visible.

EXAMPLE 159

Co-treatment of H460 and OV2008 cell line with Taxol™ and Compound 1

H460 and OV2008 cells were plated and incubated for 48 hours. Compound 1 and/or compound 1 and Taxol™ were added. Viability was determined after 24 hours, staining with MTT (Promega).

Figure 3:
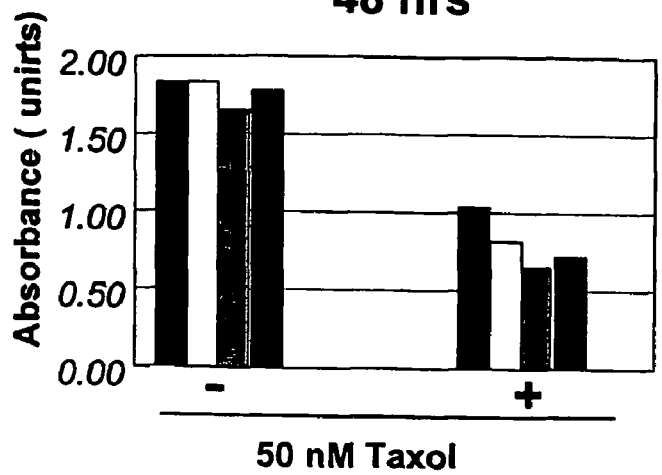
FIG. 3 illustrates the co-treatment of H460 and OV2008 cancer cell line with Taxol™ and Compound 1. H460 and OV2008 cells were treated with Taxol™ and/or Taxol™+ compound 1.
Figure 3:
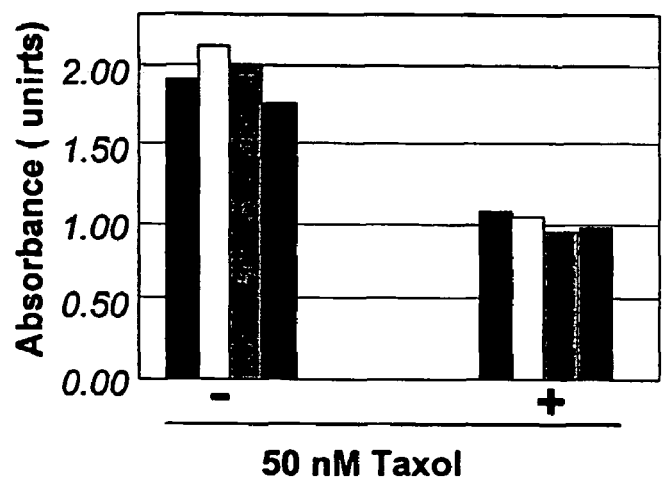

FIG. 3 illustrates the co-treatment of H460 and OV 2008 cell lines with Taxol™ and compound 1. H460 lung carcinoma and OV2008 ovarian carcinoma cells were treated with Taxol™ (50 nM) and/or Taxol™ (50 nM)+compound 1 (noted as AEG 03482) at levels of 5,10, and 20 uM. Compound 1 did not protect H460 or OV2008 cells from Taxol™ induced apoptosis.

EXAMPLE 160

Protection of Sprague Dawley Rats from Taxol™ Induced Neuropathies

Adult Sprague Dawley rats were treated with Taxol™ (IP, 9 mg/kg in Cremophor EL and ethanol) twice weekly for 3 weeks (J. Neuro-Oncology (1999) 41: 107–116). Compound was administered 1 hour prior to Taxol™ treatment (IP, 1, 5 and 10 mg/kg in hydroxypropyl-β-cyclodextrin). Taxol™ treated control animals were treated with saline solution at the same time of Compound treated animals. Non-treated control animals were treated with saline solution as above. Weight gain was measured every second day, starting at Day 1. Gait analysis was measured by quantifying the refracted light captured by a video camera as the animals walked over a glass plate, 2 days after the final Taxol™ treatment (Physiology and Behavior (1994), 55(4): 723–726; Med. Sci. Res. (1988) 16: 901–902). This data was analyzed by Northern Eclipse software. H/M wave recovery was analyzed using standard procedures 2 days after the final Taxol™ treatment (Muscle Nerve (1998) 21: 1405–1413; Annals of Neurology (1998) 43 (1): 46–55).

Figure 4:
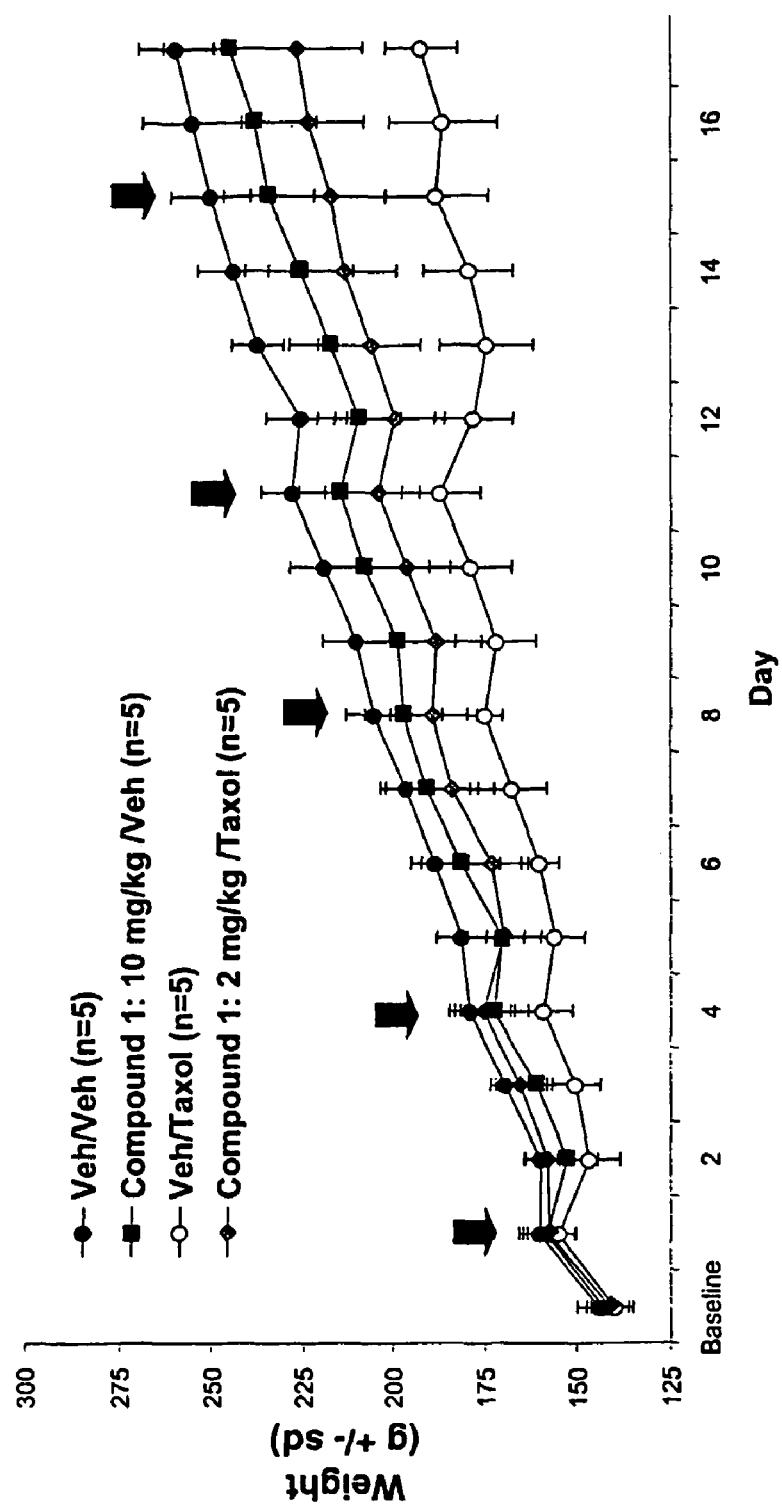
FIG. 4 illustrates weight loss induced by Taxol™ in Sprague Dawley rats treated with 50% HPDC vehicle (veh/veh), compound 1 dissolved in 50% HPDC at 1, 5, or 10 mg/kg (veh/1, veh/l5, veh/l 10, respectively), or Taxol™ (9 mg/kg)=compound 1 dissolved in 50% HPDC at 1, 5, and 10 mg/kg (Tax/1, Tax/5, Tax/10) according to the dosing regime described in Example 160.

FIG. 4 shows weight loss induced by Taxol™. Male Sprague Dawley rats were treated with 50% HPDC vehicle (veh/veh), compound 1 dissolved in 50% HPDC at 1,5, or 10 mg/kg (veh/1, veh/5, veh/10, respectively), or Taxol™(9 mg/kg)+compound 1 dissolved in 50% HPDC at 1,5, and 10 mg/kg (Tax/1, Tax/5, Tax/10) according to the dosing regime described in Example 160. Weight measurements were made ever other day.

Figure 5:
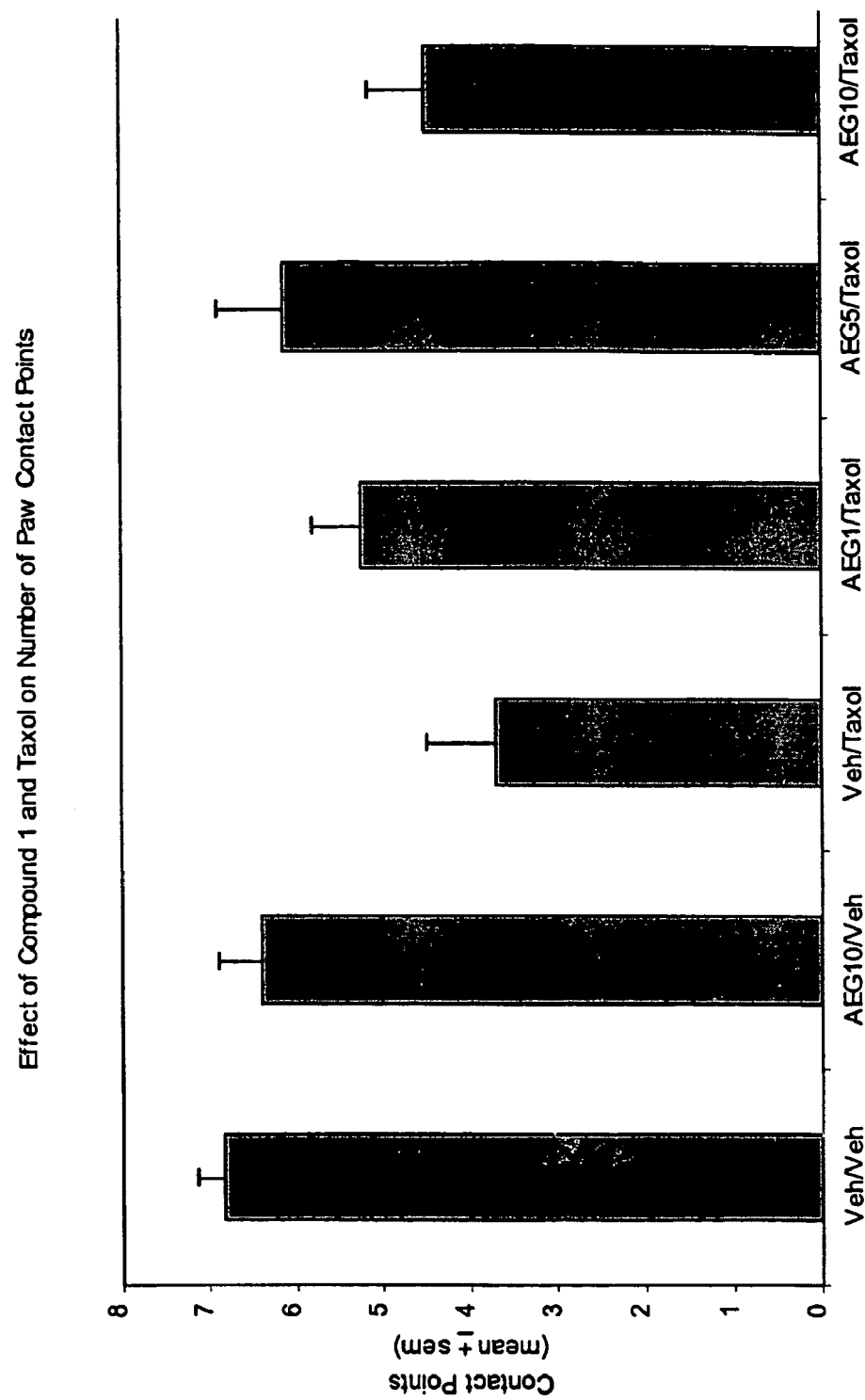
FIG. 5 illustrates that gait disturbance in rats induced by Taxol™ was reduced with compound 1.

FIG. 5 shows gait disturbance induced by Taxol™ with compound 1. Two days after the completion of drug treatments animal walking gait was analyzed according to a) total imprint area, and b) total number of contact points. Compound 1 prevented Taxol™ induced gait disturbance.

Figure 6:
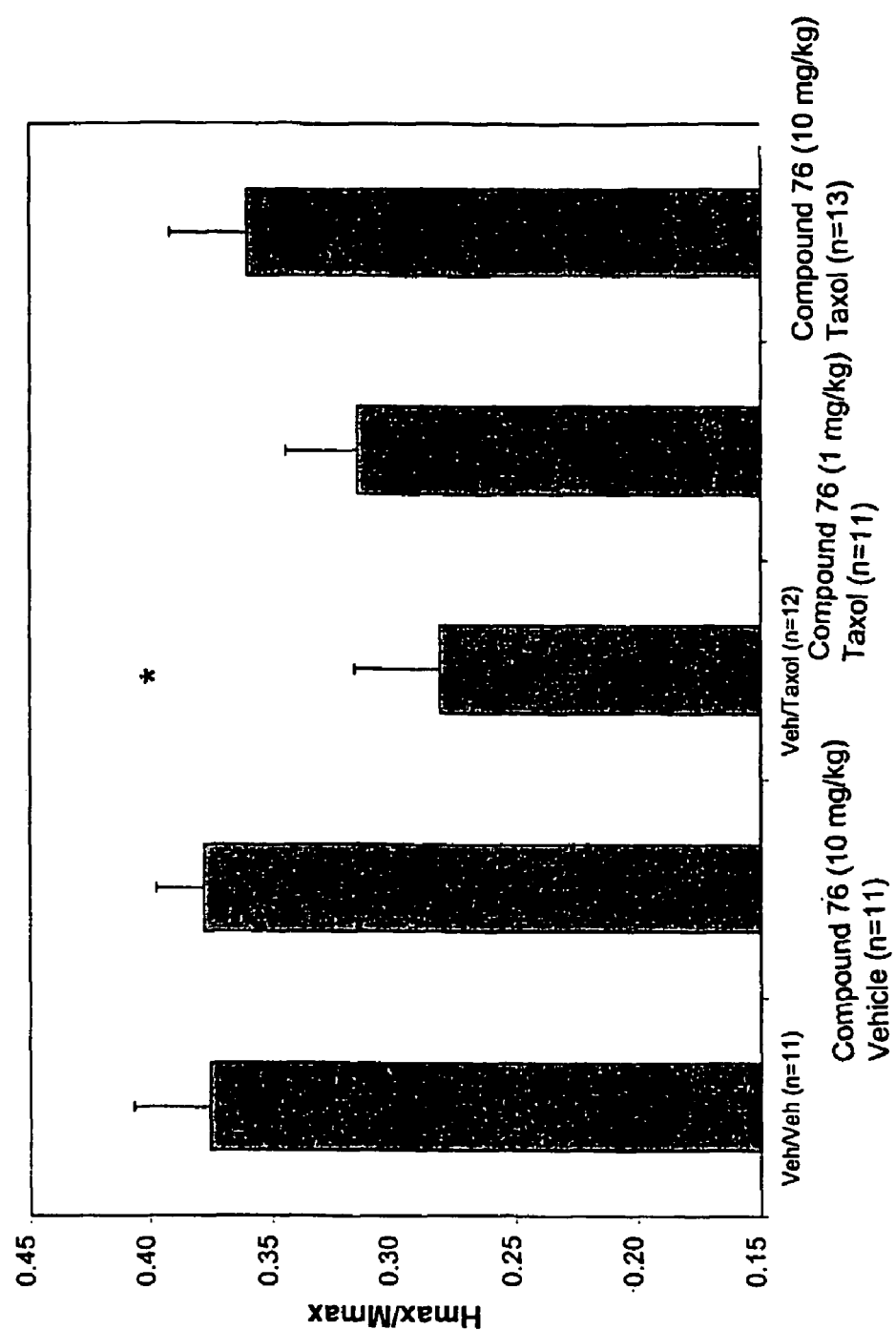
FIG. 6 illustrates that compound 1 caused a reversal in H/M wave disturbance induced by Taxol™, as indicated by H-reflex amplitude.

FIG. 6 illustrates the effect of Compound 1 on H-reflex amplitude, a measurement of H/M wave disturbance induced by Taxol™. Two days after the completion of drug treatments, the dorsal root ganlia and attached nerves were dissected bilaterally from L4 and L5 and their H/M wave conductance measured. Compound 1 caused a reversal in H/M wave disturbance induced by Taxol™.

EXAMPLE 161

Sciatic Nerve Crush Injury Model

Male Sprague Dawley rats were anaesthetized (halothane and buprenorphine) and the right hind leg was blunt dissected to expose the sciatic nerve at mid-thigh. The nerve was crushed twice for a total of 30 seconds using No.7 Dumont jeweller's forceps. The incision is sutured and the animals are allowed to recover for 28 days. Functional recovery was measured by gait, nerve conductance and toe spread measurements between digits 1and 5 and digits 2 and 4.

Figure 7:
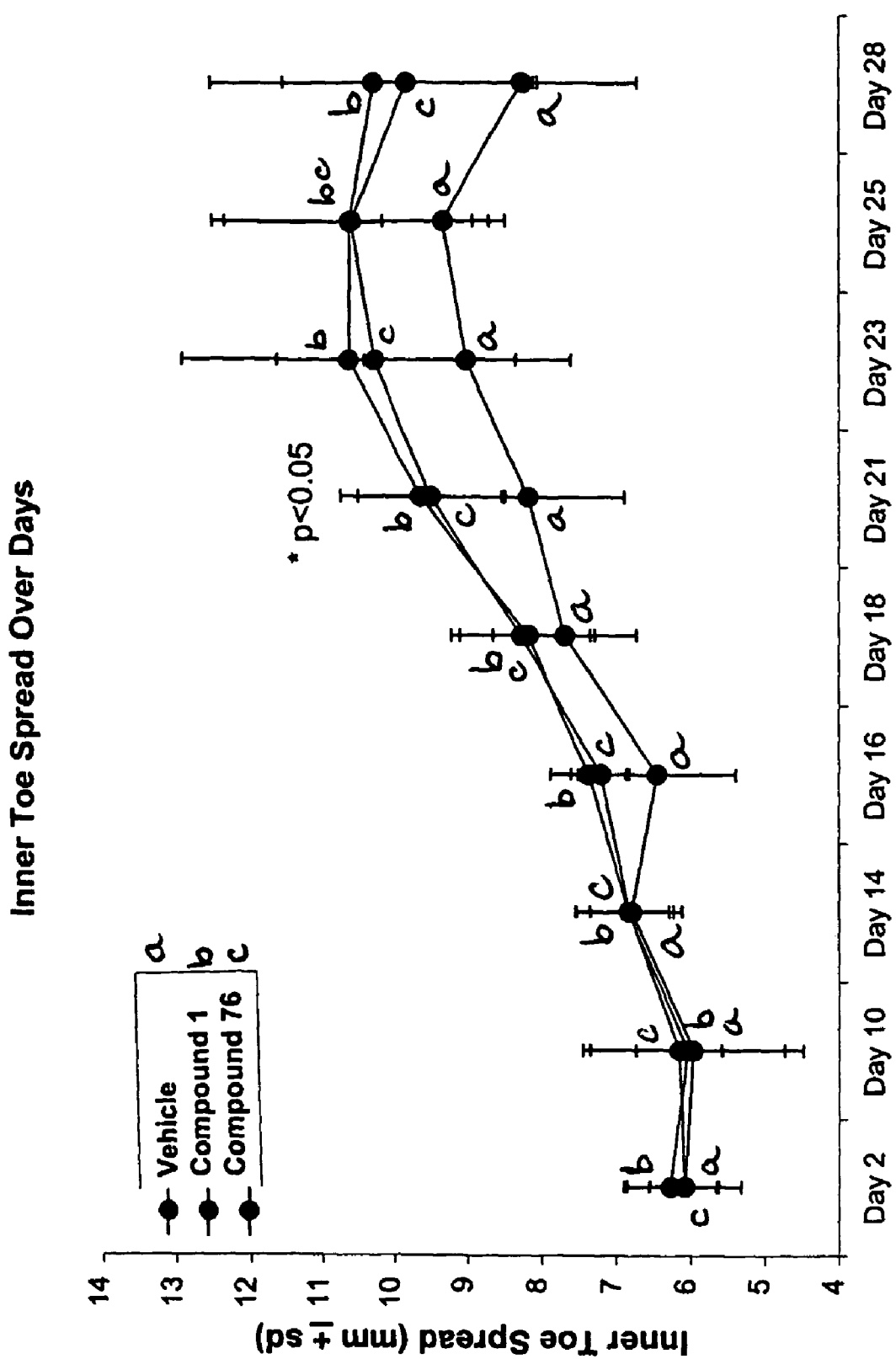
FIG. 7 illustrates sciatic nerve recovery after crush injury, as measured by inner toe spread in male Spraugue Dawley rats treated with either vehicle control; compound 1 or compound 76.

FIG. 7 illustrates sciatic nerve recovery after crush injury, as indicated by inner toe spread. Male Spraugue Dawley rats were subjected to sciatic nerve crush and treated with either vehicle control, compound 1 or compound 76 (noted as AEG 33764). Compounds 1 and 76 induced increased recovery in toe spread area.

EXAMPLE 162

Optical Stroke Model

The right eye of each rat was dilated fully using 1% tropacamide and 2.% pheylephrine hydrochloride (Alcon Canada). A single drop of 0.5% proparacaine (Alcon) was used as a topical anesthetic. The anterior chamber of the right eye was cannulated with a 30-gauge needle connected to a saline reservoir and a manometer to monitor intraocular pressure. Intraocular pressure was raised to 110 mm Hg by raising the saline reservoir for 60 minutes. This increase in pressure collapses the central retinal artery. Retinal ischemia was confirmed by whitening of the iris and loss of red reflex. After 60 minutes of ischemia, the intraocular pressure was normalized and the needle withdrawn. A 33-blunt needle (Hamilton) was inserted through the corneal puncture, maneuvered around the lens displacing it medially, and advanced into the intravitrial space. A 2 µL volume of drug or vehicle (50% HPCD) was injected into the vitreous of the eye. The needle was withdrawn and maxitrol (Alcon) was applied to the cornea to prevent infection. Alternatively, drug was given subcutaneously before or after the insult, for a period of up to 14 days.

Optical function after 24 hrs, 28 hrs and 7 days was assessed using ERG measurements and histological staining of the RG layer.

Figure 8:
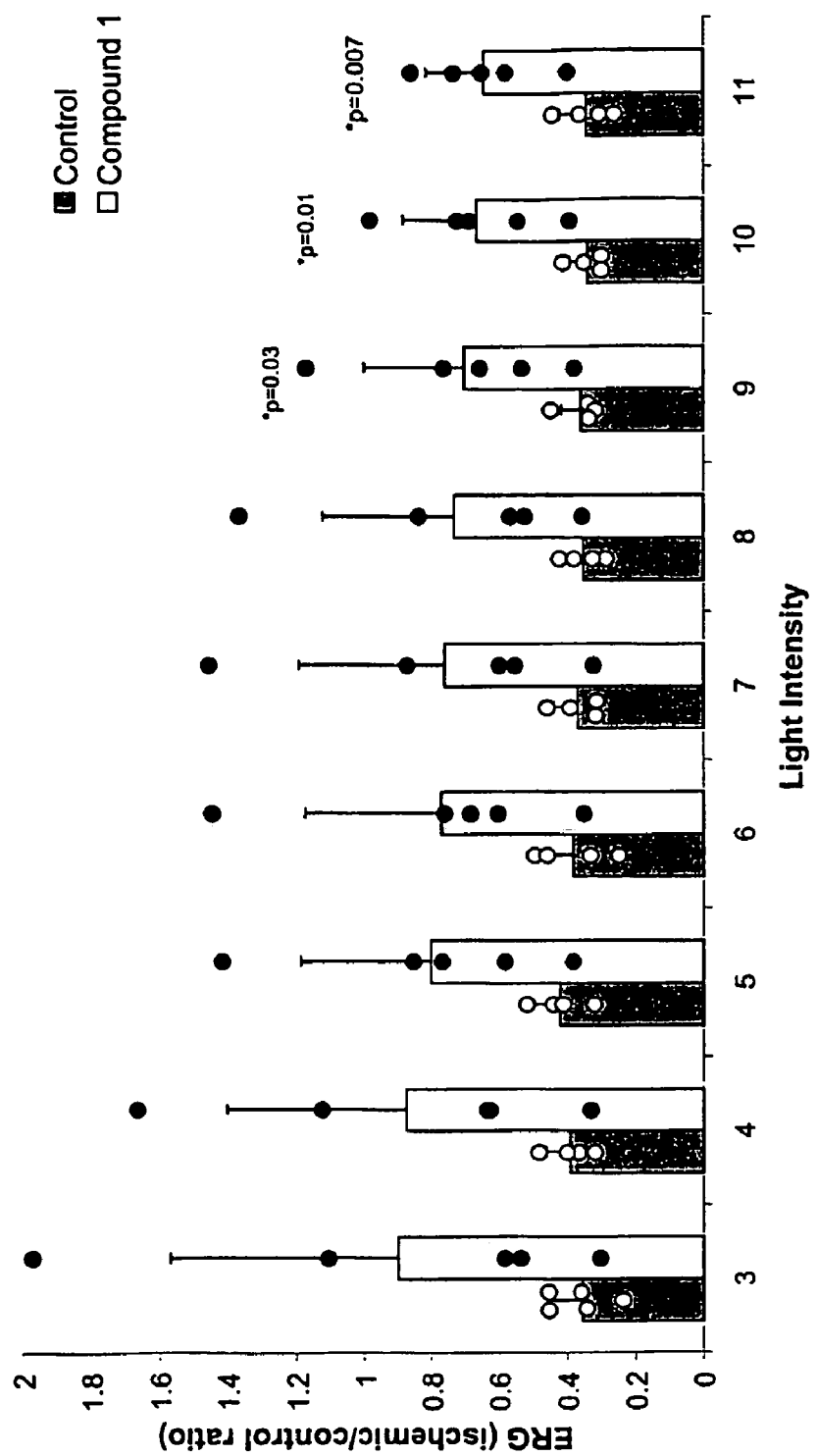
FIG. 8 illustrates the effect of intravitreal compound 1, followed by subsequent daily injections on protection of RGs after ocular stroke. Compound 1, given post stroke, protects the RG population allowing for normal conductance.

FIG. 8 shows protection of RGs by compound 1 after ocular stroke. Ocular stroke was induced in the right eye of rats resulting in almost complete loss of the RG population, as seen here by a loss in reactivity of the optic fiber to stimulation. Compound 1 was delivered intravitreally followed by subsequent daily injections for 1 week post-ischemia (post stroke). Compound 1, given post stroke, protects the RG population allowing for normal conductance.

EXAMPLE 163

CA II Inhibition

CA II inhabition was measured using the protocol described by Pocker, Y.' Stone, J. *Biochemistry* 1967, 6, 668. The IC (50)s if selected compound represented by Formula I are listed in Table 6.

TABLE 6

CA II inhibition by compounds represented by formula I

| Compounds | IC(50) (uM) |
|---|---|
| 1 | 0.250 |
| 4 | 0.217 |
| 5 | 0.192 |
| 6 | 0.164 |
| 7 | 0.581 |
| 8 | 1.47 |
| 11 | 1.80 |
| 12 | 1.59 |
| 13 | 4.05 |
| 14 | 0.198 |
| 15 | 0.152 |
| 16 | 0.150 |
| 17 | 0.179 |
| 18 | 0.337 |
| 19 | 0.373 |
| 20 | 0.404 |
| 21 | 5.32 |
| 22 | 0.153 |
| 24 | 0.613 |
| 25 | 0.302 |
| 37 | 0.199 |
| 38 | 0.577 |
| 39 | 0.154 |
| 40 | 1.52 |
| 41 | 0.346 |
| 42 | 0.272 |
| 43 | 0.886 |
| 44 | 0.619 |
| 45 | 0.166 |
| 46 | 0.601 |
| 47 | 0.361 |
| 48 | 0.288 |
| 49 | 0.466 |
| 50 | 0.938 |
| 72 | 1.61 |
| 72 | 2.19 |
| 74 | 1.68 |

TABLE 6-continued

CA II inhibition by compounds represented by formula I

| Compounds | IC(50) (uM) |
|---|---|
| 75 | 0.441 |
| 76 | 0.526 |
| 81 | 1.58 |
| 82 | 5.43 |
| 87 | 0.128 |
| 99 | 0.914 |
| 105 | 0.150 |
| 111 | 53.2 |
| 137 | 2.06 |
| 139 | 11.3 |
| 142 | 60.3 |

Example 164

Neuroprotection of Cortical Neurons in the Presence of beta-Amyloid

Primary neurona/glial cortical cultures were established from postnatal day 1 Sprague Dawley rats. Cerbral cortices were isolated and dissociated with 0.25% trypsin for 20 minutes at 37 degrees. The tissue was then triturated in PBS containing 0.1% bovine serum albumin and 0.2mglml DNAse. Cells were plated in poly D-lysine coated 96 well plates at a density of 1e6 cells per mL. Cultures were maintained at 37 degrees in 5% CO2/95% air for 2 weeks in Neurobasal (Gibco) supplemented with B27, glutamine, and penicillin/streptomycin. 5ng/mL AraC was added after 48 hours. After 2 weeks cells were exposed to 10 uM 25–35 amyloid beta peptide with and without 10 uM compound 76. After 2 days of treatment apoptotic cells were detected with Cy3-conjugated annexin V (Sigma).

Figure 9:
FIG. 9 illustrate the neuroprotection of cortical neurons provided by Compound 76 from amyloid beta 25–35 toxicity. Top (a) shows control untreated cultures display low level annexin V staining; middle (b) shows 48 hour treatment with amyloid beta peptide results in the appearance of apoptotic cells; and bottom (c) illustrates co-treatment with 10 uM Compound 76 prevents the occurrence of annex in V stained cells.
Figure 9:
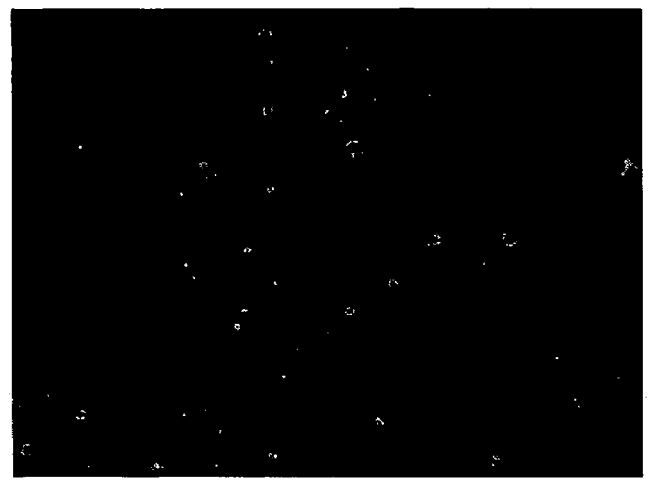
Figure 9:

FIG. 9 shows the protection of provided by Compound 76 from amyloid beta 25–35 toxicity. Mixed neuronal/cortical cultures were obtained from P1 rat cortex. After 2 weeks in vitro cells were exposed to 10 uM 25–35 amyloid beta peptide. Top (a) shows control untreated cultures display low level annexin V staining. Middle (b) shows 48 hour treatment with amyloid beta peptide results in the appearance of apoptotic cells which stain with annexin V on the cell periphery. Bottom (c) illustrates co-treatment with 10 uM Compound 76 prevents the occurrence of annex in V stained cells.

The invention claimed is:

1. A compound represented by formula:

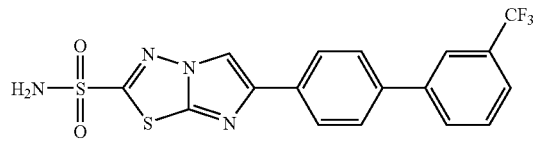

or pharmaceutically acceptable salts thereof.

2. A compound according to claim 1 wherein the compound is a pharmaceutically acceptable salt.

3. The compound of claim 2, wherein the pharmaceutically acceptable salt is sodium.

4. A pharmaceutical composition comprising a therapeutically effective amount of a compound of claim 1 and a pharmaceutically acceptable carrier.

5. A pharmaceutical package comprising the pharmaceutical composition according to claim 4 and instructions for use.

* * * * *